US007122344B2

(12) United States Patent
Pilon et al.

(10) Patent No.: US 7,122,344 B2
(45) Date of Patent: Oct. 17, 2006

(54) METHODS FOR THE PRODUCTION OF PURIFIED RECOMBINANT HUMAN UTEROGLOBIN FOR THE TREATMENT OF INFLAMMATORY AND FIBROTIC CONDITIONS

(75) Inventors: Aprile L. Pilon, Gaithersburg, MD (US); Richard W. Welch, Gaithersburg, MD (US)

(73) Assignee: Claragen, Inc., Gaithersburg, MD (US)

( * ) Notice: Subject to any disclaimer, the term of this patent is extended or adjusted under 35 U.S.C. 154(b) by 117 days.

(21) Appl. No.: 09/898,616

(22) Filed: Jul. 2, 2001

(65) Prior Publication Data
US 2003/0109429 A1 Jun. 12, 2003

Related U.S. Application Data

(63) Continuation-in-part of application No. 08/864,357, filed on May 28, 1997, now Pat. No. 6,255,281.

(51) Int. Cl.
*C12P 21/02* (2006.01)
*C07K 1/14* (2006.01)
*C07K 1/18* (2006.01)
*C07K 1/34* (2006.01)
*C07K 1/36* (2006.01)

(52) U.S. Cl. ............... 435/69.1; 530/412; 530/416; 530/417; 530/418

(58) Field of Classification Search ............ 530/412, 530/350; 435/7.1, 975, 252.3, 472; 514/2, 514/12, 6

See application file for complete search history.

(56) References Cited

U.S. PATENT DOCUMENTS

| 4,691,009 | A | * | 9/1987 | Palmer et al. ............... 530/350 |
| 5,266,562 | A | * | 11/1993 | Mukherjee et al. ............ 514/15 |
| 5,696,092 | A | | 12/1997 | Patierno et al. |
| 2002/0006640 | A1 | * | 1/2002 | Ni et al. ..................... 435/69.1 |
| 2002/0160948 | A1 | * | 10/2002 | Pilon et al. .................... 514/12 |

FOREIGN PATENT DOCUMENTS

| EP | 0617965 | 10/1994 |
| WO | WO 88/08983 | 11/1988 |
| WO | WO 96/09831 | 4/1996 |
| WO | WO 98/40657 | 12/1996 |

OTHER PUBLICATIONS

Torkkeli et al. (1978), Uterine and lung uteroglobins in the rabbit. Two similar proteins with differential hormonal regulation. Biochim Biophys Act. 544(3): 578-592.*

Scopes, R.K. (1994) Protein Purification Principles and Practice, 3rd Edition (Cantor, C.R., ed) pp. 270-277, Springer-Verlag, New York.*

Mourot et al. (1989), Comparative Evaluation of Ultrafiltration Membranes for Purifications of Synthetic Peptides, Separation Science and Technology, 24(5 & 6): 353-367.*

Mantile et al. (1993), Human Clara Cell 10-kDa Protein is the Counterpart of Rabbit Uteroglobin, J. Biol. Chem. 268(27): 20343-20351.*

Miele et al. (1990), High Level Bacterial Expression of Uteroglobin, a Dimeric Eukaryotic Protein with Two Interchain Disulfide Bridges, in its Natural Quaternary Structure, J. Biol. Chem. 265(11): 6427-6435.*

Peter et al. (1989), Recombinant rabbit uteroglobin expressed at high levels in *E. coli* forms stable dimers and binds progesterone, Protein Engineering 3(1): 61-66.*

Andersson et al. (1994), Heterologous Expression of Human Uteroglobin/Polychlorinated Biphenyl-binding Protein, J. Biol. Chem. 269(29): 19081-19087.*

Shin t al. (1997), Enhanced Production of Human Mini-Proinsulin in Fed-Batch Cultures at High Cell D nsity of *Escherichia coli* BL21(DE3) [pET-3aT2M2], Biotechnol. Prog. 13: 249-257.*

Torkkeli et al., "Uterine and lung uteroglobins it the rabbit. Two similar proteins with differential hormonal regulation", Biochim Biophys Act. 1978, vol. 544, No. 3, pp. 578-592.

Andersson et al., "Heterologous Expression of Human Uteroglobin/ Polychlorinated Biphenyl-binding Protein", J. Biol. Chem., Jul. 22, 1994, vol. 269, No. 29, pp. 19081-19087.

Mourot et al., "Comparative Evaluation of Ultrafiltration Membranes for Purification of Synthetic Peptides", Separation Science and Technology, 1989, vol. 24, No. 5 & 6, pp. 353-367.

Shin et al., "Enhanced Production of Human Mini-Proinsulin in Fed-Batch Cultures at High Cell Density of *Escherichia coli* BL21 (DE3)[pET-3aT2M2]", Biotechnol. Prog., 1997, vol. 113, pp. 249-257.

Pattabiraman et al., "Crystal Structure Analysis of Recombinant Human Uteroglobin and Molecular Modeling of Ligand Binding", Ann. NY. Acad. Sci. 2000, vol. 923, pp. 113-127.

* cited by examiner

*Primary Examiner*—Elizabeth Kemmerer
*Assistant Examiner*—Christina Borgeest
(74) *Attorney, Agent, or Firm*—Kramer Levin Naftalis & Frankel LLP; Barry Evans, Esq.; Henry Cittone, Esq.

(57) ABSTRACT

The present invention relates generally to the production of recombinant human uteroglobin (rhUG) for use as a therapeutic in the treatment of inflammation and fibrotic diseases. More particularly, the invention provides processes, including broadly the steps of bacterial expression and protein purification, for the scaled-up production of rhUG according to current Good Manufacturing Practices (cGMP). The invention further provides analytical assays for evaluating the relative strength of in vivo biological activity of rhUG produced via the scaled-up cGMP processes.

16 Claims, 35 Drawing Sheets

Fig. 9a

Purification used in Initial Toxicology study

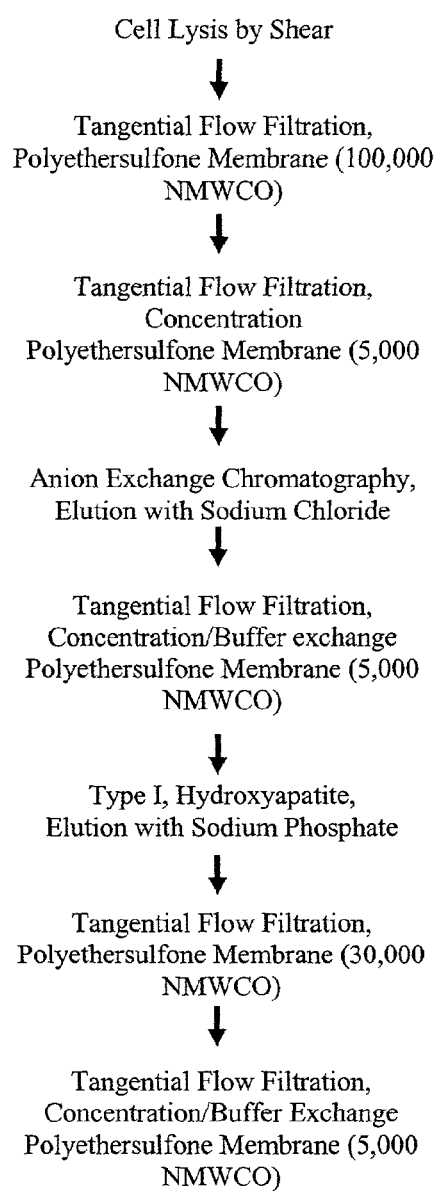

Cell Lysis by Shear
↓
Tangential Flow Filtration, Polyethersulfone Membrane (100,000 NMWCO)
↓
Tangential Flow Filtration, Concentration Polyethersulfone Membrane (5,000 NMWCO)
↓
Anion Exchange Chromatography, Elution with Sodium Chloride
↓
Tangential Flow Filtration, Concentration/Buffer exchange Polyethersulfone Membrane (5,000 NMWCO)
↓
Type I, Hydroxyapatite, Elution with Sodium Phosphate
↓
Tangential Flow Filtration, Polyethersulfone Membrane (30,000 NMWCO)
↓
Tangential Flow Filtration, Concentration/Buffer Exchange Polyethersulfone Membrane (5,000 NMWCO)

Fig. 9b

Purification used in first cGMP Manufacturing Run

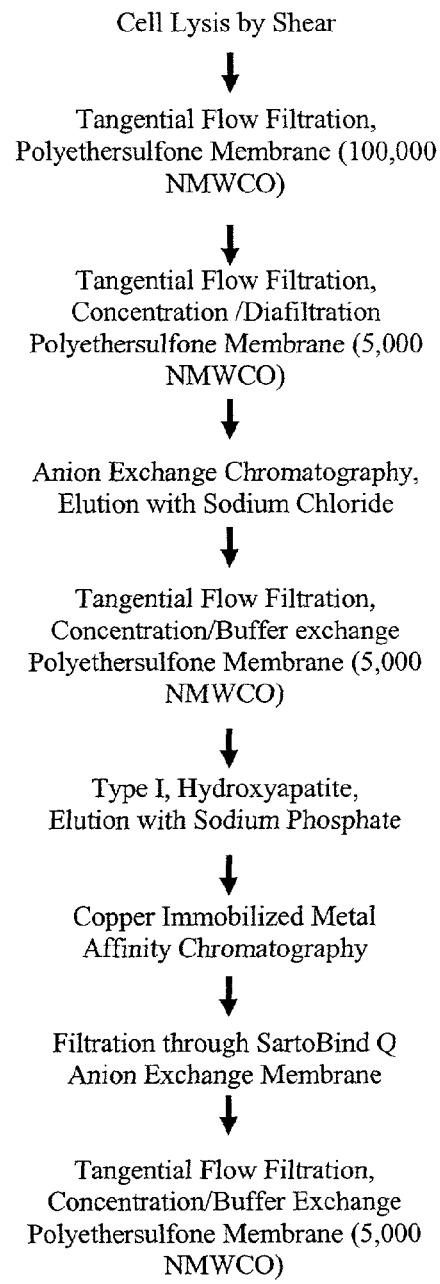

Cell Lysis by Shear
↓
Tangential Flow Filtration, Polyethersulfone Membrane (100,000 NMWCO)
↓
Tangential Flow Filtration, Concentration /Diafiltration Polyethersulfone Membrane (5,000 NMWCO)
↓
Anion Exchange Chromatography, Elution with Sodium Chloride
↓
Tangential Flow Filtration, Concentration/Buffer exchange Polyethersulfone Membrane (5,000 NMWCO)
↓
Type I, Hydroxyapatite, Elution with Sodium Phosphate
↓
Copper Immobilized Metal Affinity Chromatography
↓
Filtration through SartoBind Q Anion Exchange Membrane
↓
Tangential Flow Filtration, Concentration/Buffer Exchange Polyethersulfone Membrane (5,000 NMWCO)

Fig. 30

```
TATGCGGTGTGAAATACCGCACAGATGCGTAAGGAGAAAATACCGCATCAGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAGGTATCCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAGTCCAACCCGGTAAGACACGACTTATCGCCACTGGCA
GCAGCCACTGGTAACAGGATTAGCAGAGCGAGGTATGTAGGCGGTGCTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCATCCGTAAGATGCTTTTCTGTGACTGGTGAGTACTCAACCAAGTCAT
TCTGAGAATAGTGTATGCGGCGACCGAGTTGCTCTTGCCCGGCGTCAACACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGTGCACCCAACTGATCTTCAGCATC
TTTTACTTTCACCAGCGTTTCTGGGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTATTTAGAAAAATAAACAAAAGAGTTT
GTAGAAACGCAAAAAGGCCATCCGTCAGGATGGCCTTCTGCTTAATTTGATGCCTGGCAGTTTATGGCGGGCGTCCTGCCCGCCACCCTCCGGGCGT
TGCTTCGCAACGTTCAAATCCGCTCCCGGCGGATTGTCCTACTCAGGAGAGCGTTCACCGACAAACAACAGATAAAACGAAAGGCCCAGTCTTTCG
ACTGAGCCTTTCGTTTTATTTGATGCCTGGCAGTTCCCTACTCTCGCATGGGGAGACCCCACACTACCATCGGCGCTACGGCGTTTCACTTCTGAGTTC
GGCATGGGGTCAGGTGGGACCACCGCGCTACTGCCGCCAGGCAAATTCTGTTTTATCAGACCGCTTCTGCGTTCTGATTTAATCTGTATCAGGCTGAA
AATCTTCTCTCATCCGCCAAAACAGCCAAGCTTCACCTGCAGACAGAATTCTGTCTGCAGGTGAAGCTTCACCTGCAGACAGAATTCCGGAAGAGAG
CAAGGCTGGTGGGCGTGGACTCAAAGCATGGCAGCGGCAGAGGCTGGAGCAGTTGGGGATCTTCAGCTTCTAAATGCTAATTACACAGTGAGCTTTG
GGCTATTTTTTCCATGAGCTTAATGATGCTTTCTCTGGGCTTTTGGGGGAGGGTGTCCACCAGCTTCTTCAGCTGAGCCCCTGCCTCCCTCATGTCTTGA
TCAGGGCTGAAAAGTTCCATGGCAGCCTCATAACTGGAGGGTGTGTCCATGAGGAGGGTTTCGATGACACGCTGAAAGCTCGGGCAGATCTCTGCAG
CCATGGTGTATATCTCCTTCTTAAAGTTAACAAAATTATTTCTAGAGGGAAACCGTTGTGGTCTCCCTATAGTGAGTCGTATTAATTTGGATCCTCTAG
AGTCGACCTGCAGGCATGCCAGCTTCTGGTTCGTCGGCTGGGTGATGGCGTCGGTTTTGGCCGGCGGCGTCGGCGATCGCCAGCGCGAAGCAACT
GGCGTTCCTCGGCGAACATAGCGGCATGGTGGCCTTCGGCTTCTTCCGCGACCAGGTGAAGGACATGCACTGCGATGCGGACGTGATCCTGGCCCGG
TGGGATGAAAAGGCGAACTCGCCGGTGGTCTACCGCTGCCCGAAGGCGTACCTGCTCAACAGGTTCGCATCCGCGCCCTTCGTGCCCTGGCCGGACT
ACACCGAGGGGGAAAGCGAGGATCTAGGTAGGGCGCTCGCAGCCGCCTGCGGGACGCGAAAAGGTGAGAAAAGCCGGGCACTGCCCGGCTTTATT
TTTGCTGCTGCGCGTTCCAGGCCGCCCACACTCGTTTGACCTGGCTCGGGCTGCATCCGACCAGCTTGGCCGTCGTTGGCAATGCTCGATCCGCCGGAG
CGAAGCGTGATGATGCGGTCGTGCATGCCGGCGTCACGTTTGCGGCCGGTGTAGCGGCCGGCGGCCTTCGCCAACTGGACACCCTGACGTTGACGCT
CGCGCCGATCCTCGTAGTCGTCGCGGGCCATCTGCAAGGCGAGCTTCAAAAGCATCGTCCTGGACGGATTCCAGAACGATTTTCGCCACTCCGTTCGCC
TCGGCGGCCAGCTCCGACAGGTCCACCACGCCAGGCACGGCCAGCTTGGCCCCTTTGGCCCGGATCGACGCAACCAGGCGCTCGGCCTCGGCCAACG
GCAAGCGGCTGATGCGGTCGATCTTCTCCGCCAACGACGACTTCACCAGGTTGCAGGTCCGCGATCATGCAGCAGCTCGGGCCGGTCGGCGCGTGC
GCCGGACGCCTTCTGCGGTAGATGCCGGCGACGTAGTACCCGGCGGCCGCGTGGCCGCTACAAGGCTCTCCTGGCGTTCAAGATTCTGCTCGTCCG
TACTGGCGCGCAGGTAGATGCGGGCGACCTTCAACCTTCGTCCCTCCGGTTGTTGCTCTCGGCTCGCCATTTCCACGGCCTCGACGGCGTGCGGATCGG
ACCAGAGGCCGACGCGCTTGCCTCGCGCCTCCTGTTCGAGCCGCAGCATTTCAGGGTCGGCCGCGCGGCCGTGGAAGCGATAGGCCCACGCCATGCC
CTGGTGAACCATCGCGGCGTTGACGTTGCGCGGCGCTGCGGCGGCCGGCTGGCCAGCTCCATGTTGACCCACACGGTGCCCAGCGTGCGGCCGTAACGG
TCGGTGTCCTTCTCGTCGACCAGGACGTGCCGGCGGAACACCATGCCGGCGATCCGCCTGGCGCGCAAGGCCTTGCCGAAGGCTTGCCGCTTTCCGGCGC
GTCAATGTCCACCAGGCGCACGCGCACCGGCTGCTTGTCTACCAGCACGTCGATGGTGTCCGTCGATGATGCGCACGACCTCGCCGCGCAGCTCG
GCCCATGCGGCGGAGGCAACGACCAGGACGGCCAGCGCGGCAGCGGCGCGCAGCATGGCGTAGCTTCGGCGCTTCATGCGTGGCCCCATTGCTGATG
ATCGGGGTACGCCAGGTGCAGCACTGCATCGAAATTGGCCTTGCAGTAGCCGTCCAGCGCCACCGCGGAGCCGAACGCCGGCGAAAGGTACTCGACC
AGGCCGGGCCGGTCGCGGACCTCGCGCCCCAGGACGTGGATGCGCCGGCCGCGTGTGCCGTCGGGTCCAGGCACGAAGGCCAGCGCCTCGATGTTGA
AGTCGATGGATAGAAGTTGTCGGTAGTGCTTGGCCGCCCTCATCGCGTCCCCCTTGGTCAAATTGGGTATACCCATTTGGGCCTAGTCTAGCCGGCAT
GGCGCATTACAGCAATACGCAATTTAAATGCGCCTAGCGCATTTCCCGACCTTAATCGCCTCGCGCTGTAGCCTCACGCCCACATGTGCTAATG
TGGTTACGTGTATTTTATGGAGGTTATCCAATGAGCCGCCTGACAATCGACATGACGGACCAGCAGCACCAGAGCCTGAAAGCCCTGGCCGCCTTGC
AGGGCAAGACCATTAAGCAATACGCCCTCGAACGTCTGTTCCCCGGTGACGCTGATGCCGATCAGGCATGGCAGGAACTGAAAACCATGCTGGGGAA
CCGCATCAACGATGGGCTTGCCGGCCAAGGTGTCCACCAAGAGCGTCGGCGAAATTCTTGATGAAGAACTCAGCGGGGATCGCGCTTGACGGCCTACA
TCCTCACGGCTGAGGCCGAAGCCGATCTACGCGGCATCATCCGCTACACGCGCGGGAGTGGGGCGCGGCAGGTGCGCCGCTATATCGCTAAGCT
GGAACAGGGCATAGCCAGGCTTGCCGCCGGCGAAGGCCCGTTTAAGGACATGAGCGAACTCTTTCCCGCGCTGCGGATGGCCCGCTGCGAACACCAC
TACGTTTTTTGCCTGCCGCGTGCGGGCGAACCCGCGTTGGTCGTGGCGATCCTGCATGAGCGCATGGACCTCATGACGCGACTTGCCGACAGGCTCAA
GGGCTGATTTCAGCCGCTAAAAATCGCGCCACTCACAACGTCCTGATGGCGTACTTACCCAAAGAACAGCTAGGAGAATCATTTATGCTCAGCACAC
TTCCACAAGCTCATGCAACTTTCTTGAACCGCATCCGCGATGCGGTCGCTTCCGATGTTCGCTTCCGCGCTCTTCTGATCGGCGGCTCTTACGTTCACG
GAGGACTCGATGAGCACTCCGATTTGGATTTCGACATCGTTGTTGAGGACAACTGCTACGCAGATGTCTTGTCTACACGCAAGGATTTTGCCGAGGCA
CTGCCCGGCTTCCTCAACGCGATAAGCTGGCTGGATCCTCTACGCCGGACGCATCACCGGCGCATCCGGGCGCCACAGGTGCGGTTGCTGGCGCCT
ATATCGCCGACATCACCGATGGGGAAGATCGGGCTCGCCACTTCGGGCTCATGAGCGCTTGTTTCGGCGTGGGTATGGTGGCAGGCCCCGTGGCCGG
GGGACTGTTGGGCGCCATCTCCTTGCATGCACCATTCCTTGCGGCGGCGGTGCTCAACGGCCTCAACCTACTACTGGGCTGCTTCCTAATGCAGGAGT
CGCATAAGGGAGAGCGTCGACCGATGCCCTTGAGAGCCTTCAACCCAGTCAGCTCCTTCCGGTGGGCGCGGGGCATGACTATCGTCGCCGCACTTAT
GACTGTCTCTTTATCATGCAACTCGTAGGACAGGTGCCGGCAGCGCTCTGGGTCATTTTCGGCGAGGACCGCTTTCGCTGGAGCGCGACGATGATCG
GCCTGTCGCTTGCGGTATTCGGAATCTTGCACGCCCTCGCTCAAGCCTTCGTCACTGGTCCCGCCACCAAACGTTTCGGCGAGAAGCAGGCCATTATC
GCCGGCATGGCGGCCGACGCGTGGCTACGTCTTGCTGGCGTTCGCGACGCGAGGCTGGATGGCCTTCCCCATTATGATTCTTCTCGCTTCCGGCGG
CATCGGGATGCCCGCGTTGCAGGCCATGCTGTCCAGGCAGGTAGATGACGACCATCAGGGACAGCTTCAAGGATCGCTCGCGGCTCTTACCAGCCTA
ACTTCGATCATTGGACCGCTGATCGTCACGGCGATTTATGCCGCCTCGGCGAGCACATGGAACGGGTTGGCATGGATTGTAGGCGCCGCCCTATACCT
TGTCTGCCTCCCCGCGTTGCGTCGCGGTGCATGGAGCGGGCCACCTCGACCTGAATGGAAGCCGGCGGCACCTCGCTAACGGATTCACCACTCCAA
GAATTGGAGCCAATCAATTCTTGCGGAGAACTGTGAATGCGCAAACCAACCCTTGGCAGAACATATCCATCGCGTCCGCCATCTCCAGCAGCCGCAC
GCGGCGCATCTCGGGCAGCGTTGGGTCCTGGCCACGGGTGCGCATGATCGTGCTCCTGTCGTTGAGGACCCGGCTAGGCTGGCGGGGTTGCCTTACTG
GTTAGCAGAATGAATCACCGATACGCGAGCGAACGTGAAGCGACTGCTGCTGCAAAACGTCTGCGACCTGAGCAACAACATGAATGGTCTTCGGTTT
CCGTGTTTCGTAAAGTCTGGAAACGCGGAAGTCAGCGCCCTGCACCATTATGTTCCGGATCTGCATCGCAGGATGCTGCTGGCTACCCTGTGGAACAC
CTACATCTGTATTAACGAAGCGCTGGCATTGACCCTGAGTGATTTTTCTCTGGTCCCGCCGCATCCATACCGCCAGTTGTTTACCCTCACAACGTTCCA
GTAACCGGGCATGTTCATCATCAGTAACCCGTATCGTGAGCATCCTCTCTCGTTTCATCGGTATCATTACCCCCATGAACAGAAATCCCCCTTACACGG
AGGCATCAGTGACCAAACAGGAAAAAACCGCCCTTAACATGGCCCGCTTTATCAGAAGCCAGACATTAACGCTTCTGGAGAAACTCAACGAGCTGGA
CGCGGATGAACAGGCAGACATCGTGAATCGCTTCACGACCACGCTGATGAGCTTTACCGCAGCTGCCTCGCGCGTTTCGGTGATGACGGTGAAAAC
CTCTGACACATGCAGCTCCCGGAGACGGTCACAGCTTGTCTGTAAGCGGATGCCGGGAGCAGACAAGCCCGTCAGGGCGCGTCAGCGGGTGTTGGCG
GGTGTCGGGGCGCAGCCATGACCCAGTCACGTAGCGATAGCGGAGTGTATACTGGCTTAACTATGCGGCATCAGAGCAGATTGTACTGAGAGTGCAC
CA
```

Fig. 31

Met Ala Ala Glu Ile Cys Pro Ser Phe Gln Arg Val Ile Glu Thr Leu Leu Met Asp Thr Pro Ser Ser Tyr Glu
Ala Ala Met Glu Leu Phe Ser Pro Asp Gln Asp Met Arg Glu Ala Gly Ala Gln Leu Lys Lys Leu Val Asp
Thr Leu Pro Gln Lys Pro Arg Glu Ser Ile Ile Lys Leu Met Glu Lys Ile Ala Gln Ser Ser Leu Cys Asn

SEQUENCE LISTING

<160> NUMBER OF SEQ ID NOS: 11

<210> SEQ ID NO 1
<211> LENGTH: 65
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 1
gatccatgga aatctgcccg tctttccagc gtgttatcga aaccctgctg atggacaccc      60
cgtcc                                                                 65

<210> SEQ ID NO 2
<211> LENGTH: 60
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 2
agctacgaag cagctatgga actgttctct ccggaccagg acatgcgtga agcaggtgct      60

<210> SEQ ID NO 3
<211> LENGTH: 59
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 3
cagctgaaga aactggttga caccctgccg cagaaaccgc gtgaatccat cataaactg       59

<210> SEQ ID NO 4
<211> LENGTH: 37
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 4

```
atggagaaga tcgctcagtc tagcctgtgc aactaag                         37
```

<210> SEQ ID NO 5
<211> LENGTH: 60
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 5

```
cttagttgca caggctagac tgagcgatct tctccatcag tttgatgatg gattcacgcg   60
```

<210> SEQ ID NO 6
<211> LENGTH: 59
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 6

```
gtttctgcgg cagggtgtca accagtttct tcagctgagc actgcttcac gcatgtcct    59
```

<210> SEQ ID NO 7
<211> LENGTH: 60
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 7

```
ggtccggaga gaacagttcc atagctgctt cgtagctgga cggggtgtcc atcagcaggg   60
```

<210> SEQ ID NO 8
<211> LENGTH: 60
<212> TYPE: DNA
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 8

```
ggtccggaga gaacagttcc atagctgctt cgtagctgga cggggtgtcc atcagcaggg   60
```

<210> SEQ ID NO 9
<211> LENGTH: 7615
<212> TYPE: DNA
<213> ORGANISM: Artificial Sequence
<220> FEATURE:
<223> OTHER INFORMATION: Original amino acid sequence obtained from cDNA. Current sumitted sequence maximized for expression in E. coli.
<220> FEATURE:
<221> NAME/KEY: misc_feature
<223> OTHER INFORMATION: Original amino acid sequence obtained from cDNA. Current sumitted sequence maximized for expression in E. coli.

<400> SEQUENCE: 9

```
tatgcggtgt gaaataccgc acagatgcgt aaggagaaaa taccgcatca ggcgctcttc      60
cgcttcctcg ctcactgact cgctgcgctc ggtcgttcgg ctgcggcgag cggtatcagc     120
tcactcaaag gcggtaatac ggttatccac agaatcaggg gataacgcag gaaagaacat     180
gtgagcaaaa ggccagcaaa aggccaggaa ccgtaaaaag gccgcgttgc tggcgttttt     240
ccataggctc cgcccccctg acgagcatca caaaaatcga cgctcaagtc agaggtggcg     300
aaacccgaca ggactataaa gataccaggc gtttccccct ggaagctccc tcgtgcgctc     360
tcctgttccg accctgccgc ttaccggata cctgtccgcc tttctccctt cgggaagcgt     420
ggcgctttct catagctcac gctgtaggta tctcagttcg gtgtaggtcg ttcgctccaa     480
gctgggctgt gtgcacgaac ccccgttca gcccgaccgc tgcgccttat ccggtaacta     540
tcgtcttgag tccaacccgg taagacacga cttatcgcca ctggcagcag ccactggtaa     600
caggattagc agagcgaggt atgtaggcgg tgctacagag ttcttgaagt ggtggcctaa     660
ctacggctac actagaagga cagtatttgg tatctgcgct ctgctgaagc cagttacctt     720
cggaaaaaga gttggtagct cttgatccgg caaacaaacc accgctggta gcggtggttt     780
ttttgtttgc aagcagcaga ttacgcgcag aaaaaaagga tctcaagaag atcctttgat     840
cttttctacg gggtctgacg ctcagtggaa cgaaaactca cgttaaggga ttttggtcat     900
gagattatca aaaaggatct tcacctagat ccttttaaat taaaaatgaa gttttaaatc     960
aatctaaagt atatatgagt aaacttggtc tgacagttac caatgcttaa tcagtgaggc    1020
acctatctca gcgatctgtc tatttcgttc atccatagtt gcctgactcc ccgtcgtgta    1080
gataactacg atacgggagg gcttaccatc tggccccagt gctgcaatga taccgcgaga    1140
cccacgctca ccggctccag atttatcagc aataaaccag ccagccggaa gggccgagcg    1200
cagaagtggt cctgcaactt tatccgcctc catccagtct attaattgtt gccgggaagc    1260
tagagtaagt agttcgccag ttaatagttt gcgcaacgtt gttgccattg ctacaggcat    1320
cgtggtgtca cgctcgtcgt ttggtatggc ttcattcagc tccggttccc aacgatcaag    1380
gcgagttaca tgatccccca tgttgtgcaa aaaagcggtt agctccttcg gtcctccgat    1440
cgttgtcaga agtaagttgg ccgcagtgtt atcactcatg gttatggcag cactgcataa    1500
ttctcttact gtcatgccat ccgtaagatg cttttctgtg actggtgagt actcaaccaa    1560
gtcattctga gaatagtgta tgcggcgacc gagttgctct tgcccggcgt caacacggga    1620
taataccgcg ccacatagca gaactttaaa agtgctcatc attggaaaac gttcttcggg    1680
gcgaaaactc tcaaggatct taccgctgtt gagatccagt tcgatgtaac ccactcgtgc    1740
acccaactga tcttcagcat cttttacttt caccagcgtt tctgggtgag caaaaacagg    1800
aaggcaaaat gccgcaaaaa agggaataag ggcgacacgg aaatgttgaa tactcatact    1860
```

```
cttcctttttt caatattatt gaagcatttta tcagggttat tgtctcatga gcggatacat   1920
atttgaatgt  atttagaaaa  ataaacaaaa  gagtttgtag  aaacgcaaaa  aggccatccg   1980
tcaggatggc  cttctgctta  atttgatgcc  tggcagttta  tggcgggcgt  cctgcccgcc   2040
accctccggg  ccgttgcttc  gcaacgttca  aatccgctcc  cggcggattt  gtcctactca   2100
ggagagcgtt  caccgacaaa  caacagataa  aacgaaaggc  ccagtctttc  gactgagcct   2160
ttcgttttat  ttgatgcctg  gcagttccct  actctcgcat  ggggagaccc  cacactacca   2220
tcggcgctac  ggcgtttcac  ttctgagttc  ggcatggggt  caggtgggac  caccgcgcta   2280
ctgccgccag  gcaaattctg  ttttatcaga  ccgcttctgc  gttctgattt  aatctgtatc   2340
aggctgaaaa  tcttctctca  tccgccaaaa  cagccaagct  tcacctgcag  acagaattct   2400
gtctgcaggt  gaagcttcac  ctgcagacag  aattccggaa  gagagcaagg  ctggtgggcg   2460
tggactcaaa  gcatggcagc  ggcagaggct  ggagcagttg  gggatcttca  gcttctaaat   2520
gctaattaca  cagtgagctt  tgggctatttt  tttccatgag  cttaatgatg  ctttctctgg   2580
gcttttgggg  gagggtgtcc  accagcttct  tcagctgagc  ccctgcctcc  ctcatgtctt   2640
gatcagggct  gaaaagttcc  atggcagcct  cataactgga  gggtgtgtcc  atgaggaggg   2700
tttcgatgac  acgctgaaag  ctcgggcaga  tctctgcagc  catggtgtat  atctccttct   2760
taaagttaac  aaaattattt  ctagagggaa  accgttgtgg  tctccctata  gtgagtcgta   2820
ttaatttgga  tcctctagag  tcgacctgca  ggcatgccag  cttctggttc  gtcggctggg   2880
tgatggcgtc  ggttttggcc  ggcggcgtcg  gcgcgatcgc  cagcgcgaag  caactggcgt   2940
tcctcggcga  acatagcggc  atggtggcct  tcggcttctt  ccgcgaccag  gtgaaggaca   3000
tgcactgcga  tgcggacgtg  atcctggccc  ggtgggatga  aaaggcgaac  tcgccggtgg   3060
tctaccgctg  cccgaaggcg  tacctgctca  acaggttcgc  atccgcgccc  ttcgtgccct   3120
ggccggacta  caccgagggg  gaaagcgagg  atctaggtag  ggcgctcgca  gcggccctgc   3180
gggacgcgaa  aaggtgagaa  agccgggca  ctgcccggct  ttattttgc  tgctgcgcgt   3240 tccaggccgc  ccacactcgt  ttgacctggc  tcgggctgca  tccgaccagc  ttggccgtct   3300
tggcaatgct  cgatccgccg  gagcgaagcg  tgatgatgcg  gtcgtgcatg  ccggcgtcac   3360
gtttgcggcc  ggtgtagcgg  ccggcggcct  tcgccaactg  gacaccctga  cgttgacgct   3420
cgcgccgatc  ctcgtagtcg  tcgcgggcca  tctgcaaggc  gagcttcaaa  agcatgtcct   3480
ggacggattc  cagaacgatt  tcgccactc   cgttcgcctc  ggcggccagc  tccgacaggt   3540
ccaccacgcc  aggcacggcc  agcttggccc  ctttggcccg  gatcgacgca  accaggcgct   3600
cggcctcggc  caacggcaag  cggctgatgc  ggtcgatctt  ctccgcaacg  acgacttcac   3660
caggttgcag  gtccgcgatc  atgcgcagca  gctcgggccg  gtcggcgcgt  gcgccggacg   3720
ccttctcgcg  gtagatgccg  gcgacgtagt  acccggcggc  ccgcgtggcc  gctacaaggc   3780
tctcctggcg  ttcaagattc  tgctcgtccg  tactggcgcg  caggtagatg  cgggcgacct   3840
tcaaccttcg  tccctccggt  tgttgctctc  gcgtcgccat  ttccacggct  cgacggcgtg   3900
cggatcggac  cagaggccga  cgcgcttgcc  tcgcgcctcc  tgttcgagcc  gcagcatttc   3960
agggtcggcc  gcgcggccgt  ggaagcgata  ggcccacgcc  atgccctggt  gaaccatcgc   4020
ggcgttgacg  ttgcgcggct  gcggcggccg  gctggccagc  tccatgttga  cccacacggt   4080
gcccagcgtg  cggccgtaac  ggtcggtgtc  cttctcgtcg  accaggacgt  gccggcggaa   4140
caccatgccg  gccagcgcct  ggcgcgcacg  ttcgccgaag  gcttccgcct  tttccggcgc   4200
gtcaatgtcc  accaggcgca  cgcgcaccgg  ctgcttgtct  accagcacgt  cgatggtgtc   4260
```

```
gccgtcgatg atgcgcacga cctcgccgcg cagctcggcc catgccggcg aggcaacgac      4320
caggacggcc agcgcggcag cggcgcgcag catggcgtag cttcggcgct tcatgcgtgg      4380
ccccattgct gatgatcggg gtacgccagg tgcagcactg catcgaaatt ggccttgcag      4440
tagccgtcca gcgccacccg cgagccgaac gccggcgaaa ggtactcgac caggccgggc      4500
cggtcgcgga cctcgcgccc caggacgtgg atgcgccggc gcgtgtgcc gtcgggtcca       4560 ggcacgaagg ccagcgcctc gatgttgaag tcgatggata aagttgtcg gtagtgcttg       4620 gccgccctca tcgcgtcccc cttggtcaaa ttgggtatac ccatttgggc ctagtctagc      4680
cggcatggcg cattacagca atacgcaatt taaatgcgcc tagcgcattt tcccgacctt      4740
aatgcgcctc gcgctgtagc ctcacgccca catatgtgct aatgtggtta cgtgtatttt      4800
atggaggtta tccaatgagc cgcctgacaa tcgacatgac ggaccagcag caccagagcc      4860
tgaaagccct ggccgccttg cagggcaaga ccattaagca atacgccctc gaacgtctgt      4920
tccccggtga cgctgatgcc gatcaggcat ggcaggaact gaaaaccatg ctggggaacc      4980
gcatcaacga tgggcttgcc ggcaaggtgt ccaccaagag cgtcggcgaa attcttgatg      5040
aagaactcag cggggatcgc gcttgacggc ctacatcctc acggctgagg ccgaagccga      5100
tctacgcggc atcatccgct acacgcgccg ggagtggggc gcggcgcagg tgcgccgcta      5160
tatcgctaag ctggaacagg gcatagccag gcttgccgcc ggcgaaggcc cgtttaagga      5220
catgagcgaa ctcttttccccg cgctgcggat ggcccgctgc gaacaccact acgttttttg      5280
cctgccgcgt gcgggcgaac ccgcgttggt cgtggcgatc ctgcatgagc gcatggacct      5340
catgacgcga cttgccgaca ggctcaaggg ctgatttcag ccgctaaaaa tcgcgccact      5400
cacaacgtcc tgatggcgta cttacccaaa gaacagctag gagaatcatt tatgctcagc      5460
acacttccac aagctcatgc aactttcttg aaccgcatcc gcgatgcggt cgcttccgat      5520
gttcgcttcc gcgctcttct gatcggcggc tcttacgttc acggaggact cgatgagcac      5580
tccgatttgg atttcgacat cgttgttgag gacaactgct acgcagatgt cttgtctaca      5640
cgcaaggatt ttgccgaggc actgcccggc ttcctcaacg cgataagctg gctggatcct      5700
ctacgccgga cgcatcgtgg ccggcatcac cggcgccaca ggtgcggttg ctggcgccta      5760
tatcgccgac atcaccgatg gggaagatcg ggctcgccac ttcgggctca tgagcgcttg      5820
tttcggcgtg ggtatggtgg caggccccgt ggccggggga ctgttgggcg ccatctcctt      5880
gcatgcacca ttccttgcgg cggcggtgct caacggcctc aacctactac tgggctgctt      5940
cctaatgcag gagtcgcata agggagagcg tcgaccgatg cccttgagag ccttcaaccc      6000
agtcagctcc ttccggtggg cgcggggcat gactatcgtc gccgcactta tgactgtctt      6060
ctttatcatg caactcgtag acaggtgcc ggcagcgctc tgggtcattt tcggcgagga       6120
ccgctttcgc tggagcgcga cgatgatcgg cctgtcgctt gcggtattcg gaatcttgca      6180
cgccctcgct caagccttcg tcactggtcc cgccaccaaa cgtttcggcg agaagcaggc      6240
cattatcgcc ggcatggcgg ccgacgcgct gggctacgtc ttgctggcgt cgcgacgcg       6300 aggctggatg gccttcccca ttatgattct tctcgcttcc ggcggcatcg ggatgcccgc      6360
gttgcaggcc atgctgtcca ggcaggtaga tgacgaccat cagggacagc ttcaaggatc      6420
gctcgcggct cttaccagcc taacttcgat cattggaccg ctgatcgtca cggcgattta      6480
tgccgcctcg cgagcacat ggaacggggtt ggcatggatt gtaggcgccg ccctataccct    6540 tgtctgcctc ccgcgttgc gtcgcggtgc atggagccgg gccacctcga cctgaatgga     6600
```

```
agccggcggc acctcgctaa cggattcacc actccaagaa ttggagccaa tcaattcttg    6660
cggagaactg tgaatgcgca aaccaaccct tggcagaaca tatccatcgc gtccgccatc    6720
tccagcagcc gcacgcggcg catctcgggc agcgttgggt cctggccacg ggtgcgcatg    6780
atcgtgctcc tgtcgttgag gacccggcta ggctggcggg gttgccttac tggttagcag    6840
aatgaatcac cgatacgcga gcgaacgtga agcgactgct gctgcaaaac gtctgcgacc    6900
tgagcaacaa catgaatggt cttcggtttc cgtgtttcgt aaagtctgga aacgcggaag    6960
tcagcgccct gcaccattat gttccggatc tgcatcgcag gatgctgctg gctaccctgt    7020
ggaacaccta catctgtatt aacgaagcgc tggcattgac cctgagtgat ttttctctgg    7080
tcccgccgca tccataccgc cagttgttta ccctcacaac gttccagtaa ccggcatgt     7140 tcatcatcag taacccgtat cgtgagcatc ctctctcgtt tcatcggtat cattacccc     7200 atgaacagaa atccccctta cacggaggca tcagtgacca aacaggaaaa aaccgccctt    7260
aacatggccc gctttatcag aagccagaca ttaacgcttc tggagaaact caacgagctg    7320
gacgcggatg aacaggcaga catctgtgaa tcgcttcacg accacgctga tgagctttac    7380
cgcagctgcc tcgcgcgttt cggtgatgac ggtgaaaacc tctgacacat gcagctcccg    7440
gagacggtca cagcttgtct gtaagcggat gccgggagca gacaagcccg tcagggcgcg    7500
tcagcgggtg ttggcgggtg tcggggcgca gccatgaccc agtcacgtag cgatagcgga    7560
gtgtatactg gcttaactat gcggcatcag agcagattgt actgagagtg cacca         7615
```

<210> SEQ ID NO 10
<211> LENGTH: 4
<212> TYPE: PRT
<213> ORGANISM: CG12

<400> SEQUENCE: 10

Ala Ala Glu Ile
1

<210> SEQ ID NO 11
<211> LENGTH: 73
<212> TYPE: PRT
<213> ORGANISM: Artificial Sequence
<220> FEATURE:
<223> OTHER INFORMATION: Original amino acid sequence obtained from
      cDNA. Current sumitted sequence maximized for expression in E.
      coli.
<220> FEATURE:
<221> NAME/KEY: misc_feature
<223> OTHER INFORMATION: Original amino acid sequence obtained from
      cDNA. Current sumitted sequence maximized for expression in E.
      coli.

<400> SEQUENCE: 11

Met Ala Ala Glu Ile Cys Pro Ser Phe Gln Arg Val Ile Glu Thr Leu
1               5                   10                  15

Leu Met Asp Thr Pro Ser Ser Tyr Glu Ala Ala Met Glu Leu Phe Ser
            20                  25                  30

Pro Asp Gln Asp Met Arg Glu Ala Gly Ala Gln Leu Lys Lys Leu Val
        35                  40                  45

Asp Thr Leu Pro Gln Lys Pro Arg Glu Ser Ile Lys Leu Met Glu
    50                  55                  60

Lys Ile Ala Gln Ser Ser Leu Cys Asn
65                  70

METHODS FOR THE PRODUCTION OF PURIFIED RECOMBINANT HUMAN UTEROGLOBIN FOR THE TREATMENT OF INFLAMMATORY AND FIBROTIC CONDITIONS

This application is a continuation-in-part of U.S. Ser. No. 08/864,357, filed May 28, 1997, now U.S. Pat. No. 6,255,281, issued Jul. 3, 2001, the disclosure of which is incorporated herein by reference.

FIELD OF THE INVENTION

The present invention relates generally to the production of recombinant human uteroglobin (rhUG) which has use as a therapeutic in the treatment of inflammation and fibrotic diseases, has immunomodulatory effects, and regulates smooth muscle contraction. More particularly, the invention provides processes, including broadly the steps of bacterial expression and protein purification, for the scaled-up production of rhUG according to current Good Manufacturing Practices (cGMP). The invention further provides analytical assays for evaluating the relative strength of in vivo biological activity of rhUG produced via the scaled-up cGMP processes.

BACKGROUND OF THE INVENTION

Therapeutic Uses of Recombinant Uteroglobin

The search for improved therapeutic agents for the treatment of inflammatory, as well as fibrotic diseases, has received much attention in recent years. Neonatal Respiratory Distress Syndrome (RDS), a lung surfactant deficiency disease, is a condition of particular interest in that it is one of the major causes of mortality in premature neonates. While introduction of surfactant therapy dramatically improves survival of RDS patients, the development of chronic inflammatory and fibrotic disease in a significant percentage of this patient population is a major problem. Likewise, glomerular nephropathy and renal fibrosis leads to end stage renal failure when patients' kidneys become blocked and no longer filter the blood. Many forms of glomerular nephropathy and renal fibrosis is characterized by fibronectin deposits. In both diseases, fibronectin and collagen deposition and fibrosis render the organ nonfunctional, and eventually, unable to support life. Thus, these patients require chronic hemodialysis or kidney transplantation.

Recombinant human UG is a protein with beneficial anti-inflammatory, anti-fibrotic, anti-tumor, respiratory and immunomodulatory properties that is under development as a therapeutic agent in several clinical indications. Recombinant human UG is useful for the treatment of conditions characterized by a deficiency of UG. It is especially adapted for the treatment of pulmonary inflammatory conditions, for example neonatal respiratory distress syndrome (RDS) and bronchopulmonary dysplasia (BPD); for the treatment of conditions characterized by an elevation in local serum $PLA_2$ activity, such as adult RDS (ARDS), septic shock, pancreatitis, collagen vascular diseases, rheumatoid arthritis, acute renal failure, and autoimmune uveitis; for the treatment of conditions characterized by local elevations in $PLA_2$ activity, such as neonatal RDS/BPD, ARDS, rheumatoid arthritis, asthma, peritonitis, glomerulopathies, including hereditary Fn-deposit glomerulonephritis, and autoimmune uveitis; for the treatment of fibrotic conditions where deposition of fibronectin is a causative factor e.g., idiopathic pulmonary fibrosis, bleomycin lung, and cystic fibrosis and glomerular nephropathy, particularly familial glomerulerophathy, characterized by Fn deposits in the kidneys, which ultimately lead to renal failure, can also be treated with exogenous UG; and to methods for treating or preventing an inflammatory or fibrotic condition characterized by a deficiency of endogenous functional UG, by administering a compensating amount of rhUG.

RhUG is useful for inhibiting cellular adhesion to fibronectin, inhibits inflammatory cell and fibroblast migration on already deposited fibronectin, and inhibits the interaction between a cell and an extracellular matrix protein and/or membrane bound protein. RhUG is also especially useful for improving and/or normalizing lung function, pulmonary compliance, blood oxygenation, and/or blood pH. RhUG is particularly useful in the regulation of smooth muscle concentration in various organ systems including the respiratory system, the digestive system, the circulatory system, the reproductive system, and the urinary system. RhUG may also be used as well to regulate or reduce vascular permeability, to inhibit the migration of vascular endothelial cells and angiogenesis, and to prevent angiogenesis. Intratracheal rhUG may be used as a stem cell factor to increase lymphocyte production and/or decrease polymorphonuclear leukocyte proliferation in the long term. RhUG increases the concentration of circulating lymphocytes and/or cytotoxic T cells while decreasing the concentration of circulating polymorphonuclear leukocyte proliferation, which is especially useful for patients suffering from an autoimmune disease or allergy. Intravenous rhUG may be used as well to suppress ATP metabolism in circulating lymphocytes and to increase ATP metabolism in activated neutrophil, monocytes, macrophages, and NK cells in the short term.

Prior Art Methods for the Production of Recombinant Human Uteroglobin

There are several published methods for expressing rhUG and for purifying either native or recombinant uteroglobin, or urine protein-1, in microgram to milligram quantities for research purposes (Mantile, 1993; Miele, 1992; Singh, 1987; Jackson, 1989; Anderson, 1994; Umland, 1994; Aoki, 1996). These methods are quite varied but none are well suited to large-scale production of a protein and none address the regulatory issues required of a process for production of a pharmaceutical. Furthermore, the biological activities of these various preparations are not necessarily equivalent. For example, Nieto (1997) reported that native rabbit uteroglobin loses some of its progesterone activity upon lyophilization, while Miele and Mantile use repeated size exclusion chromatography steps and multiple lyophilizations as concentration steps during their purification process. However, end users would greatly prefer a ready-to-use product over a lyophilized product since the percentage of aggregates of rhUG increases with both lyophilization and repeated freeze thaw cycles. High levels of aggregation can adversely affect the biological activity, change the immunogenicity, or alter the potency of the final drug product. Under FDA guidelines undesirable aggregates constitute an impurity, entire lots of drug product may be rejected on the basis of high levels of aggregate within the drug product.

Problems in Development of Recombinant Therapeutics

The production of the recombinant protein-based drug substances involves the development of several processes that adhere to the guidelines set forth by the United States Food and Drug Administration (FDA) referred to as current Good Manufacturing Practices (cGMP). A process that adheres to the FDA's cGMP guidelines is compliant with cGMP. In order to sell a pharmaceutical composition or drug product in the U.S. and elsewhere, it is necessary to produce the drug product using a cGMP process.

The clinical development of a recombinant protein as a drug substance, as well as the sales and use of protein drugs, require a well-characterized and reproducible production process for the drug substance as well as a detailed characterization of that drug substance.

Recombinant proteins represent a particular challenge since their activity is dependent not only upon amino acid composition but also upon the conformation of the protein. The conformation of a protein is the overall three-dimensional structure of the protein which may be characterized on four levels. The first level is its primary structure or amino acid sequence. The second level is the protein's secondary structure and is the pattern of organization associated with short stretches of about 6–30 amino acids in the protein which form local stable structural regions such as alpha helices, beta sheets, and omega loops. The third level, tertiary structure consists of the groupings of secondary structures into units or domains within a single contiguous stretch of amino acids, representing a protein or peptide monomer. The four helical bundle or fibronectin Type III repeat are examples of tertiary structures. The fourth level, quaternary structure is present when two or more individual peptide or protein monomers combine, either covalently or non-covalently, to form a single functional unit.

Recombinant proteins present a further challenge since activity is also dependent upon surface characteristics in which charge and hydrophobic character, in addition to shape, contribute significantly to the ability of a recombinant protein to interact specifically with other biological and chemical substances in a physiological environment. Isoforms of a protein consist of small variations in conformation, surface charge and/or hydrophobic character. These variations may result from changes in temperature, or from interactions with chemicals, salts, or other biological molecules (e.g., proteins, carbohydrates, lipids, nucleic acids, etc.) in the surrounding environment, or from actual chemical modifications to individual amino acids in the protein. Different isoforms of a protein can be detected by high-resolution analytical methods such as hydrophobic interaction HPLC, mass spectrometry, capillary electrophoresis, peptide mapping, isoelectric focusing, and two-dimensional electrophoresis.

The physical form and conformation of a recombinant protein drug can be strongly influenced by the expression system in which it is produced, as well as by the process through which it is purified for use as a drug substance, for example. Likewise, the resulting isoform or isoforms of the recombinant protein product can also be strongly influenced by the expression system and process through which it is produced. The biological activity of a protein is highly dependent upon its conformation and isoform(s), not just its chemical composition. For example, a protein may be partially or completely denatured by exposure to high or low temperatures and rendered biologically inactive, yet it still retains the same sequence of amino acids. Therefore, the biological activity of a recombinant protein is dependent not only on its chemical composition, but also upon the process through which it is expressed, purified, formulated and even packaged.

Drug substances or products often have extra components in addition to the biologically active compound and its vehicle or carrier. These components are derived from the raw materials from which the drug was produced or from materials introduced as part of the purification, formulation, or final packaging processes. The drug substance is defined as the final form of purified bulk drug while the drug product is the final packaged formulation of the drug substance (e.g., the product used in the patient.) These extra components of the drug substance or product are considered impurities or contaminants and may have unintended or undesirable biological activities of their own, either alone or in combination with the drug itself. Contaminants may be defined as components that are not derived from the drug itself while impurities may be defined as components that contain some element of the drug itself (e.g., fragments, variations, isoforms, enantiomers, aggregates, etc.). Thus, the drug production process is important not only because it determines the characteristics of the drug itself, but also because it determines the level and nature of contaminants and impurities in the drug substance and drug product. It is essential, therefore, to carefully define the process in order to maintain consistent and reproducible biological activity, in vivo, of a drug substance, drug product, or pharmaceutical composition. Thus, the process through which a recombinant protein drug is produced should be sufficiently well-characterized so that it is capable of complying with pharmaceutical production regulatory guidelines in order to be commercially viable, since non-compliance results in a product that cannot be sold or used in the U.S and elsewhere.

Moreover, the biopharmaceutical production process must be sufficiently efficient and economical to be commercially viable. Purification methods that are used in the laboratory to produce small amounts of a protein for research purposes are not typically suitable for biopharmaceutical production. For example, a small scale method such as size exclusion chromatography often is not practical for larger scale production because the chromatography matrix would be crushed under its own weight in the size of column required for purification of even a few grams of protein. Furthermore, size exclusion chromatography always increases the volume of the sample, resulting in less manageable high volume purification intermediates that must be concentrated prior to the next step in the process. Therefore, it is highly desirable to avoid the use of size exclusion chromatography in a biopharmaceutical production process. Another technique frequently employed to preserve a protein pharmaceutical agent in a stable form is lyophilization. This process involves the simultaneous freeze-drying of a protein, converting it from a liquid form in which it is typically susceptible to degradation, to a dry powder form in which it can typically be stored for many months without losing biological activity. However, repeated freeze/thaw cycles increase the percentage of aggregates of rhUG, which may result in a significant change in biological activity.

OBJECTS OF THE INVENTION

It is a primary object of the invention to provide a bacterial expression system for the production of rhUG.

It is a further object of the invention to provide methods for the production of rhUG and the purification of human uteroglobin for substances suitable for use as a pharmaceutical substance.

It is still a further object of the invention to provide scaled-up production of rhUG conforming to cGMP standards.

A further and related object of the invention is to provide methods to measure biological activities of human UG in vitro.

It is still a further object of the invention to provide pharmaceutical preparations of human uteroglobin which are commercially viable.

A further and related object of the invention is to provide a method of producing rhUG research seed banks, master cell banks, and production cell banks.

SUMMARY OF THE INVENTION

The invention provides a bacterial expression system for the production of rhUG comprising a synthetic gene which codes for human UG, wherein the synthetic gene comprises SEQ ID NO: 1–4. The invention also provides a bacterial expression system for production of rhUG comprising a human cDNA sequence which codes for human UG wherein the gene further comprises Met-Ala-Ala at the N-terminus of the sequence.

The invention further provides a method of producing a rhUG research seed bank comprising: (a) inoculating onto a growth medium at least one colony of a bacterial strain comprising a rhUG expression system; (b) incubating the inoculated growth medium until a stationary phase is reached; (c) adding glycerol to the inoculated growth medium; (d) freezing the culture in aliquot portions; and (e) storing the frozen aliquot portions at a temperature below about −50 C.

The invention also provides a method of producing a rhUG master cell bank comprising: (a) inoculating a suitable incubating broth with an aliquot portion of a rhUG research seed bank; (b) incubating the inoculated broth; (c) adding a cryopreservative to the incubated broth to form a cryopreserved solution; (d) transferring a portion of the cryopreserved solution to a cryovial; and (e) storing the cryovial at a temperature below about −60 C.

The invention also provides a method of producing a rhUG production cell bank comprising: (a) inoculating a suitable incubating broth with an portion of a rhUG master cell bank; (b) incubating the inoculated broth; (c) adding a cryopreservative to the incubated broth to form a cryopreserved solution; (d) transferring a portion of the cryopreserved solution to a cryovial; and (e) storing the cryovial at a temperature below about −60 C.

The invention also provides a method of expressing rhUG comprising the steps of: (a) providing a production seed cell bank culture comprising an expression vector capable of expressing rhUG; (b) inoculating a broth medium with the production seed cell bank culture to form an inoculum; (c) incubating the inoculum formed in step b; (d) inoculating a large scale fermenter with the inoculum formed in step (c) to form a fermentation culture; (e) incubating the fermentation culture within the large scale fermenter; (f) adding an induction agent to the fermentation culture to induce the expression of rhUG; and (g) harvesting the fermentation culture after step (f).

The invention further provides a method of expressing rhUG comprising the steps of: (a) inoculating a large scale fermenter with an inoculum comprising an expression vector capable of expressing rhUG to form a fermentation culture; (b) incubating the fermentation culture within the large scale fermenter; (c) adding an induction agent to the fermentation culture to induce the expression of rhUG; and (d) harvesting the fermentation culture.

The invention further provides a method of purifying rhUG comprising the steps of: (a) providing a bacterial cell paste comprising bacterial cells capable of overexpressing rhUG; (b) lysing the bacterial cell paste to form a supernatant; (c) filtering the supernatant formed in step b through a first nominal molecular weight cut off (NMWCO) membrane to form a first permeate; (d) concentrating the first permeate formed in step (c) by use of a second NMWCO membrane to form a first concentrate; (e) loading the concentrated permeate formed in step (d) onto an anion exchange column to form a first eluate; (f) concentrating the first eluate formed in step (e) by use of a third NMWCO membrane to form a second concentrate; (g) loading the second permeate formed in step (f) onto a Hydroxyapatite (HA) column to form a second eluate; (h) separating host-derived proteins from the rhUG in the second eluate formed in step (g) to provide purified rhUG; and (i) recovering the purified rhUG formed in step (h).

The invention also provides a method of purifying rhUG comprising the steps of: (a) providing bacterial cells capable of overexpressing rhUG; (b) lysing the bacterial cells to form a supernatant liquid; (c) filtering the liquid through a molecular weight cut off (NMWCO) membrane; (d) loading the liquid onto an exchange column; (e) separating host-derived proteins from the rhUG to provide purified rhUG; and (f) recovering the purified rhUG.

The invention provides a method of producing a pharmaceutical grade rhUG drug substance comprising the steps of: (a) providing a bacterial expression system capable of expressing rhUG; (b) inoculating a fermenter with an inoculum comprising the bacterial expression system to form a fermentation culture; (c) adding an induction agent to the fermentation culture to induce the expression of rhUG by the bacterial expression system; (d) harvesting the rhUG expressed in step (c); and (e) purifying the rhUG harvested in step (d), wherein the purifying step comprises the use of at least one filter and at least one exhange column.

The invention provides an assay method for determining the potency of recombinant human uteroglobin in a sample which comprises: (a) contacting a sample containing recombinant human uterogloblin with phospholipase $A_2$, (b) introducing a radiolabeled substrate to said sample, (c) separating product from sample, and (d) determining level of cleavage.

The invention further provides a method for measuring in vitro the anti-inflammatory effect arising from inhibition or blocking of secretory phopsholipase $A_2$ enzymes by recombinant human uteroglobin, comprising: (a) contacting a sample containing recombinant human uterogloblin with phospholipase $A_2$, (b) introducing radiolabeled substrate to said sample, (c) separating product from sample, and (d) determining level of cleavage by scintillation counting.

The invention also provides an assay method for assaying for the inhibition of secretory phopsholipase $A_2$ activity by recombinant human uteroglobin, comprising: (a) contacting a sample containing recombinant human uterogloblin with phospholipase $A_2$, (b) introducing radiolabeled substrate to said sample, (c) separating product from sample, and (d) determining level of cleavage by scintillation counting.

The invention also provides an assay method for determining the potency of recombinant human uteroglobin in a sample which comprises: (a) contacting a sample containing recombinant human uterogloblin with phospholipase $A_2$, (b) introducing flourescently labeled substrate to said sample, (c) separating non-cleaved substrate from sample, and (d) determining amount of cleaved substrate by flourescence.

The invention provides a method for measuring in vitro the binding of recombinant human uteroglobin to fibronectin, comprising: (a) contacting a recombinant fragment of human fibronectin with a recombinant human CC10-HRP conjugate, (b) visualizing the assay to determine binding of recombinant human uteroglobin to the fibronectin fragment.

The invention also provides a pharmaceutical composition comprising a purified recombinant human uteroglobin and a pharmaceutically acceptable carrier or diluent.

BRIEF DESCRIPTION OF THE DRAWINGS

The invention will now be described in more detail, with reference to the accompanying drawings, in which.

10–20% Tricine Gel: Lanes are from left to right: Lane 1: Size Standard Lane 2: Uninduced bacterial lysate, Lane 3: Induced bacterial lysate.

Figure 3:
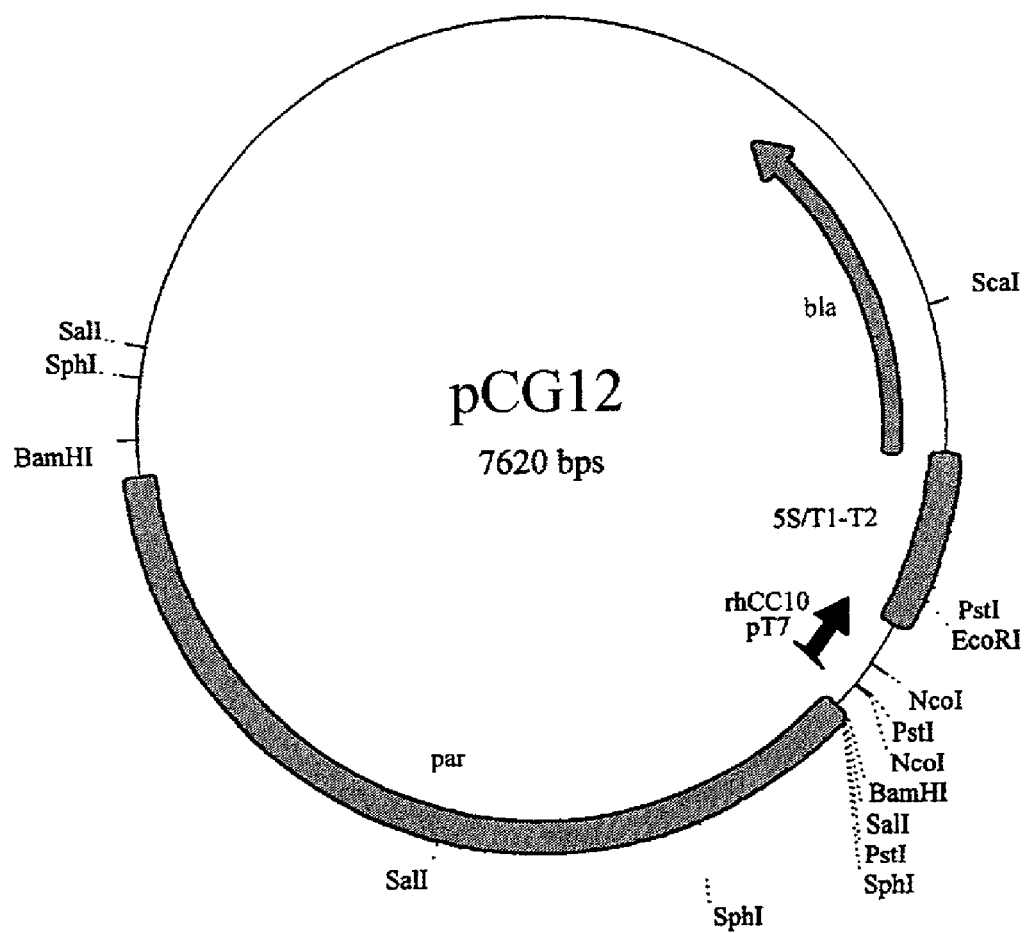

FIG. 3 shows the genetic map of plasmid pCG12.

Figure 4:
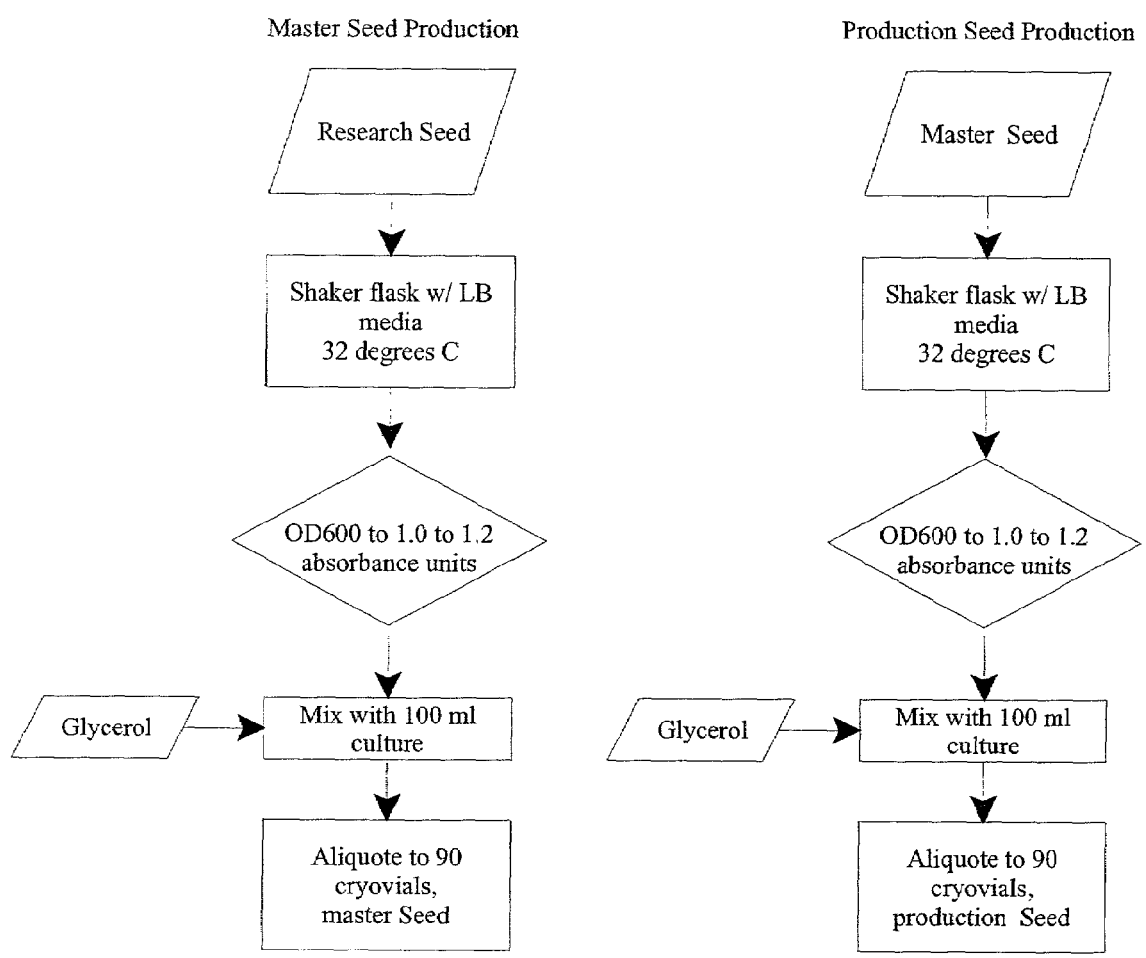

FIG. 4 shows a flowchart of master and production seed cell banking process.

Figure 5:
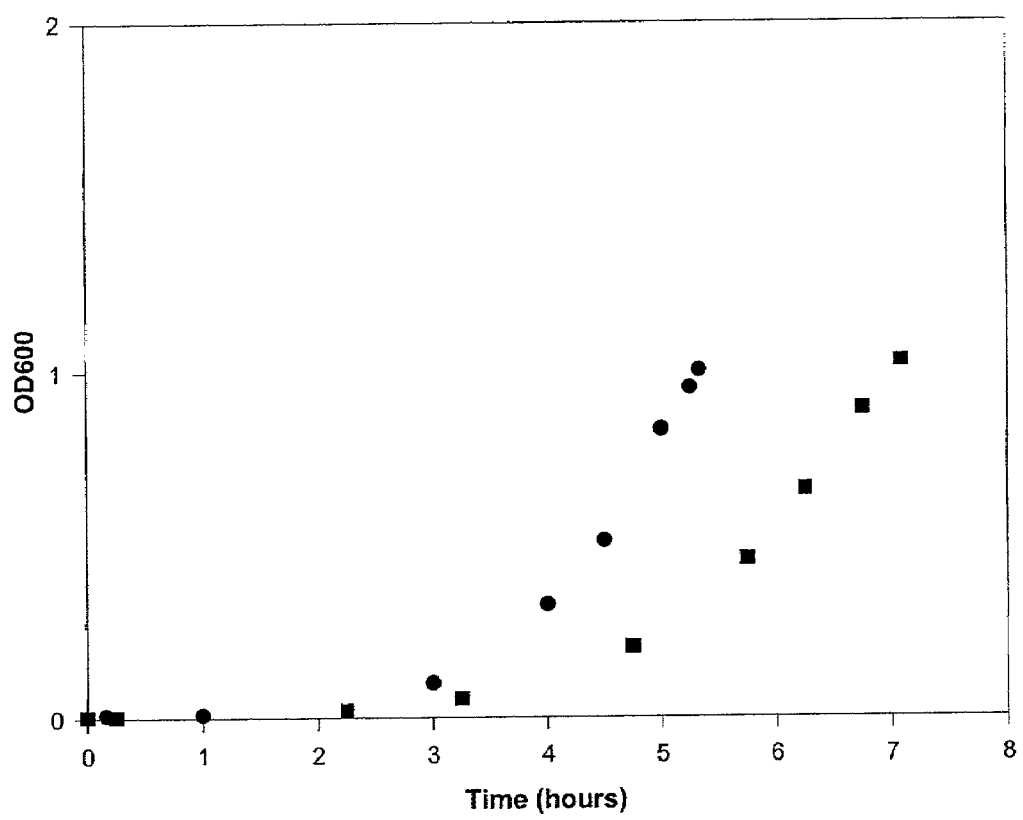

FIG. 5 shows growth curves of bacterial cultures from which master (labeled ●) and production (labeled ■) seed cell banks were derived.

Cell growth was followed by Optical Density at 600 nm for both the Master (1) and Production (n) seeds.

Figure 6:
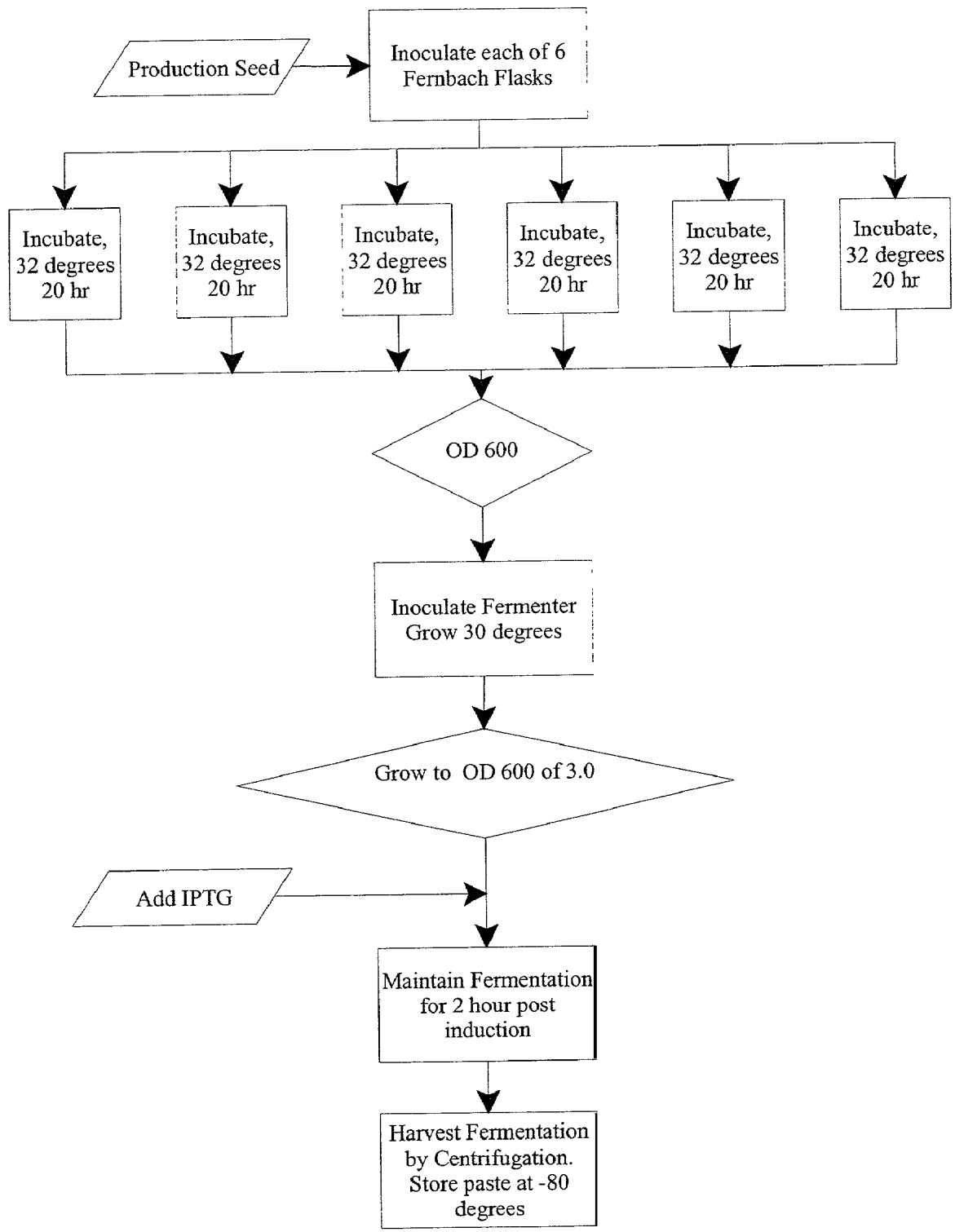

FIG. 6 shows a flowchart of fermentation process for rhUG expression.

Figure 7:
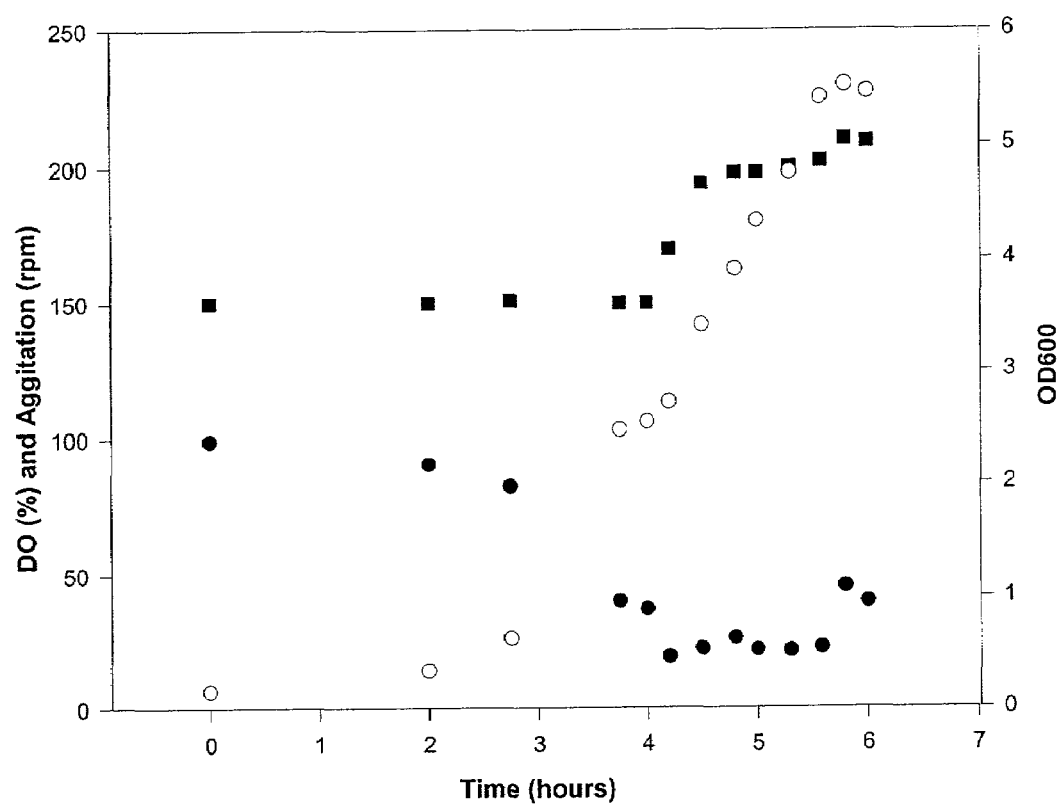

FIG. 7 shows a growth curve of fermentation culture.

Culture growth was followed by the OD at 600 nm (O), aeration (DO, ●) was followed by a dissolved oxygen probe, and agitation (■) was followed as a function of the rpm's.

Figure 8:
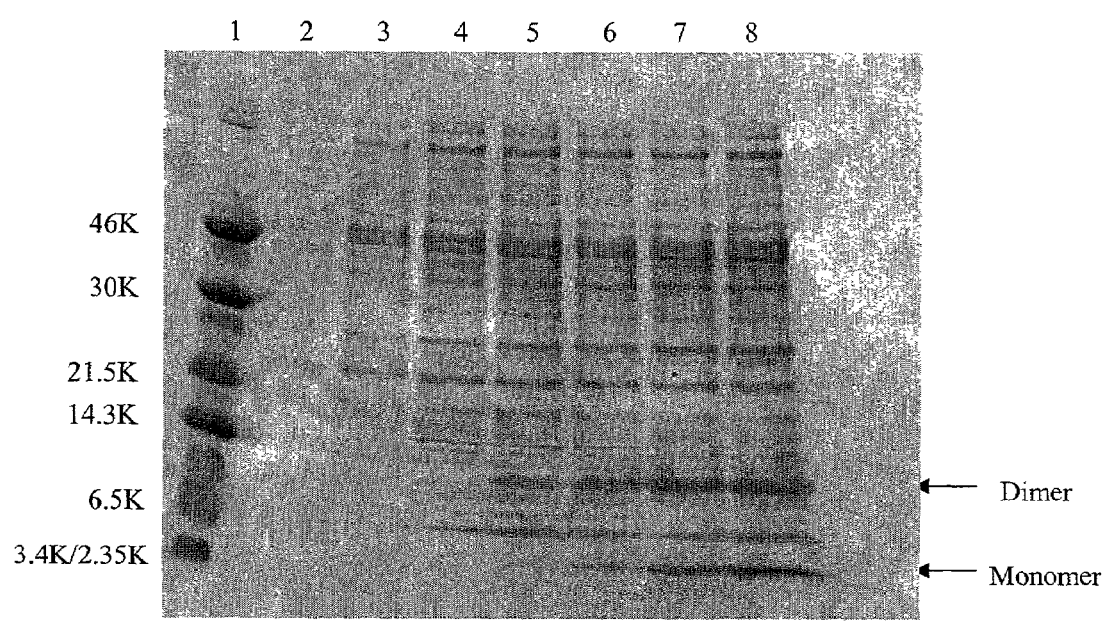

FIG. 8 shows SDS-page analysis of rhUG expression during fermentation.

10–20% Tricine gel. Lanes are from left to right, Lane 1, Rainbow Standard; the fermentation samples taken at the indicated times, post-induction: lane 2, 3.8 hr; lane 4.0 hr; lane 4, 4.2 hr; lane 5, 4.5 hr; lane 6, 5.0 hr; lane 7, 5.6 hr; and lane 8, 6 hr.

FIGS. 9a and b show flow diagram of purification scheme, and minor variations thereof.

Figure 10:
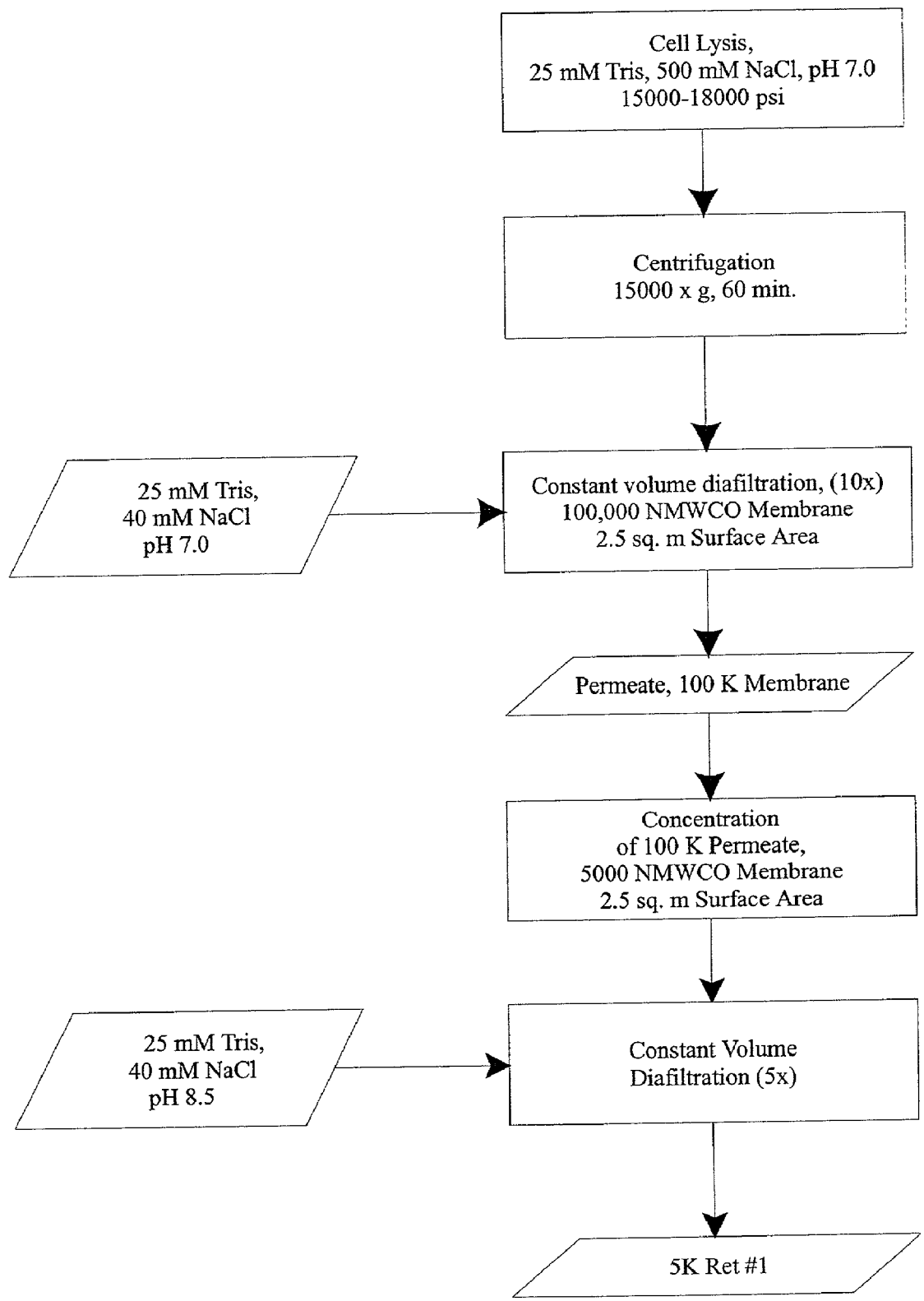

FIG. 10 shows a detailed flow diagram of the initial TFF and diafiltration.

Figure 11A:
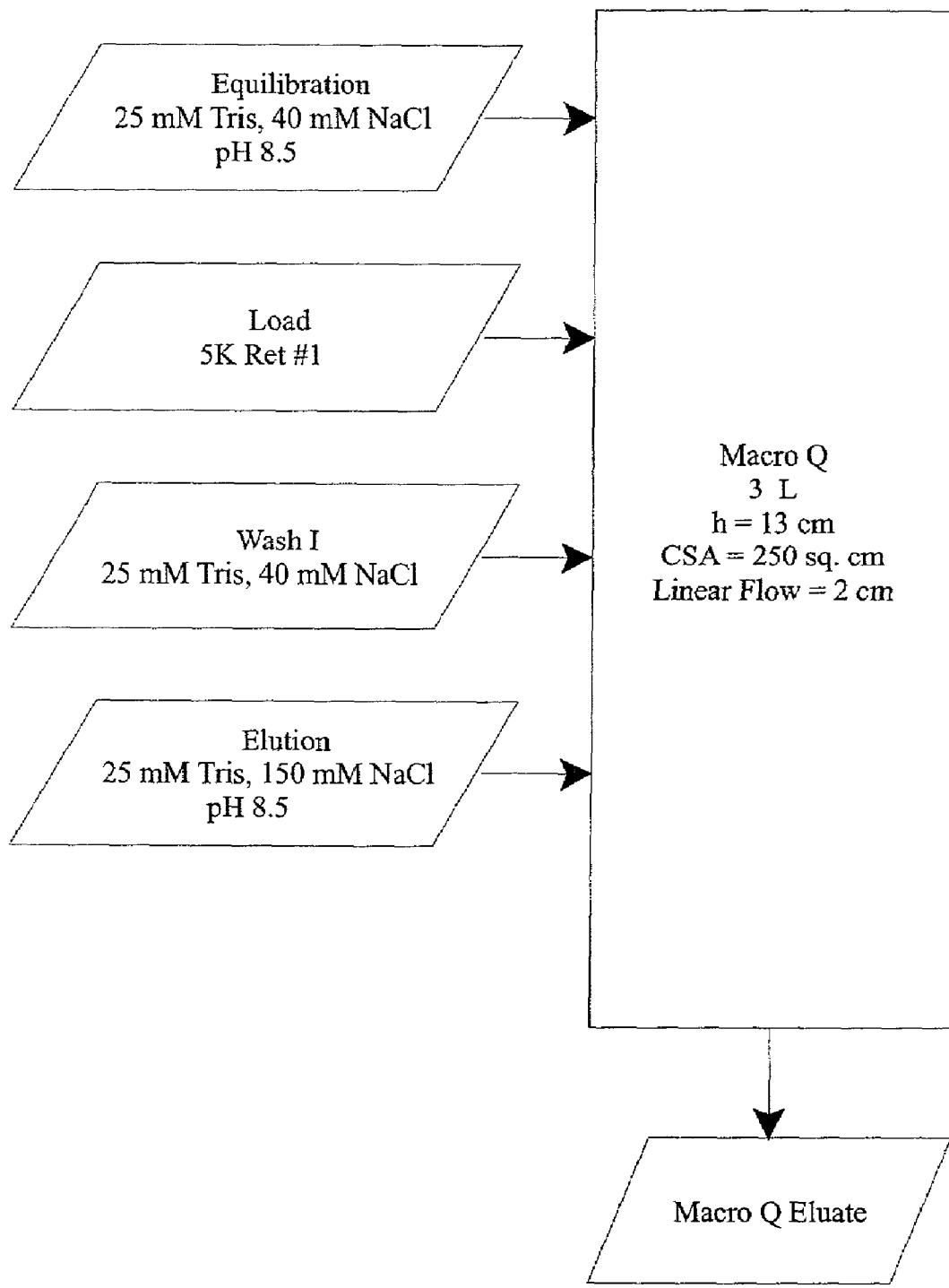

FIG. 11a shows a detailed flow diagram of the Macro Q anion exchange chromatography step.

Figure 11B:
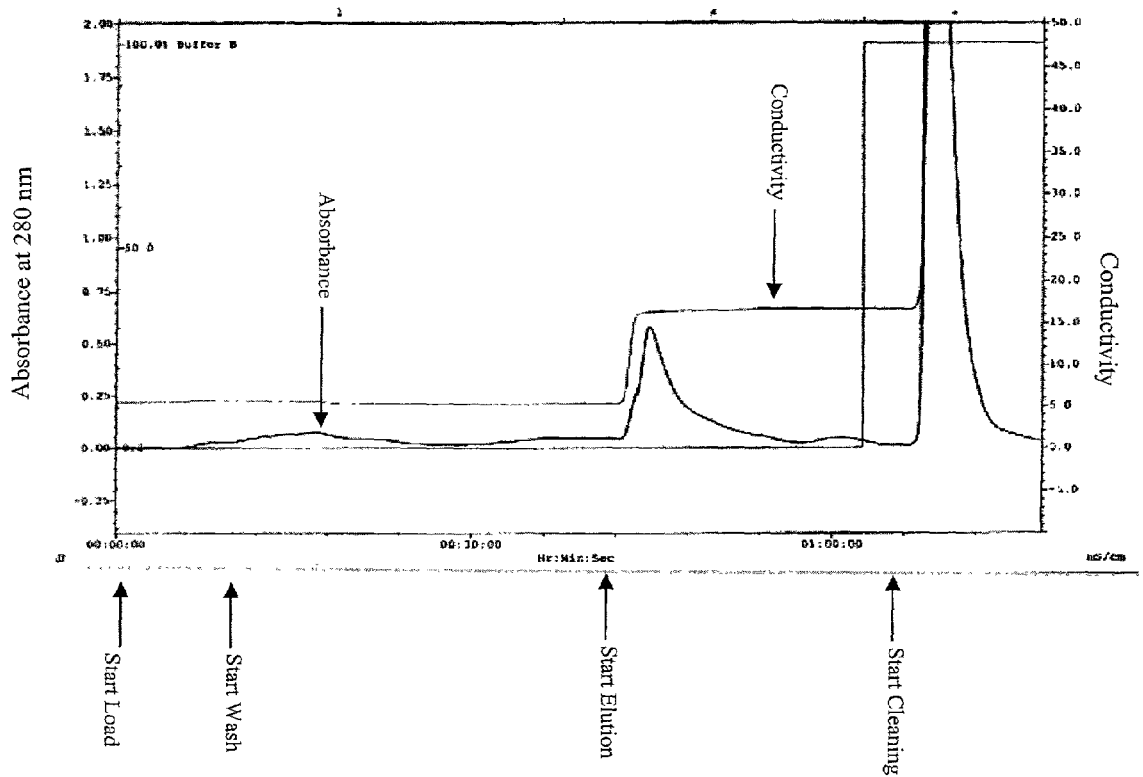

FIG. 11b shows a representative chromatogram of the Macro Q anion exchange chromatography step.

Figure 12:
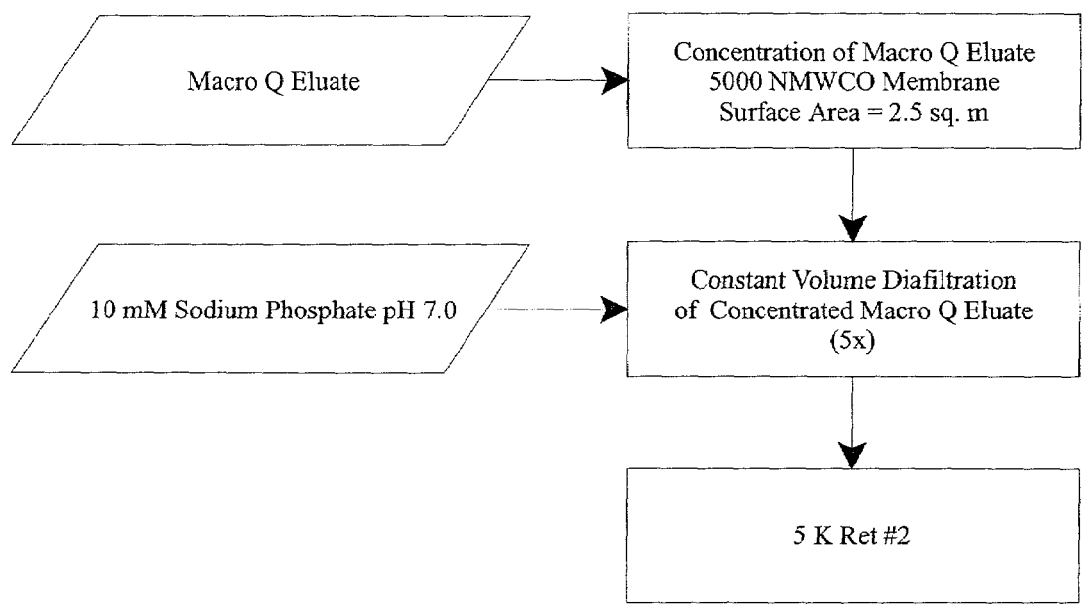

FIG. 12 shows a detailed flow diagram of the second concentration/diafiltration step.

Figure 13A:
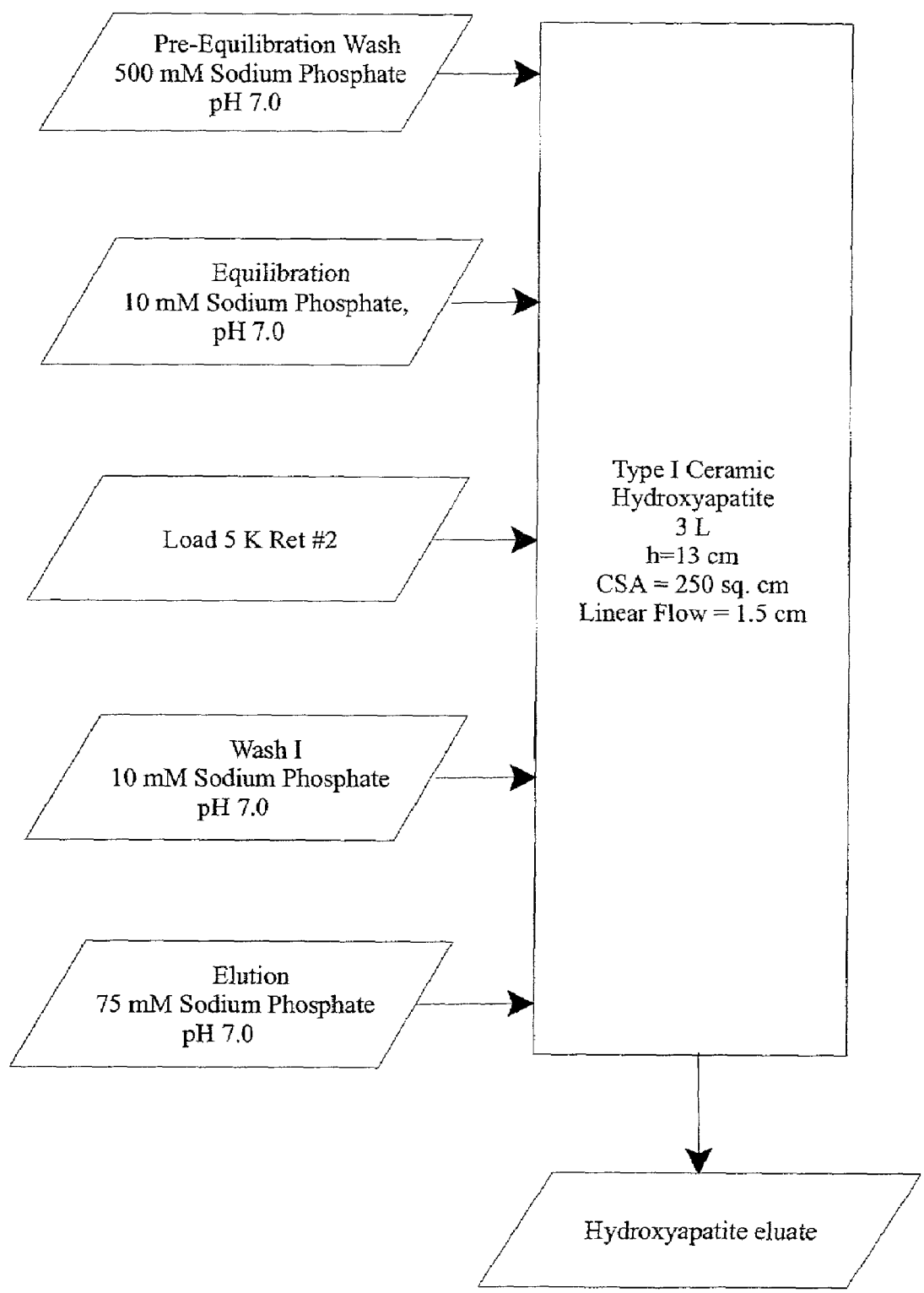

FIG. 13a shows a detailed flow diagram of the hydroxyapatite chromatography step.

Figure 13B:
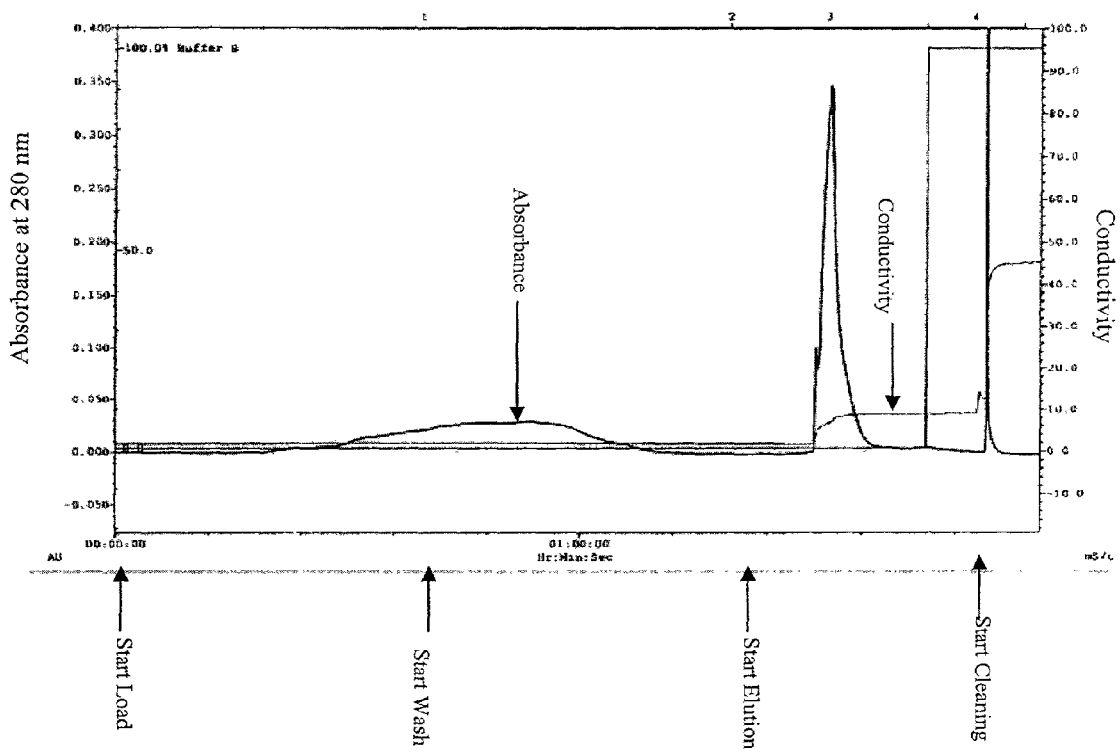

FIG. 13b shows a representative chromatogram of the hydroxyapatite chromatography step.

Figure 14A:
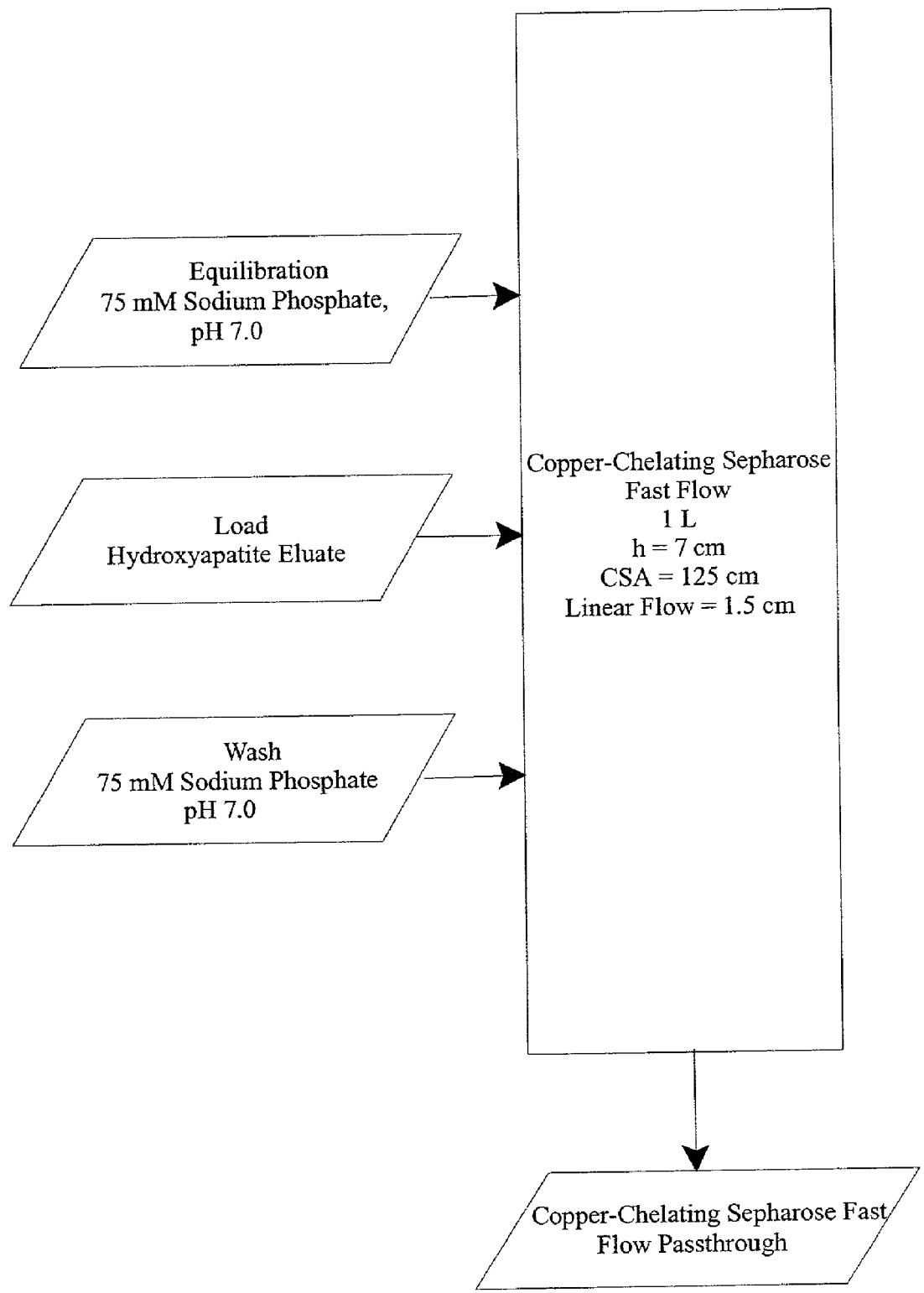

FIG. 14a shows a detailed flow diagram of the copper chelation chromatography step.

Figure 14B:
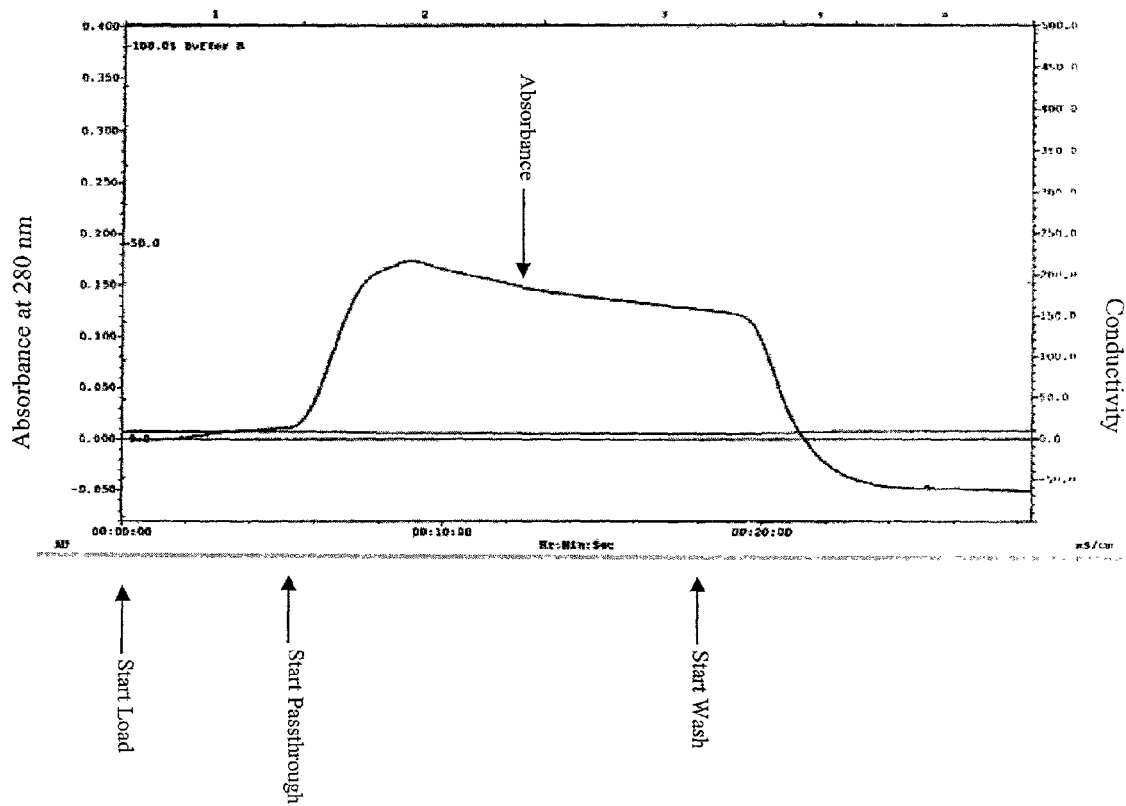

FIG. 14b shows a representative chromatogram of the copper chelation chromatography step.

Figure 15:
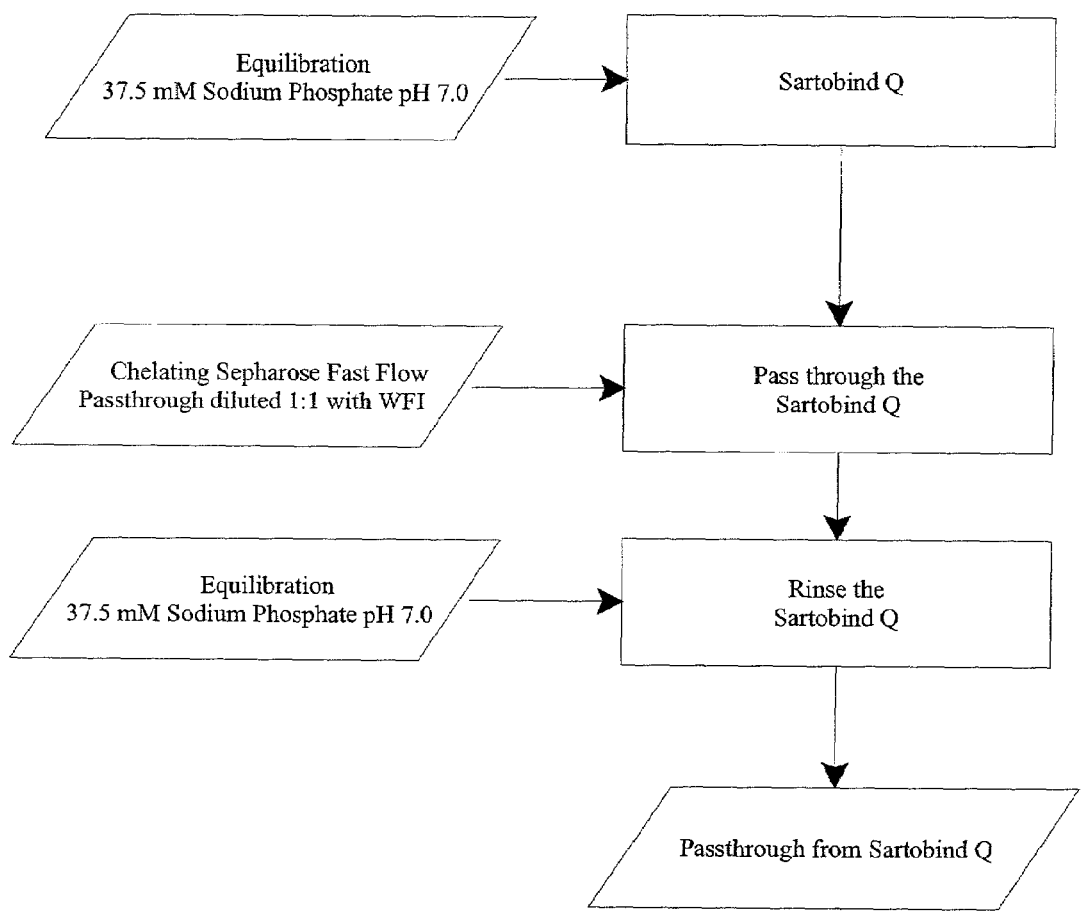
Figure 16:
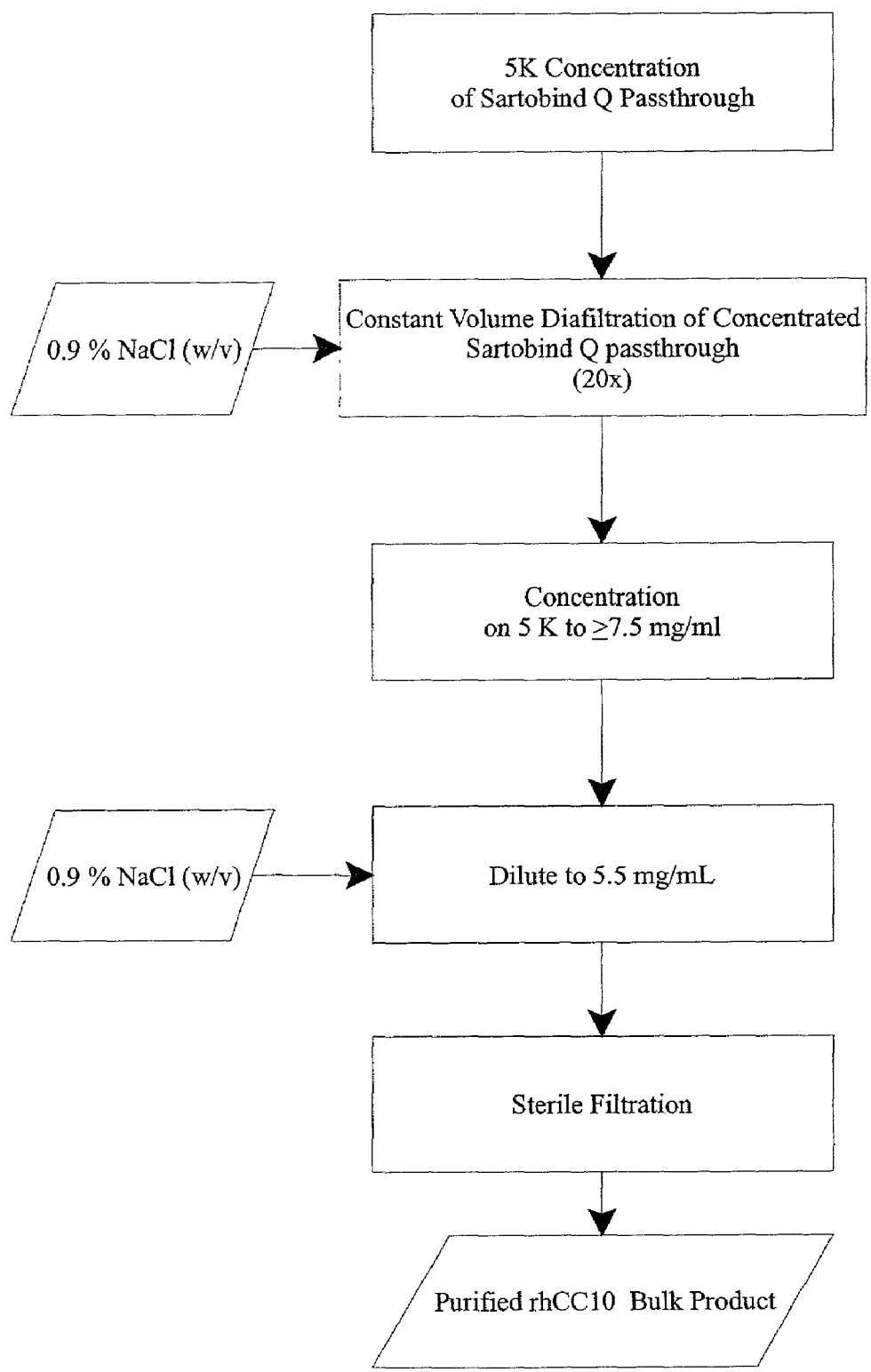

FIG. 15 shows a detailed flow diagram of a filtration step with SARTOBIND® (a filtration membrane) Q and third concentration/diafiltration step FIG. 16 shows a detailed flow diagram of final diafiltration and formulation.

Figure 17:
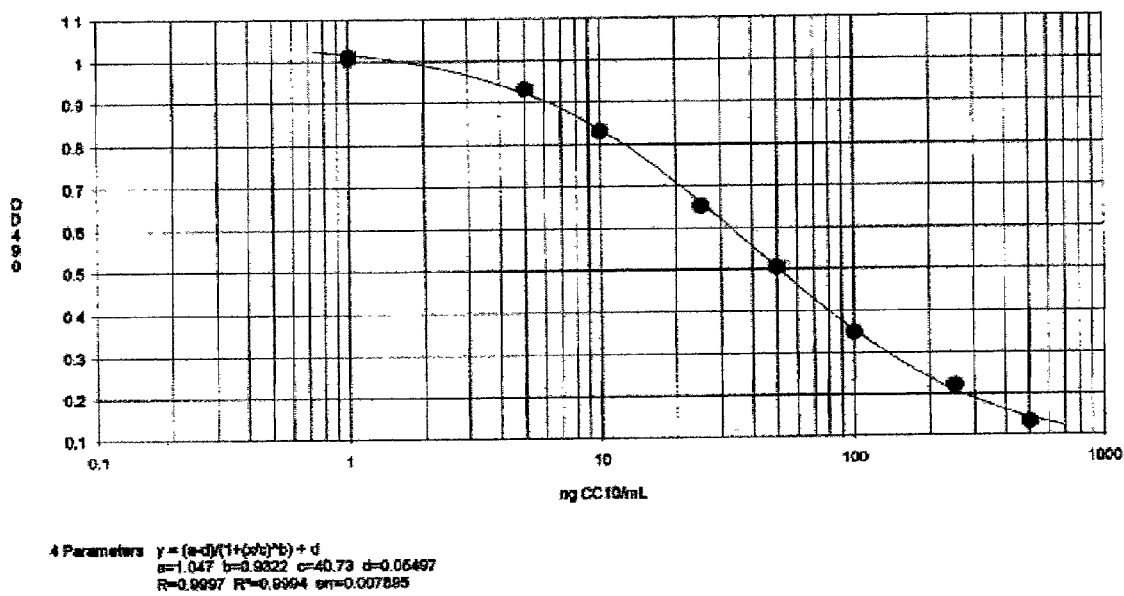

FIG. 17 shows a standard curve for competitive ELISA for UG.

Figure 18:
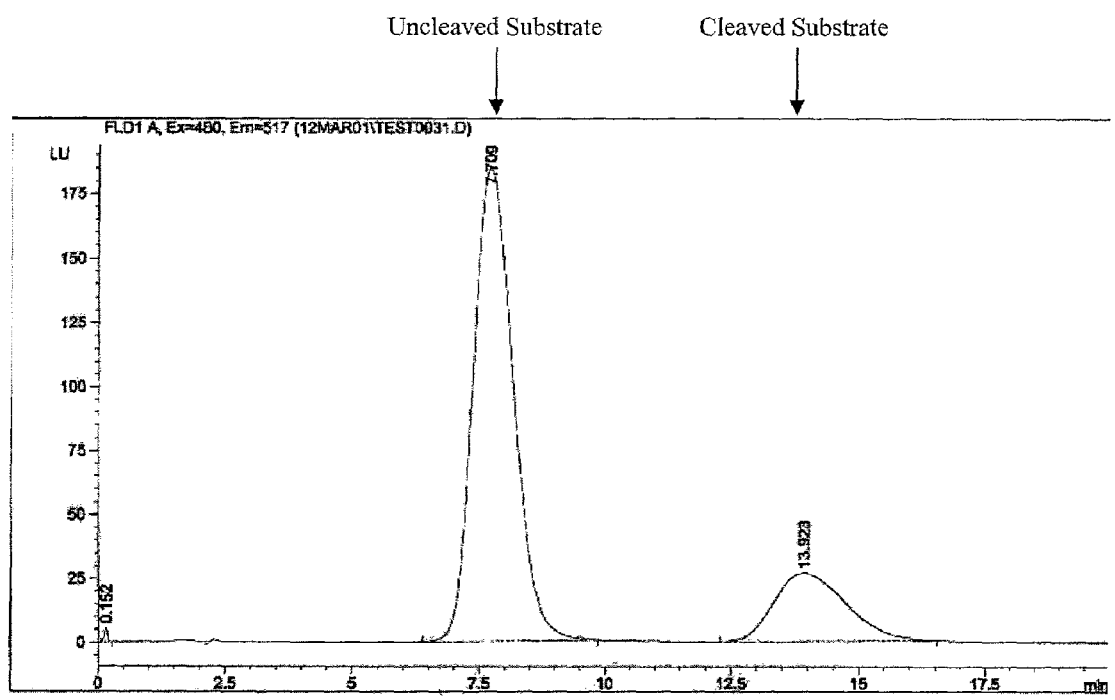

FIG. 18 shows a chromatogram of SPLA2 assay.

Figure 19:
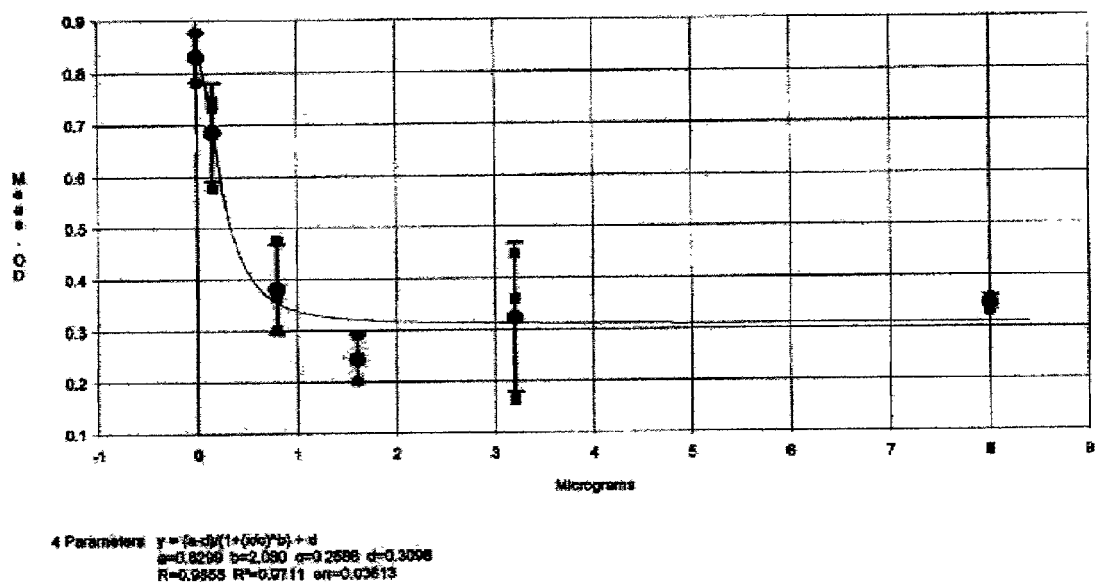

FIG. 19 shows a standard curve for fibronectin binding assay.

Figure 20A:
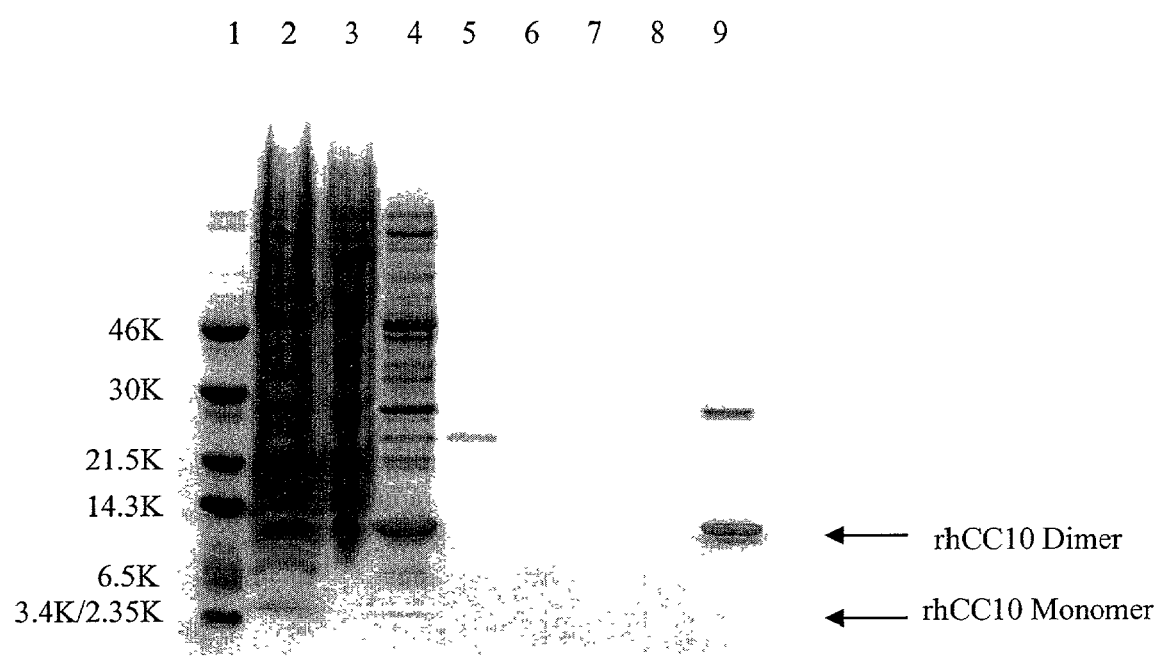

FIG. 20a show assessment of purification steps by SDS-PAGE.

10–20% Tricine gel, samples are, from left to right: lane 1, Rainbow Standard; lane 2, Crude lysate; lane 3, 100 K Retentate; lane 4, 5 K Ret; Lane 5, #1, Macro Q Passthrough; lane 6, Macro Q Wash I#1; lane 7, Macro Q Wash I#2; lane 8, Macro Q Wash I#3; and lane 9, Macro Q eluate.

Figure 20B:
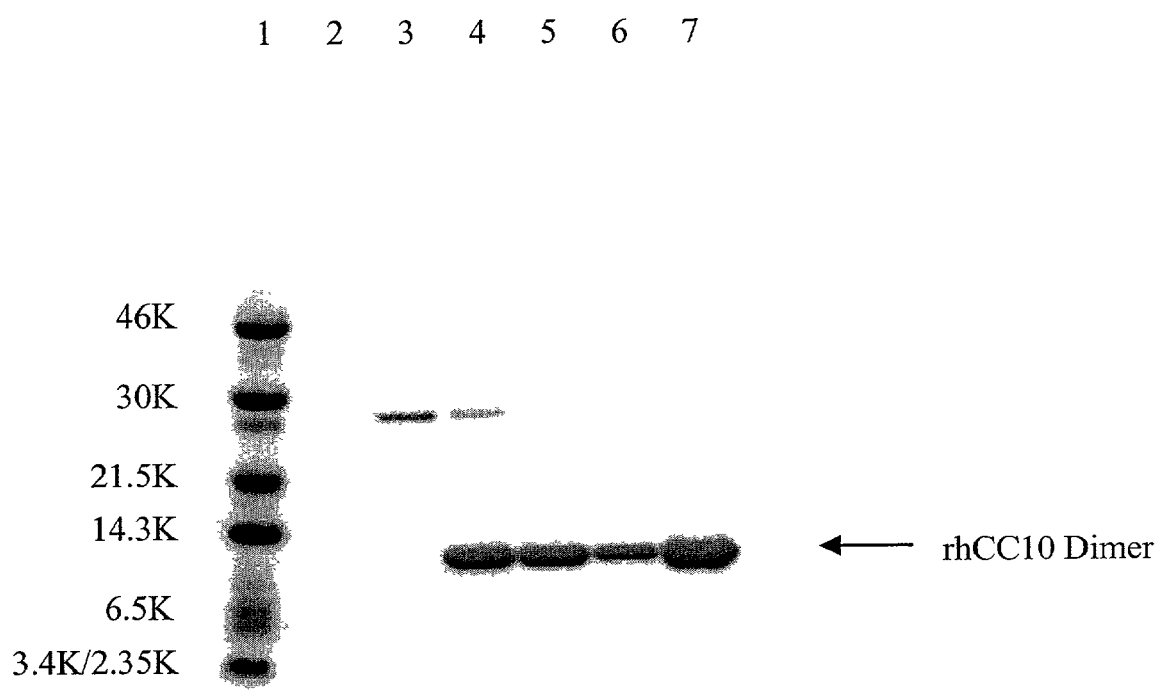

FIG. 20b: Assessment of Purification Steps by SDS-PAGE.

10–20% Tricine gel, samples are, from left to right: lane 1, Rainbow Standard; lane 2, Hydroxyapatite Passthrough; lane 3, Hydroxyapatite Wash I; lane 4, Hydroxyapatite eluate; lane 5, Copper CSFF Passthrough; lane 6, SARTOBIND® Q Passthrough; lane 7, Purified rhCC10 Bulk.

Figure 21:
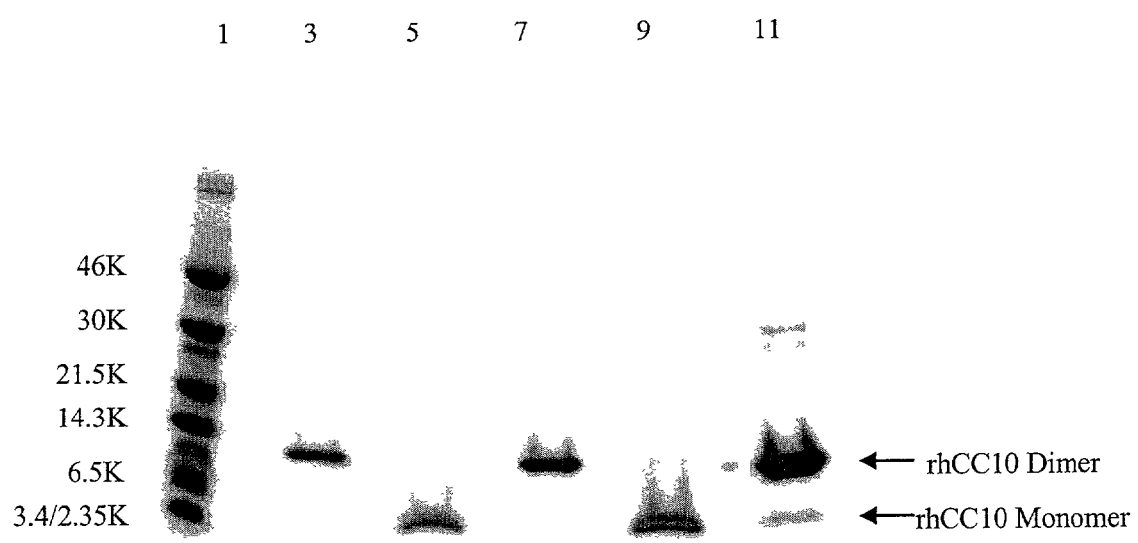

FIG. 21 shows SDS-PAGE analysis of purity of drug substance.

10–20% Tricine gel: samples are, from left to right Lane 1, Rainbow Standard; lane 3, 5 µg 0726; lane 5, 5 µg reduced 0726; lane 7, 10 µg 0726; lane 9, 10 µg reduced 0726; lane 11, 55 µg 0726. Lanes 2, 4, 6, 8, 10, and 12 were left unfilled.

Figure 22:
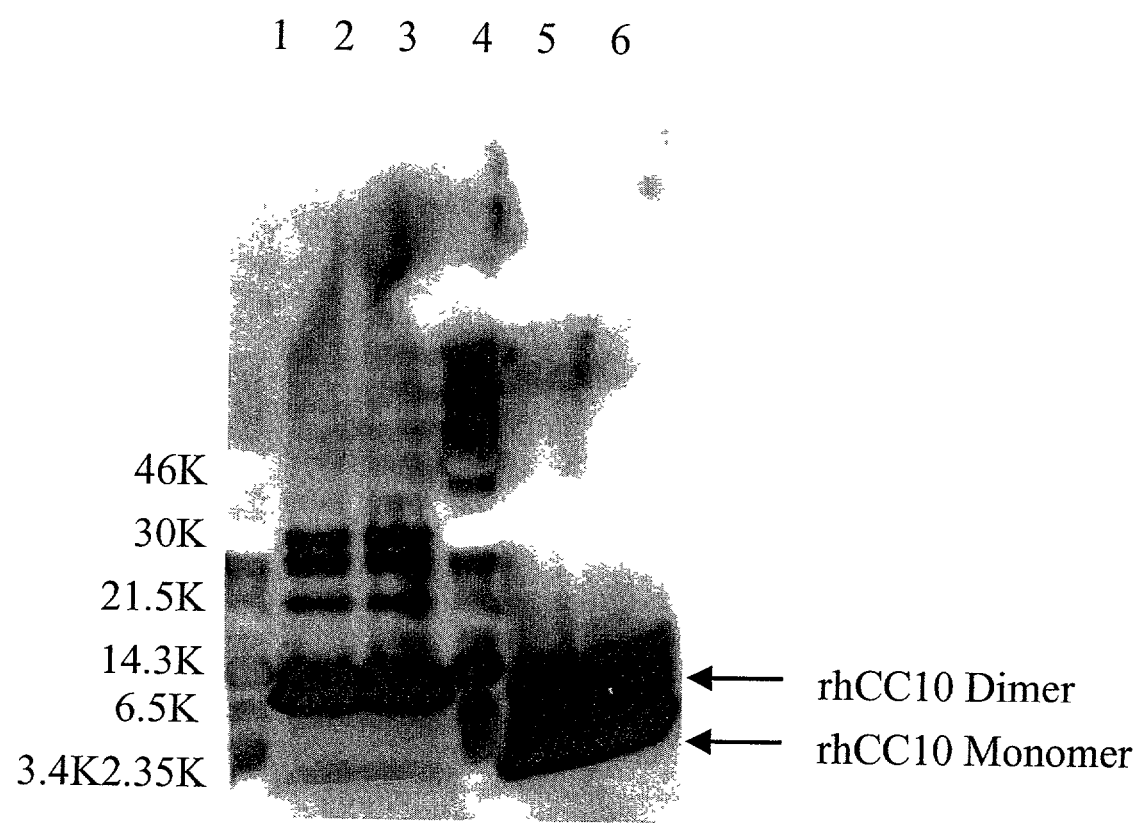

FIG. 22 shows Western Blot of drug substance using anti-UG polyclonal antibody.

10–20% Tricine gel transferred to Hybond-P PVDF transfer membranes, samples are, from left to right: Lane 1, Rainbow standard; lane 2, rhCC10 (lot 0726); lane 3, rhCC10 (lot 0728) lane 4, Rainbow Standard; lane 5, reduced rhCC10 (lot 0726); Lane 6, reduced rhCC10 (lot 0728).

Figure 23:
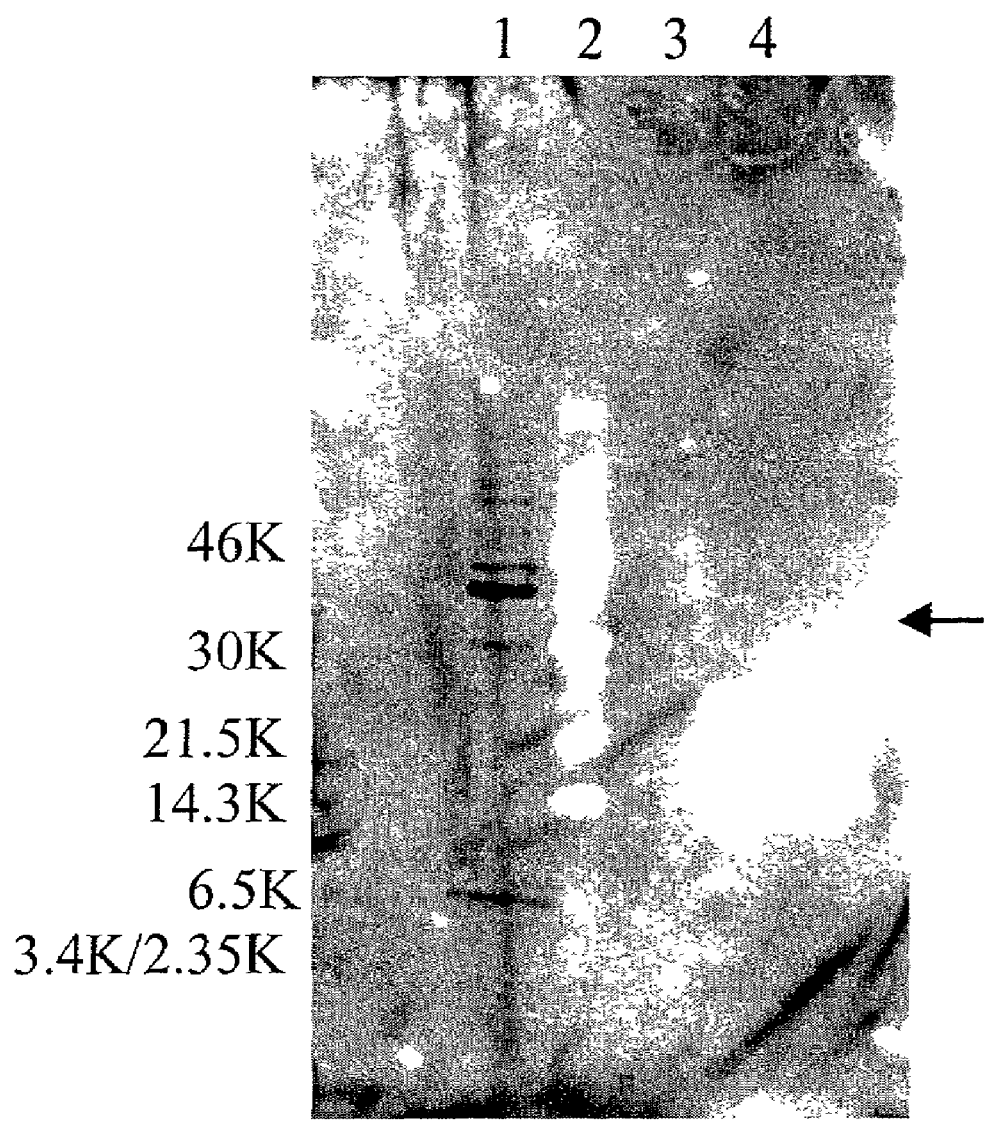

FIG. 23 shows Western Blot of drug substance using anti-*E. coli* lysate polyclonal antibody.

10–20% Tricine gel transferred to Hybond-P PVDF transfer membranes, Samples are, from left to right: Lane 1, Standard, *E. coli* cell lysate from BL21 (DE3); lane 2, Rainbow Standard; lane 3, rhCC10 (lot 0726); Lane 4, rhCC10 (lot 0728). The arrow indicates the location of the *E. coli* impurity in lanes 3 and 4.

Figure 24:
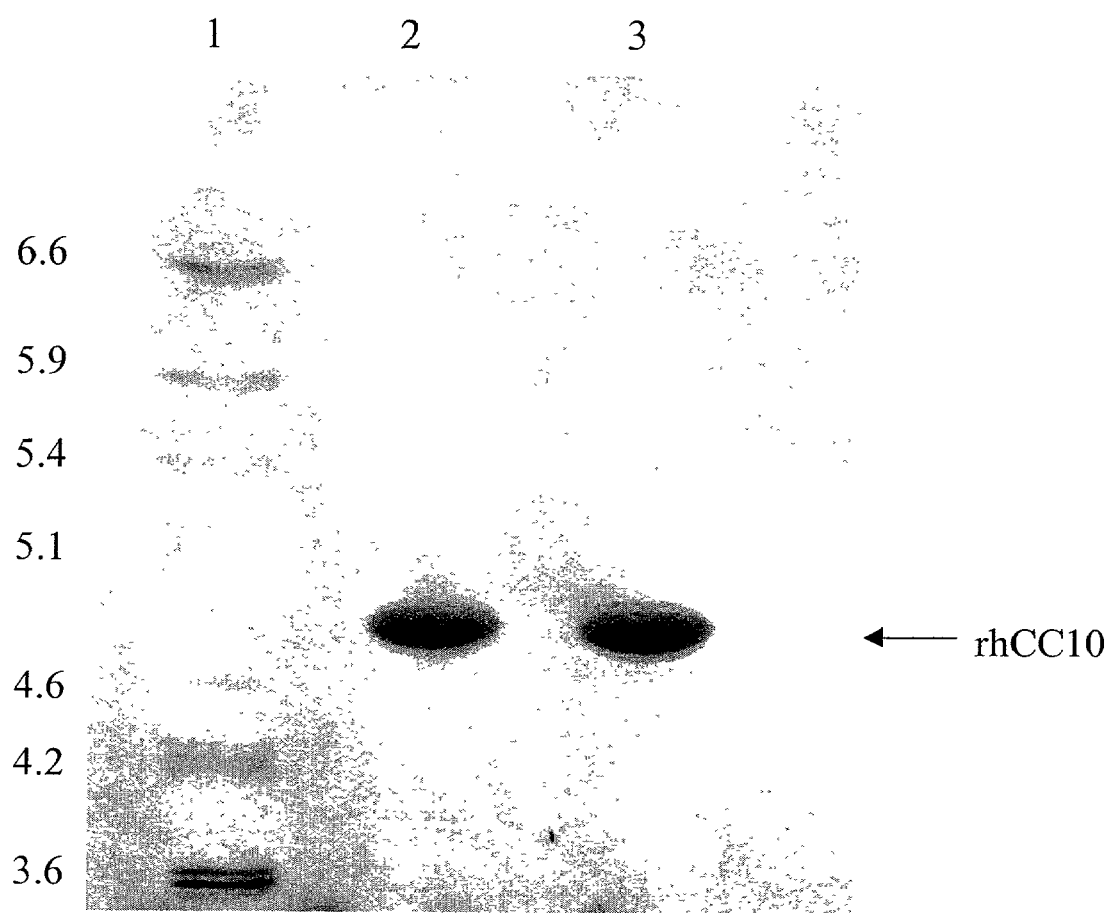

FIG. 24 shows isoelectric focusing PAGE gel of rhUG drug substance.

Samples are, from left to right: lane 1, standards; lane 2, 55 µg of rhCC10 lot 0726; lane 3, 55 µg of rhCC10 lot rhCC10/.

Figure 25:
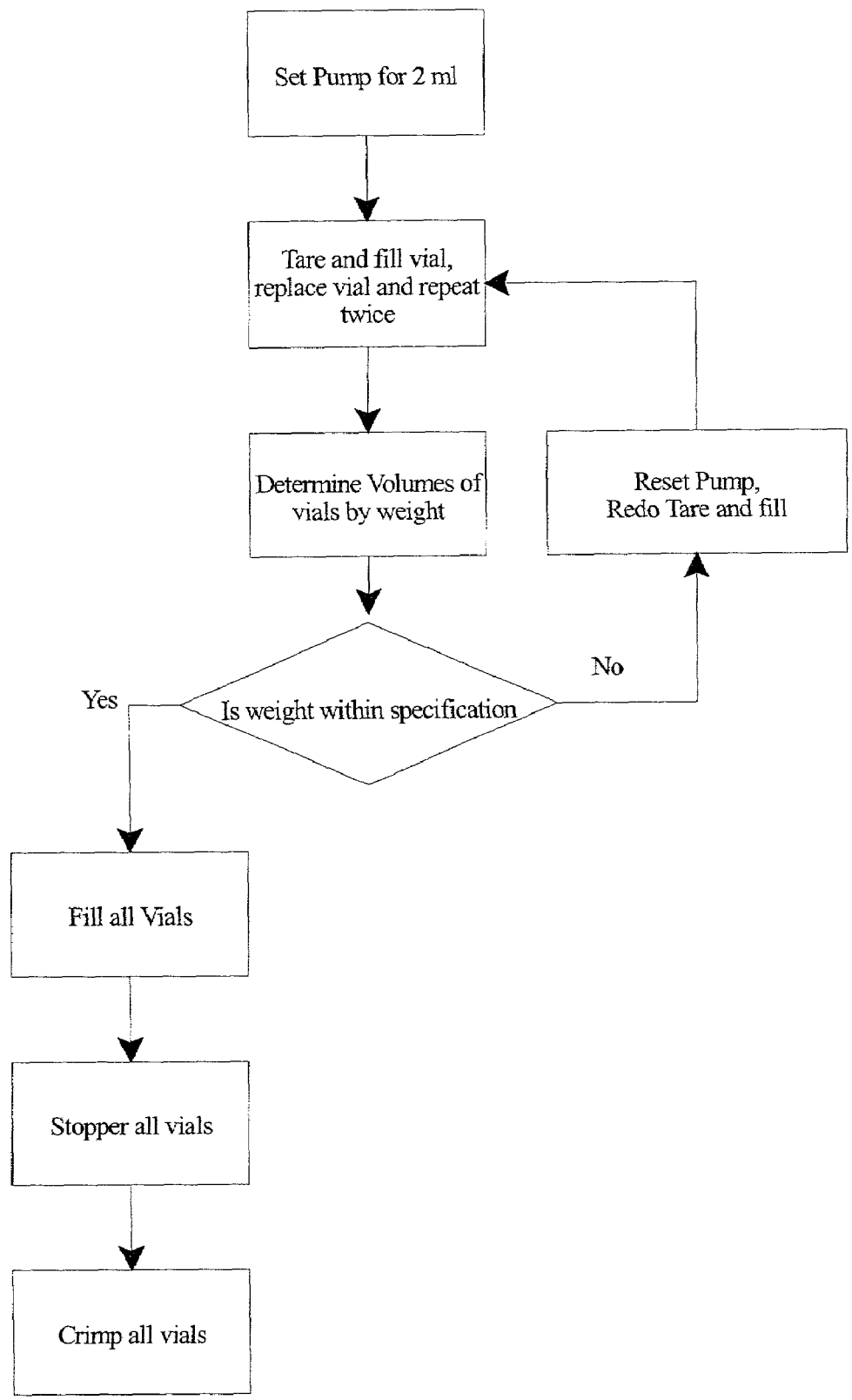

FIG. 25 shows a flow diagram of rhUG fill process.

Figure 26:
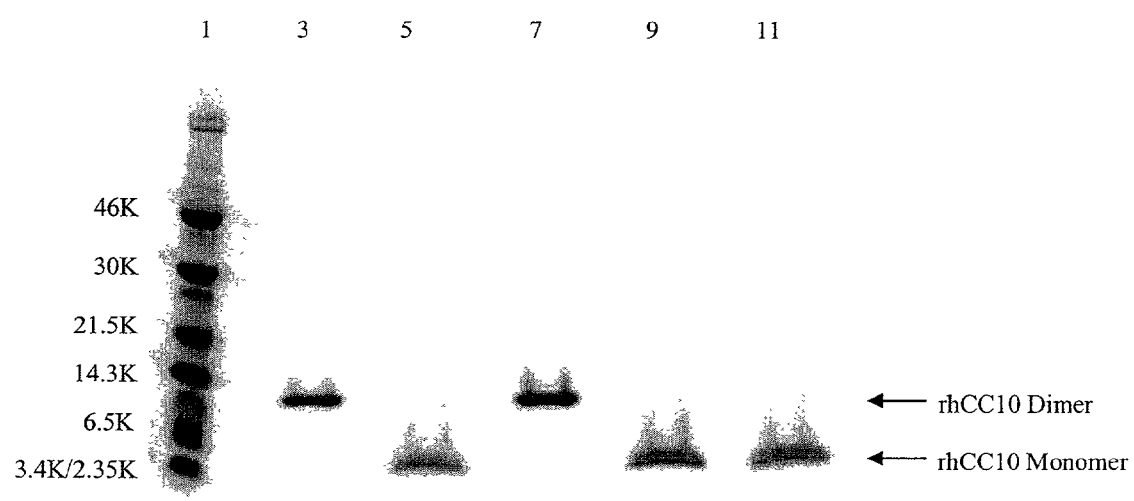

FIG. 26 shows SDS-PAGE analysis of purity of drug product.

10–20% Tricine gel, samples are, from left to right: lane 1, Rainbow Standard; lane 3, 5 µg 0728; lane 5, 5 µg reduced 0728; lane 7, 10 µg 0728; lane 9, 10 µg reduced 0728; lane 11, 10 µg reduced research control, rhCC10/7. Lanes 2, 4, 6, 8, 10, and 12 were left unfilled.

Figure 27:
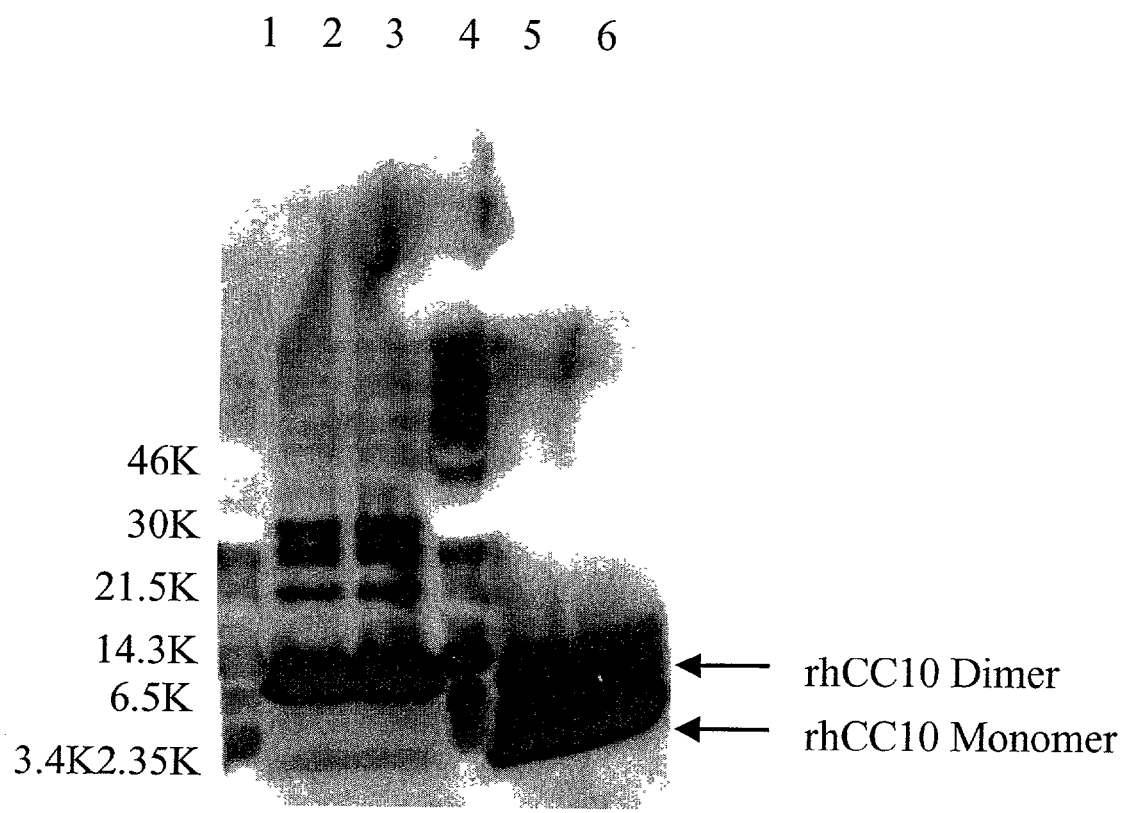

FIG. 27 shows Western Blot of drug product using anti-UG polyclonal antibody.

10–20% Tricine gel transferred to Hybond-P PVDF transfer membranes, samples are, from left to right: lane 1, Rainbow standard; lane 2, rhCC10 (lot 0726); lane 3, rhCC10 (lot 0728); lane 4, Rainbow Standard; lane 5, rhCC10 (lot 0726); lane 6, reduced rhCC10 (lot 0728).

Figure 28:
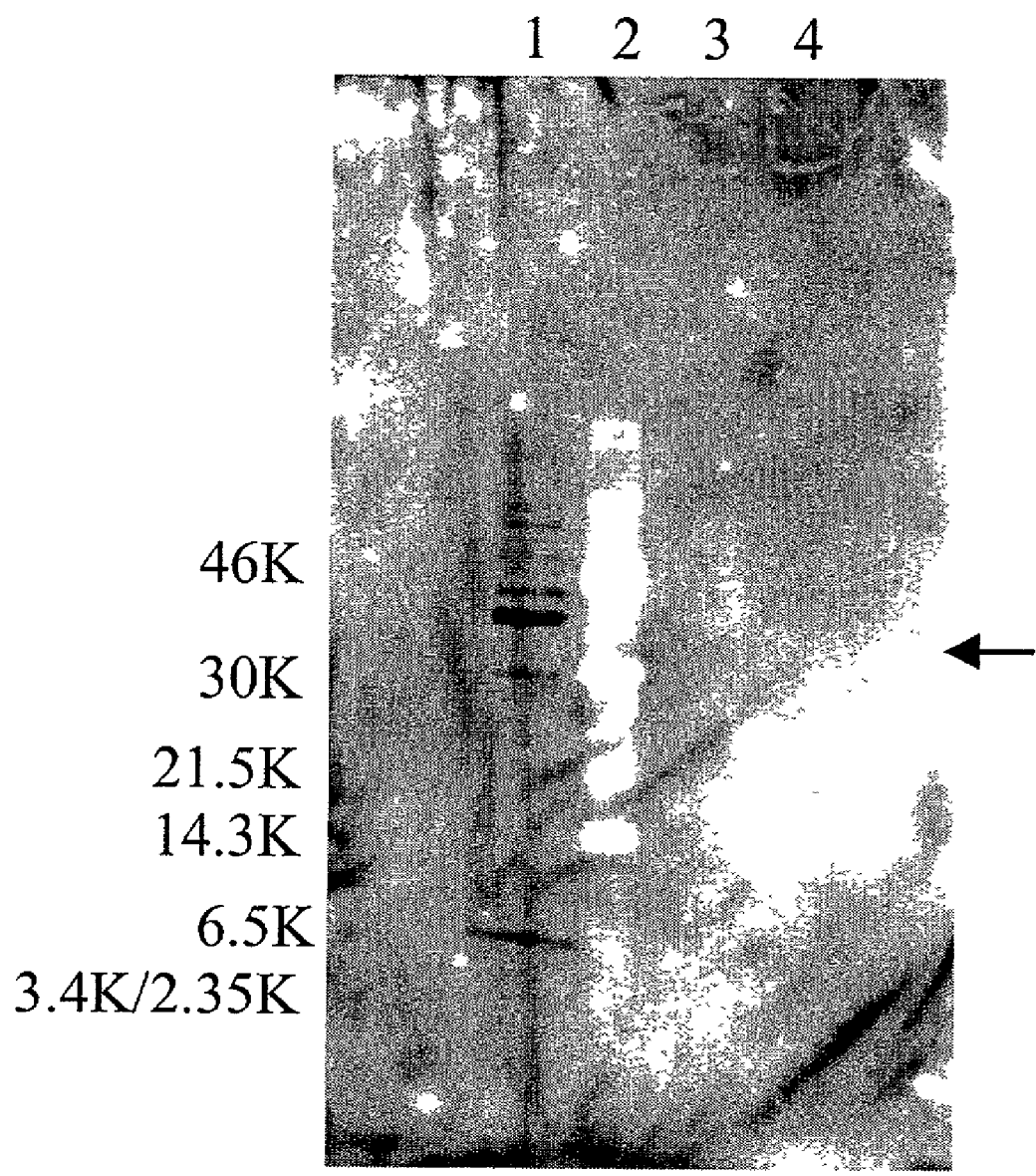

FIG. 28 shows Western Blot of drug product using anti-*E. coli* lysate polyclonal antibody.

10–20% Tricine gel transferred to Hybond-P PVDF transfer membranes, samples are, from left to right: lane 1, Standard, *E. coli* cell lysate from BL21 (DE3); lane 2, Rainbow Standard; lane 3, rhCC10 (lot 0726); lane 4, rhCC10 (lot 0728). The arrow indicates the position of the band at ~40 kD in lanes 3 and 4.

Figure 29:
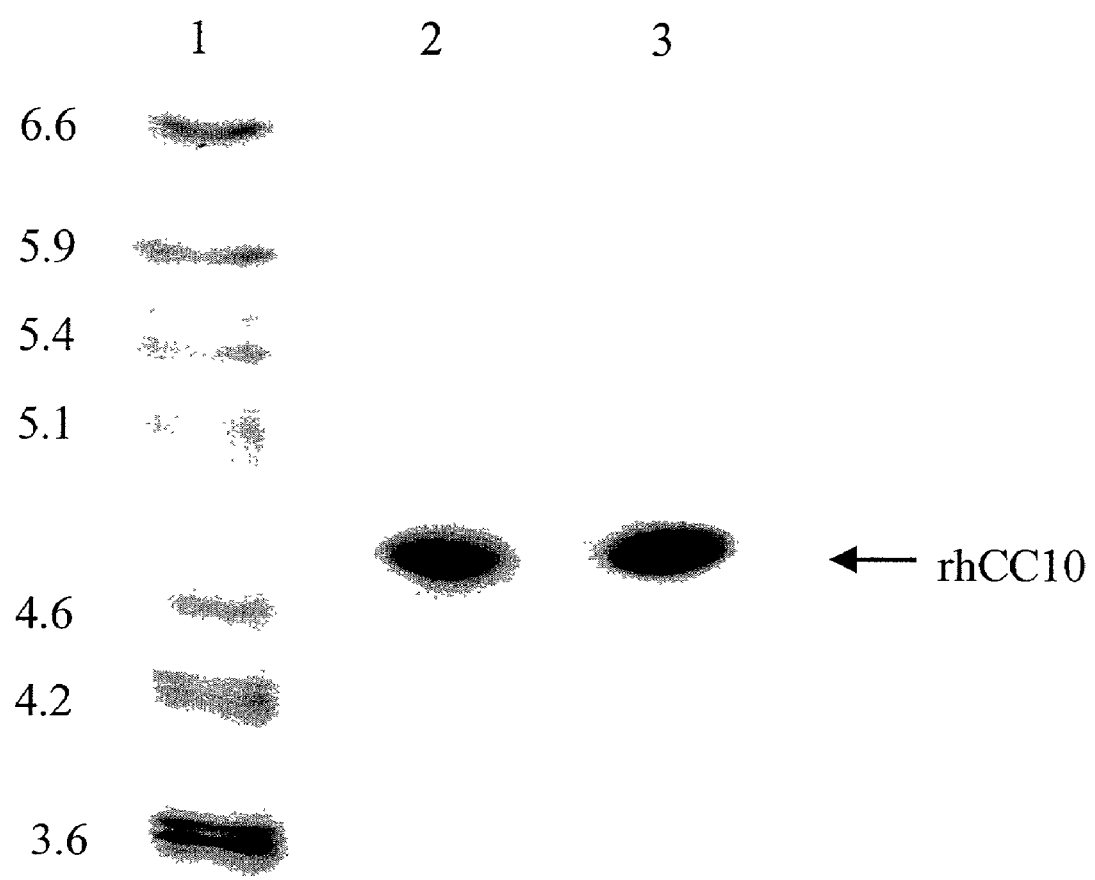

FIG. 29 shows isoelectric focusing PAGE gel of rhUG drug product.

Samples are, from left to right, lane 1, standards; lane 2, 55 μg of rhCC10 lot 0728; lane 3, 55 μg of rhCC10 lot rhCC10/7.

FIG. 30 shows the nucleotide sequence for cCG12 (SEQ ID NO: 9)

FIG. 31 shows the amino acid sequence for rhUG (SEQ ID NO: 11)

DETAILED DESCRIPTION OF THE INVENTION

The disclosures in copending application Ser. Nos. 08/864,357; 09/087,210; 09/120,264; 09/549,926; 09/861,688; PCT/US98/11026 (WO 98/53846); PCT/US99/16312 (WO 00/04863); PCT/US00/09979 (WO 00/62795); and PCT/US01/12126 (WO 01/079285) are hereby incorporated by reference.

Definitions

"Pure rhUG" as used herein means 1) that no other proteins are detectable in the rhUG preparation by SDS-PAGE, Western blot or immunoprecipitation with anti-*E. coli* antibodies, or by analytical HPLC; 2) that no bacterial endotoxin is detectable by LAL test; 3) that no bacterial nucleic acid is detectable by Southern blot (DNA hybridization).

"Purified rhUG" as used herein means rhUG which has met all specifications relating to purity as defined herein.

"Pharmaceutical Grade rhUG" as defined herein means rhUG which as met all purity, physical and biological activity specifications as defined herein and described in application Ser. Nos. 08/864,357; 09/087,210; 09/120,264; 09/549,926; 09/861,688; PCT/US98/11026; PCT/US99/16312; PCT/US00/09979; and PCT/US01/12126.

"Isoforms" as used herein refers to alternative forms of a protein that can be distinguished by physical or chemical means and may possess different biological activities, including different conformations, small variations in chemical composition of amino acids resulting from post-translational modifications, or variations in purification and processing.

"Conformation" as used herein refers to the three-dimensional structure of a protein, including the way it is folded, surface charge and hydrophobicity distribution. Any given protein may have several conformations that can affect its interactions with the surrounding environment, as well as other proteins, chemicals and cells.

"Aggregates" as used herein refers to complexes made up of multiple individual units of a single protein.

"Impurity" as used herein refers to compounds routinely present in the final product other than the drug or biologic of interest and required excipients; impurities can be either product or process related.

"Contaminant" as used herein refers to compounds or materials present in the final product that are not routinely present.

"Specifications" as used herein refers to a set of criteria that define a pharmaceutical grade protein, drug substance and drug product with respect to physical and chemical parameters, as well as biological activity and antigenic identity.

"Potency Assay" as used herein refers to a specific test that is used to measure the biological activity of drug substance or drug product and is used to gauge the strength of the biological activities of the drug in vivo, for purposes of relating biological activity to a physical parameter such as protein concentration and comparing different preparations of a given drug to each other.

"Immunoassay" as used herein refers to a test that is used to identify an antigen, in this case uteroglobin, through the use of one or more antibodies, including ELISAs (enzyme-linked immunosorbent assay).

"Formulation" as used herein refers to a specific pharmaceutical composition containing the biologically active drug substance plus specific excipients.

"Process Intermediate" as used herein refers to a sample comprising or derived from the product of each step in a process.

"Bulk Drug"—(See "Drug Substance")

"Drug Substance" as used herein refers to the purified drug, i.e. rhUG, prior to final formulation and fill into the final drug containers.

"Drug Product" as used herein refers to the drug in its final form for use in the patient population.

"RhUG Drug Substance" as used herein means pharmaceutical grade preparation of rhUG meeting specifications set forth herein and mediates the activity described herein and in application Ser. Nos. 08/864,357; 09/087,210; 09/120,264; 09/549,926; 09/861,688; PCT/US98/11026; PCT/US99/16312; PCT/US00/09979; and PCT/US01/12126.

"RhUG Drug Product" as used herein means pharmaceutical grade preparation of rhUG meeting specifications set forth herein and mediates the activity described herein and in application Ser. Nos. 08/864,357; 09/087,210; 09/120,264; 09/549,926; 09/861,688; PCT/US98/11026; PCT/US99/16312; PCT/US00/09979; and PCT/US01/12126.

"Standard Operating Procedure" as used herein means a defined procedure for the execution of a particular task under cGMP guidelines.

"Research Seed Bank" as used herein means a seed bank made under GLP conditions.

"Master Seed Bank" as used herein means a seed bank made under cGMP conditions, the purpose of the seed bank is to act as a source for the production of the Production Seed bank and for long term storage.

"Production Seed bank" as used herein means a seed bank made under cGMP conditions to be used to initiate the cGMP fermentation.

"cGMP" as used herein means current Good Manufacturing Practices.

"cGMP Production Process" as used herein means a production process that occurs under cGMP as defined by the FDA.

"Stable Drug Substance/Product" as used herein means a drug substance/product that meets a series of pre-defined criteria indicative of biological and physical stability.

"Biologically Active rhUG" as used herein means UG which can both inhibit the activity of $PLA_2$ and bind to recombinant human fibronectin fragments, and activities described in application Ser. Nos. 08/864,357; 09/087,210; 09/120,264; 09/549,926; 09/861,688; PCT/US98/11026; PCT/US99/16312; PCT/US00/09979; and PCT/US01/12126.

DESCRIPTION OF THE PREFERRED EMBODIMENTS

The invention includes bacterial expression systems for the production of rhUG. In one embodiment the bacterial expression system comprises a synthetic gene which codes for human UG. In another embodiment the synthetic gene comprises SEQ ID NO: 1–4. The invention also provides a bacterial expression system for production of rhUG comprising a human cDNA sequence which codes for human UG wherein the gene further comprises Met-Ala-Ala at the N-terminus of the sequence. In a further embodiment the synthetic gene further comprises Met-Ala-Ala at the N terminus of the synthetic gene. In still another embodiment the expression system further comprises an approximately 2.8 kb par sequence.

The invention also includes methods of producing a rhUG research seed bank. In one embodiment the method of producing a rhUG research seed bank comprises the steps of: a) inoculating onto a growth medium at least one colony of a bacterial strain comprising a rhUG expression system; b) incubating the inoculated growth medium until a stationary phase is reached; c) adding a cryopreservative, e.g. glycerol, to the inoculated growth medium; d) freezing the culture in aliquot portions; and e) storing the frozen aliquot portions at a temperature below about −50 C, preferably from −50° C. to −100° C. In another embodiment the method of producing a rhUG research seed bank comprises incubating the inoculated growth medium, monitoring the growth by optical density (OD) from 550 nm to 660 nm, preferably at 600 nm, until an optical density of about 0.8 Absorbance Units (AU) to 1.5 AU is reached.

The invention also includes methods of producing a rhUG master cell bank comprising the steps of: a) inoculating a suitable incubating broth with an aliquot portion of a rhUG research seed bank to form a bacterial culture; b) incubating the bacterial culture; c) adding a cryopreservative to the bacterial culture to form a cryopreserved solution; d) transferring a portion of the cryopreserved solution to a cryovial; and e) storing the cryovial at a temperature below about −60 C, preferably from −50° to −100° C. In one embodiment the method of producing a rhUG master cell bank comprises incubating the bacterial culture, monitoring the growth by optical density (OD) from 550 nm to 660 nm, preferably at 600 nm, until an optical density of about 0.8 AU to 1.5 AU is reached.

Methods for producing a rhUG production cell bank from a portion of the master cell bank are also disclosed.

The present invention includes methods for expressing rhUG. In one embodiment the method for expressing rhUG comprises the steps of: a) providing a production seed cell bank culture comprising an expression vector capable of expressing rhUG; b) inoculating a broth medium with the production seed cell bank culture to form an inoculum; c) incubating the inoculum formed in step b; d) inoculating a large scale fermenter with the inoculum formed in step (c) to form a fermentation culture; e) incubating the fermentation culture formed in step (d) within the large scale fermenter; f) adding an induction agent to the fermentation culture formed in step (e) to induce the expression of rhUG; and harvesting the fermentation culture.

In one embodiment the method for expressing rhUG uses an expression vector comprising SEQ ID NO: 1–4. In another embodiment the inoculum is incubated for a period between about 12 hours and about 24 hours at a temperature between about 28° C. and about 36° C. In yet another embodiment the incubation of step (e) is continued until a minimum OD, in the range of 550 nm to 660 nm, preferably at 600 nm, of two Absorbance Units is reached.

The induction agent may be isopropyl-beta-D-thiogalactopyranoside (IPTG). In still another embodiment about 1 to 4 hours elapses between the induction step and the harvesting step. In yet another embodiment harvesting the fermentation culture utilizes centrifugation.

The present invention provides further methods of expressing rhUG comprising the steps of: a) inoculating a large scale fermenter with an inoculum comprising an expression vector capable of expressing rhUG to form a fermentation culture; b) incubating the fermentation culture within the large scale fermenter c) adding an induction agent to the fermentation culture to induce the expression of rhUG; and d) harvesting the fermentation culture.

In one embodiment for expressing rhUG the expression vector comprises SEQ ID NO: 1–4. The invention provides in another embodiment the large scale fermenter has at least a 300 liter capacity. In yet another embodiment the incubation of step b is continued until a minimum optical density from 550 nm to 660 nm, preferably 600 nm, of about 2.0 AU is achieved. In still another embodiment the induction agent comprises isopropyl-beta-D-thiogalactopyranoside (IPTG). In a further embodiment about 1 to about 4 hours elapses between step c and step d. In a further embodiment harvesting the fermentation culture comprises centrifugation.

The invention further includes methods of purifying rhUG. In one embodiment the method of purifying rhUG comprising the steps of: a) providing a bacterial cell paste comprising bacterial cells capable of overexpressing rhUG; b) lysing the bacterial cell paste to form a supernatant; c) filtering the supernatant through a first nominal molecular weight cut off (NMWCO) membrane to form a first permeate; d), concentrating the first permeate by the use of a second NMWCO membrane to form a first concentrate; e) loading the concentrated permeate formed in step (d) onto an anion exchange column to form a first eluate; f) concentrating the first eluate formed in step (e) by the use of a third NMWCO membrane to form a second concentrate; (g) loading the second concentrate onto a Hydroxyapatite (HA) column to form a second eluate; h) separating host-derived proteins in the second eluate, from the rhUG to provide purified rhUG; and i) recovering the purified rhUG.

In one embodiment the method of purifying rhUG, utilizes bacterial cells which comprise SEQ ID NO: 1–4. In another embodiment lysing the bacterial cell paste is achieved through shearing. In still another embodiment cell debris is removed by centrifugation between steps (b) and (c). In yet another embodiment the membrane of step (b) is about a 30K to 100K NMWCO membrane.

In another embodiment the filtering of step (c) comprises the use of a tangential flow filtration (TFF) system. In another embodiment the membrane of step d is about a 5k cutoff membrane. In still another embodiment the anion exchange column is a Macro Q anion exchange column. In yet another embodiment the host-derived proteins are separated with a Chelating SEPHAROSE® (a chromatography medium) Fast Flow (CSFF) resin column. In one embodiment the CSFF resin column comprises copper. In yet another embodiment the host-derived proteins are separated from the rhUG by filtering the rhUG through a 30 K NMWCO membrane.

In another embodiment a positively charged membrane is placed downstream of the CSFF column forming a pass through substantially free of host derived proteins. In one embodiment this positively charged membrane is a SARTOBIND® Q TFF membrane. In still another embodiment the pass through is diafiltered through about a 5K NMWCO membrane. In another embodiment the rhUG recovered in step i is substantially free of aggregates.

The present invention provides further methods of purifying rhUG. One of these further methods comprises the steps of: a) providing bacterial cells capable of overexpressing rhUG; b) lysing the bacterial cells to form a supernatant liquid; c) filtering the liquid through a molecular weight cut off (NMWCO) membrane; d) loading the liquid onto an exchange column; e) separating host-derived proteins from the rhUG to provide purified rhUG; and f) recovering the purified rhUG.

In another embodiment the filtering of step c comprises the use of a tangential flow filtration (TFF) system. In yet another embodiment the anion exchange column is a Macro Q anion exchange column. In still another embodiment the host-derived proteins are separated with a Chelating SEPHAROSE® Fast Flow (CSFF) resin column. In another embodiment the recovered rhUG is substantially free of aggregates.

The present invention also provides methods of producing a pharmaceutical grade rhUG drug substance comprising the steps of: a) providing a bacterial expression system capable of expressing rhUG; b) inoculating a fermenter with an inoculum comprising the bacterial expression system to form a fermentation culture; c) adding an induction agent to the fermentation culture to induce the expression of rhUG by the bacterial expression system; d) harvesting the rhUG expressed in step c; and e) purifying the rhUG harvested in step d, wherein the purifying step comprises the use of at least one filter and at least one exhange column.

The invention also includes an assay method for determining the potency of recombinant human uteroglobin in a sample which comprises: (a) contacting a sample containing recombinant human uteroglobin with phospholipase $A_2$, (b) introducing a labeled substrate to said sample, and (c) separating product from sample, and (d) determining level of cleavage. In one embodiment, the assay is used in conjunction with a standard $^{14}$C-labeled assay. In another embodiment of the invention, the labeled substrate is 1-stearoyl-2-[1-$^{14}$C]arachidonyl phosphatidyl choline. In a further embodiment, the recombinant human phospholipase $A_2$ is added to a final concentration of from 2 nM to 200 nM in step (a). In another embodiment of the invention, the sample of step (a) is preincubated for from 15 minutes to 30 minutes at from 30° C. to 40° C. In yet another embodiment of the invention, the labeled substrate added in step (b) is added to a final concentration of from 0.5 μg/ml to 50 μg/ml.

In an embodiment of the invention, the reaction in step (b) is stopped after from 5 minutes to 30 minutes by addition of an organic phase stopping solution. One example of an organic phase stopping solution is a 7.7 dilution with Doles reagent and purified water (84:16). In an embodiment of the invention, the sample in step (c) is separated by vortexing and centrifugation, and the product of step (c) is arachidonic acid, which is separated from the sample by liquid—liquid separation in step (c).

In an embodiment of the invention, the sample is separated and the top layer removed for scintillation counting to determine the level of cleavage in step (d). Separation may be accomplished by vortex and centrifugation.

The present invention also provides a method for measuring in vitro the anti-inflammatory effect arising from inhibition or blocking of secretory phopsholipase $A_2$ enzymes by recombinant human uteroglobin, comprising: (a) contacting a sample containing recombinant human uterogloblin with phospholipase $A_2$, (b) introducing labeled substrate to said sample, (c) separating product from sample, and (d) determining level of cleavage by scintillation counting.

The present invention further provides an assay method for assaying for the inhibition of secretory phopsholipase $A_2$ activity by recombinant human uteroglobin, comprising: (a) contacting a sample containing recombinant human uterogloblin with phospholipase $A_2$, (b) introducing labeled substrate to said sample, (c) separating product from sample, and (d) determining level of cleavage by scintillation counting.

The present invention provides an assay method for determining the potency of recombinant human uteroglobin in a sample which comprises: (a) contacting a sample containing recombinant human uterogloblin with phospholipase $A_2$, (b) introducing flourescently labeled substrate to said sample, (c) separating non-cleaved substrate from sample, and (d) determining amount of cleaved substrate by flourescence.

In an embodiment of the invention, the sample of recombinant human uteroglobin in step (a) has a final concentration of 34 nM to 34 μm. In another embodiment of the invention, the sample of step (a) is preincubated for 15–30 minutes at 30–40° C.

In a further embodiment of the invention, the flourescently-labeled substrate is 2-decanoyl-1-(O-(11-(4,4-difluoro-5,7-dimethyl-4-bora-3a,4a-diaza-s-indacene-3 propionyl)amino)undecyl)-sn-glycero-3-phosphotidylcholine. In yet another embodiment of the invention, the substrate added in step (b) is added to a final concentration of 0.5–50 μg/ml.

In an embodiment of the invention, the reaction in step (b) is stopped after 5–30 minutes by addition of a one to five dilution of an organic phase stopping solution. In another embodiment of the invention the organic phase stopping solution is 2-Propanol:n-hexane(8:3). In another embodiment of the invention, 1 μL to 100 μL of the stopped assay is loaded directly onto a silica normal phase HPLC column in step (c). In a further embodiment of the invention, the flourescence of step (d) has excitation at 460 nm to 505 nm and emmision at 505 nm to 550 nm.

The present invention provides a method for measuring in vitro the binding of recombinant human uteroglobin to fibronectin, comprising: (a) contacting a recombinant fragment of human fibronectin with a recombinant human CC10-HRP conjugate, and (b) visualizing the assay to determine binding of recombinant human uteroglobin to the fibronectin fragment.

The present invention also provides a method for determining the purity of recombinant human uteroglobin which comprises, (a) taking samples of intermediates at each step within the process of claim, and (b) analyzing the process intermediates.

In an embodiment of the invention, process intermediates are analyzed by SDS-PAGE in step (b). In another embodiment of the invention, process intermediates are analyzed by rhUG ELISA in step (b). In a further embodiment of the invention, process intermediates are analyzed by LAL in step (b). In yet another embodiment of the invention, intermediates are analyzed for protein content in step (b).

The present invention provides a pharmaceutical composition comprising the purified recombinant human uteroglobin of the present invention. The present invention also provides a pharmaceutical composition comprising a purified recombinant human uteroglobin and a pharmaceutically acceptable carrier or diluent.

In an embodiment of the invention, the recombinant human uteroglobin contains less than 5% aggregates of recombinant human uteroglobin. In another embodiment of the invention, the recombinant human uteroglobin has a purity of greater than 95%. In a further embodiment of the invention, the level of endotoxin in the recombinant human uteroglobin comprises less than 5 EU/mg rhUG. In yet another embodiment of the invention, the recombinant human uteroglobin is in a sodium chloride solution.

In an embodiment of the invention, the recombinant human uteroglobin is stable in solution at 4° C. for at least 4 months. In another embodiment of the invention, the recombinant human uteroglobin is stable in solution at 4° C. for at least 6 months. In a further embodiment of the invention, the recombinant human uteroglobin is stable in solution at 4° C. for at least 9 months. In yet another embodiment of the invention, the recombinant human uteroglobin is stable in solution at 4° C. for at least 12 months. In yet another embodiment of the invention, the recombinant human uteroglobin is stable in solution at 4° C. for at least 15 months. In yet another embodiment of the invention, the recombinant human uteroglobin is stable in solution at 4° C. for at least 18 months. In an embodiment of the invention, the recombinant human uteroglobin is stable in solution at 25° C. and 60% room humidity for at least 1 months. In an embodiment of the invention, the recombinant human uteroglobin is stable in solution at 25° C. and 60% room humidity for at least 2 months. In an embodiment of the invention, the recombinant human uteroglobin is stable in solution at 25° C. and 60% room humidity for at least 4 months. In an embodiment of the invention, the recombinant human uteroglobin is stable in solution at 25° C. and 60% room humidity for at least 7 months.

In another embodiment of the invention, the recombinant human uteroglobin is safe to administer to a mammal. In a further embodiment of the invention, the recombinant human uteroglobin is safe to administer to a human. In yet another embodiment of the invention, the recombinant human uteroglobin is safe to administer via an intratracheal tube. In an embodiment of the invention, the recombinant human uteroglobin is safe to administer to a premature infant. In another embodiment of the invention, the recombinant human uteroglobin is safe to administer to a patient receiving artificial surfactant. In a further embodiment of the invention, the recombinant human uteroglobin is safe to administer to a patient in respiratory distress.

Recombinant human UG was produced by the procedures described below. The rhUG had levels of purity exceeding 97% such that it may be used, inter alia, according to the inventions described in application Ser. Nos. 08/864,357; 09/087,210; 09/120,264; 09/549,926; 09/861,688; PCT/US98/11026; PCT/US99/16312; PCT/US00/09979; and PCT/US01/12126 to modulate the immune response, to inhibit inflammation and reduce or prevent fibrosis and unregulated cell proliferation in vitro and in vivo. In certain embodiments the level of purity was 99% or greater.

Preparation of the rhUG-Expressing Episome and the rhUG-Producing Strain of Bacteria Two types of novel bacterial expression systems were developed for the production of recombinant human UG. One involved the construction of a novel synthetic gene for human UG, using codons optimized for bacterial protein synthesis. The other provides for the use of a bacterial genetic element conferring stable plasmid inheritance in the absence of antibiotic selection. Both approaches yielded bacterial host-vector systems capable of efficient UG over-expression.

Construction of a Synthetic Bacterial Gene for rhUG

A synthetic bacterial gene sequence for human UG was designed to improve bacterial expression and was assembled from synthetic oligonucleotides. Because mature native UG has a glutamic acid residue at its N-terminus, an initiator methionine must be added at the N-terminus, which allows initiation of peptide synthesis (translation) from mRNA in bacteria. Codon usage was optimized for expression in bacteria, by incorporating the most frequently used codons in bacteria (Anderssen and Kurland, 1990) into the protein coding sequence. Synthtetic genes for expression of recombinant human UG can similarly be constructed by tailoring codon usage for optimized expression in insect cells, plant cells, yeast cells, and other non-primate mammalian species. The optimization of codon usage results in a higher translation efficiency and protein expression level. The use of codons preferred in bacteria also may decrease the stress response to the metabolic burden created by the consumption of rare charged tRNAs. Without being bound by a particular theory, it is believed that this stress response resulting from imbalances in bacterial charged tRNAs may alter transcription patterns, increases cellular proteolysis, and alters cellular metabolism. All of these factors may contribute to problems with reproducibility in fermentation cultures in which the protein product is expressed. Variations in the production cultures may lead to larger problems in downstream purification in which new bacterial proteins appear at different steps in the process.

EXAMPLE I

Assembly of a Synthetic Bacterial Gene

Figure 1:
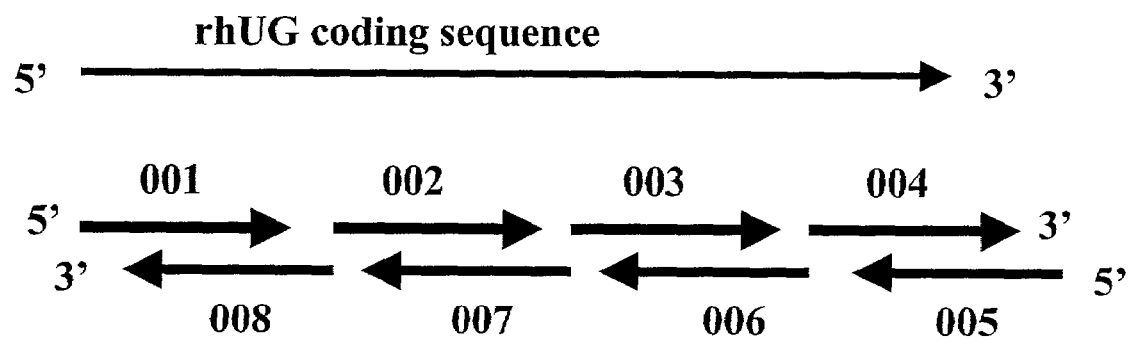
FIG. 1 shows construction of synthetic bacterial gene for rhUG.
Figure 2:
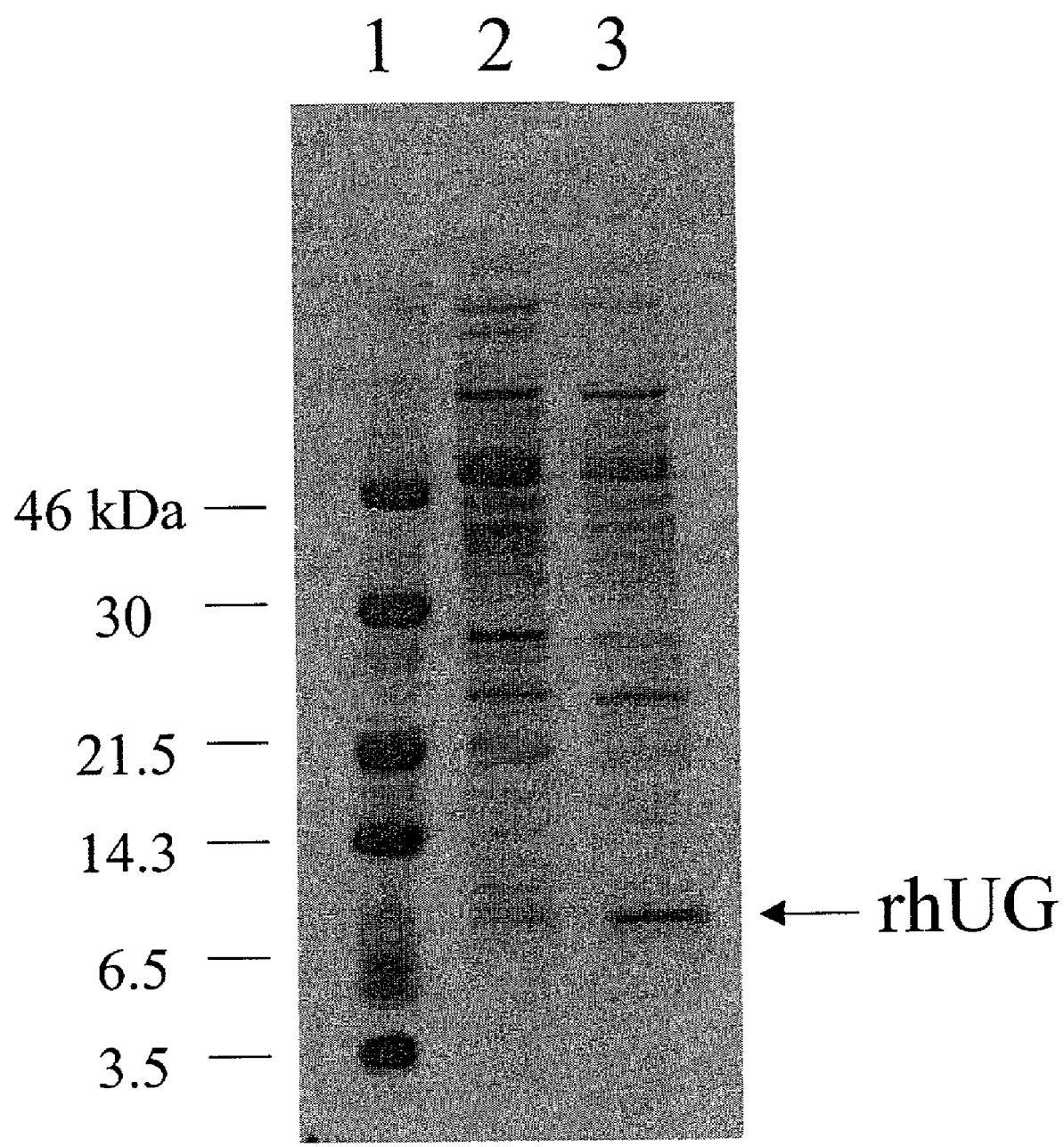
FIG. 2 shows expression of rhUG using a synthetic bacterial gene: SDS-PAGE analysis.

The synthetic bacterial gene for rhUG was assembled from oligonucleotides as shown in Table 1. (Synthetic oligonucleotides were obtained from Bioserve Biotechnologies, Inc.) Oligonucleotides 1–4 (SEQ ID NO: 1–4), respectively, represent the coding strand and 5–8 (SEQ ID NO: 5–8), respectively, represent the complementary strand. Both sets are in order from 5' to 3', respectively, and were assembled by annealing and ligation using standard methods as shown in FIG. 1. Ligation mixtures were transformed into appropriate strains as shown in Table 2 below and plasmid vector-bearing colonies were selected with appropriate antibiotic. Transformants were initially screened with a quick PCR assay done directly on the bacterial colonies to determine insert size. Colonies bearing the ~234 bp rhUG insert were then subcultured for further screening. The secondary screen was done on 10 ml bacterial cultures from PCR-positive clones, where expression of an inducible protein band of approximately 10 kDa is sought (See FIG. 2). Samples of whole cells, induced appropriately for expression of rhUG, were directly lysed in 2×SDS-PAGE gel loading buffer. The samples were run on 16% Tris-glycine SDS-PAGE gels in a minigel apparatus (Novex). The screening procedures were as described in detail in Pilon (1997), incorporated herein by reference. Plasmid DNA from clones that overexpressed an inducible UG band was prepared and the DNA sequence of the rhUG coding region was again verified. Both plasmid DNA and single colony bacterial isolates from streaks of positive clones were then frozen down for storage at −20° C. and −80° C.

TABLE 1

Oligonucleotides used in Construction of a Synthetic Bacterial Gene rhUG

| Oligo. ID | Nucleotide Sequence |
|---|---|
| 1 | 5'-GATCCATGGAAATCTGCCCGTCTTTCCAGC GTGTTATCGAAACCCTGCTGATGGACACCCCGTCC-3 |
| 2 | 5'-AGCTACGAAGCAGCTATGGAACTGTTCTCT CCGGACCAGGACATGCGTGAAGCAGGTGCT-3' |

TABLE 1-continued

Oligonucleotides used in Construction
of a Synthetic Bacterial Gene rhUG

| Oligo. ID | Nucleotide Sequence |
|---|---|
| 3 | 5'-CAGCTGAAGAAACTGGTTGACACCCTGCCG CAGAAACCGCGTGAATCCATCATAAACTG-3' |
| 4 | 5'-ATGGAGAAGATCGCTCAGTCTAGCCTGTGC AACTAAG-3' |
| 5 | 5'-CTTAGTTGCACAGGCTAGACTGAGCGATCT TCTCCATCAGTTTGATGATGGATTCACGCG-3' |
| 6 | 5'-GTTTCTGCGGCAGGGTGTCAACCAGTTTCT TCAGCTGAGCACTGCTTCACGCATGTCCT-3' |
| 7 | 5'-GGTCCGGAGAGAACAGTTCCATAGCTGCTT CGTAGCTGGACGGGGTGTCCATCAGCAGGG-3' |
| 8 | 5'-GGTCCGGAGAGAACAGTTCCATAGCTGCTT CGTAGCTGGACGGGGTGTCCATCAGCAGGG-3' |

Oligonucleotides homologous to the 5' and 3' ends of the synthetic gene, and containing flanking linkers with NcoI and BamHI restriction sites, respectively, were then used to amplify the synthetic bacterial gene by PCR and clone it into pKK223-3 (obtained from Pharmacia Corp.). The DNA sequence of the synthetic gene in pKK233-3 was confirmed. Poor rhUG expression from this clone suggested that extra amino acid residues would be required at the N-terminus, in addition to the initiator methionine (Peter, et al., 1989), in order to increase rhUG expression levels. Therefore, a set of synthetic bacterial rhUG genes with N-terminal additions of varying length were constructed to evaluate the optimal length for rhUG expression in bacteria. These extra amino acids may help to stabilize the nascent peptide in the bacterial ribosome and cytoplasm. The extra amino acids consisted of alternating glycines and serines, as these have small side chains, are not highly charged or highly hydrophobic, and therefore are unlikely to disrupt the natural folding and assembly of the UG monomers and dimers. Codon usage and linkers were used as described above and the genes were cloned into pKK223-3. The DNA sequence of each gene was verified. Clones selected for correct rhUG coding sequence and inducible expression of rhUG were inoculated from colonies on solid media into 50 ml of broth and shaken overnight. This starter culture is used to inoculate 250 ml of rich media containing antibiotic in shaker flasks. These cultures were grown under the appropriate conditions until they reached an optical density of 0.5 at 600 nm. Expression of rhUG was then induced for each clone (see Table 2). The cultures were shaken for an additional 2–4 hours. The cells were harvested by centrifugation, resuspended, and analyzed for rhUG expression by SDS-PAGE. The rhUG expression levels from each gene were compared and the gene that produced the most protein was selected for further host/vector system optimization. The gene producing the most protein had an N-terminus containing three extra amino acid residues in addition to the human uteroglobin sequence and is referred to as the MGS-gene.

There are significant disadvantages associated with the use of pKK223-3. First, pKK223-3 is not suitable for production of a biopharmaceutical in the United States because it requires ampicillin selection for stable plasmid inheritance from parent to daughter bacterial cells. Approximately 20% of the U.S. population is allergic to penicillin and its derivatives, one of which is ampicillin. For this reason, the FDA has barred the use of ampicillin in processes used to generate recombinant biopharmaceutical proteins. In the absence of ampicillin, the plasmid can be lost from the cells in the culture as parent cells divide and daughter cells containing the plasmid are not selected. Plasmid DNA replication represents a significant metabolic burden to the bacterial cells. In the absence of the antibiotic, the daughter cells lacking the plasmid will have a competitive advantage over daughter cells that still contain the plasmid and will rapidly take over the culture.

Second, the transcription of the synthetic gene is repressed by the lac repressor protein which binds to the lac promoter element and prevents uninduced expression of the downstream protein. Therefore, a high copy number of pKK223-3 may result in more promoter elements than there are lac repressor proteins in the cell, causing "leaky" protein expression. Transcription of the gene downstream of the lac promoter is actually turned on by adding a chemical (isopropyl thio-galactoside, "IPTG") that binds to the lac repressor protein, causing it to let go of the lac promoter DNA. Bacterial RNA polymerase then binds to the promoter and initiates transcription. The de-repression of the promoter thus induces mRNA transcription and protein expression. Leaky protein expression occurs when the downstream protein, in this case rhUG, is synthesized in the uninduced culture. Leaky rhUG expression from pKK223-3 was observed.

EXAMPLE II

Testing of Plasmid Vector Constructs in Strains of
E-Coli

Several different plasmid vector constructs containing the MGS-synthetic gene and different combinations of replicons, promoters, transcriptional repressors, and antibiotic selections were then tested in several different strains of E. coli. Several of these host/vector systems are shown in Table 2. A version of the synthetic gene with MAA- at the N-terminus was also made and tested in some of these host-vector systems. Subclonings of the synthetic genes into pRK248cIts were done using a BamHI fragment containing the rhUG synthetic gene from the pKK223-3 clones. Subclonings into pGEL101 and pGELAC were done using NcoI-BamHI fragments containing the gene in pKK223-3.

TABLE 2

Combinations Generated for Optimal rhUG Expression in E. coli

| Strain ID | rhUG-N-terminus | Vector | 5'RE–3'RE | Selection[1] | Induction | Promoter | Host Strain | Source |
|---|---|---|---|---|---|---|---|---|
| CG1 | M- | pKK223-3 | NcoI-BamH1 | Ampicillin[2] | IPTG[5] | Lac | DH5αF'I[q] | Life Technologies Inc |
| CG3 | FLAG- | pKK223-3 | NcoI-BamH1 | Ampicillin | IPTG | Lac | DH5αF'I[q] | Life Tech |
| CG4 | MGS- | pKK223-3 | NcoI-BamH1 | Ampicillin | IPTG | Lac | DH5αF'Iq | Life Tech |
| CG5 | MGSGS- | pKK223-3 | NcoI-BamH1 | Ampicillin | IPTG | Lac | DH5αF'Iq | Life Tech |

TABLE 2-continued

Combinations Generated for Optimal rhUG Expression in *E. coli*

| Strain ID | rhUG-N-terminus | Vector | 5'RE–3'RE | Selection[1] | Induction | Promoter | Host Strain | Source |
|---|---|---|---|---|---|---|---|---|
| CG8 | MGSGSGS- | pKK223-3 | Nco1-BamH1 | Ampicillin | IPTG | Lac | DH5αF'Iq | Life Tech |
| CG60 | MGS- | pGEL101 | Nco1-BamH1 | Ampicillin | IPTG | T7 RNA pol | BL21/DE3 | Novagen, Inc. |
| CG73 | MGS- | pRK248cIts-A7 | BamH1-BamH1 | Tetracycline[3] | Heat[6] | λPL | DH5αF'Iq | Life Tech |
| CG74 | MGS- | pRK248cIts-A | BamH1-BamH1 | Tetracycline | IPTG | T5/lacO hyb | DH5αF'Iq | Life Tech |
| CG77 | MAA- | pKK223-3 | Nco1-BamH1 | Ampicillin | IPTG | T5/lacO hyb | DH5αF'Iq | Life Tech |
| CG78 | MGS- | pRK248cIts-B | BamH1-BamH1 | Tetracycline | Heat | λPL | DH5αF'Iq | Life Tech |
| CG82 | MAA- | pGELAC | | Ampicillin[4] | IPTG | T5/lacO hyb | DH5αF'Iq | Life Tech |
| CG86 | MGS- | pRK248cIts-B | BamH1-BamH1 | Tetracycline | IPTG | T5/lacO hyb | W3110F'Iq | ATCC |
| CG98 | MAA- | pGELAC | Nco1-BamH1 | Ampicillin | IPTG | T5/lacO hyb | DH1 | ATCC |

[1]Antibiotic selection is required to select bacterial transformants containing the plasmid but may not be necessary for plasmid maintenance (e.g. stable inheritance of the plasmid).
[2]Ampicillin selection is done with 100 micrograms per milliliter of solid or liquid culture media.
[3]Tetracycline selection for pRK248cIts is 20 micrograms per milliliter of solid or liquid culture media. Tetracycline selection is not required for stable inheritance of pRK248cIts under non-inducing conditions, but is required when rhUG synthesis is induced.
[4]Ampicillin selection is not required for stable inheritance of pGELAC.
[5]The concentration of IPTG used to induce rhUG expression was 0.5 mM.
[6]Transcription from the λP$_L$ is induced by a rapid shift in the temperature of the culture from 32° C. to 42° C.. The temperature change causes a conformational change in the lambda repressor protein, also expressed from the pRK248cIts vector, that renders it unable to bind the λP$_L$ promoter. The bacterial RNA polymerase is then able to recognize the promoter and initiate transcription.
[7]The "A" signifies that the rhUG gene is in one orientation while the "B" signifies that it is in the opposite orientation, in the same BamH1 site.

One significant advantage of using pRK248cIts is that it is an oligo-copy number plasmid with a very stable origin of replication derived from RP4. Most high copy number vectors allow "leaky" protein expression in the uninduced state and are inherently less stable than lower copy number plasmids. Although pRK248cIts requires no selection for maintenance and stable inheritance of the plasmid in daughter cells, it bears antibiotic resistance genes for ampicillin and tetracycline. These antibiotics can be used for the convenient selection of bacterial transformants during clonings. However, plasmid stability is often impaired when high level expression of a recombinant protein encoded on the plasmid is induced. If an antibiotic is needed to maintain the plasmid during expression of a recombinant protein, then tetracycline could be used in biopharmaceutical production, which is permitted by the FDA.

The synthetic gene was also inserted into pGEL101 (Mantile, 1993) and pGELAC (Mantile, 2000). The expression of rhUG from the synthetic gene versus expression from the human cDNA sequence in these plasmids was compared and the synthetic bacterial gene yielded superior results.

The use of the par sequence (a 2.8 kb sequence derived from the broad host range R factor RP4) to stabilize plasmid inheritance has been described under chemostat conditions using ampicillin selection after a prolonged period of growth in the absence of antibiotic as the criterion for stability (Mantile, 2000). However, the process of the invention does not involve the use of chemostat conditions. Instead, the production strain (host/vector system) is required to undergo a series of seed banking processes, involving growth in the absence of ampicillin followed by a freeze-thaw cycle. Then the host/vector system must remain stable in the absence of ampicillin selection through a series of fermentations to reach a large cell biomass before induction of protein expression during which stable inheritance must be maintained so that maximum protein levels are achieved.

Production strain CG12 is a host/vector system containing a plasmid similar to pGELAC in *E. coli* strain BL21/DE3. This strain was tested for both genetic stability (at the level of DNA sequence) and plasmid stability in the absence of ampicillin selection. The following examples demonstrate that the host/vector system in production strain CG12 is stable in all respects throughout the production process, from seed banking to final harvest of the large scale induced fermentation culture.

Construction of a Separate Host-Vector System

The source of the UG protein coding sequence was cDNA generated from human lung mRNA. The cGMP expression system for recombinant human UG is similar to that described in Mantile et al. (Mantile, 2000; Mantile, 1993, Miele, 1990). The protein is expressed from a plasmid, called pCG12, using the T7 promoter and the T7 DNA-dependent RNA polymerase, which is under control of the IPTG-inducible lac promoter in the genome of the BL21/DE3 host strain. The expression vector, pCG12, codes for a protein with three additional amino acids at its N-terminus relative to the native human protein (an initiator methionine followed by two alanines). While these are necessary for efficient translation in bacteria the methionine is cleaved off during the fermentation process, resulting in a product comprising UG protein with two additional alanines at the N-terminus.

The pCG12 expression vector is suitable for cGMP manufacturing for several reasons. First, it lacks a requirement for antibiotic selection during fermentation. Although pCG12 can be selected using ampicillin, the antibiotic is not required to maintain stable plasmid inheritance during bacterial cell growth and propagation. Antibiotic-free stable plasmid inheritance was achieved through the use of a plasmid stabilization sequence called par. The par sequence is a 2.8 kilobase sequence that is derived from the broad-host-range R factor, RP4 (Gerlitz, 1990). Par modifies plasmid partitioning and significantly enhances plasmid stability. This sequence confers long term stability under chemostat conditions, for over 250 generations in the absence of antibiotic selection (Mantile et al., 2000). Second, pCG12 is genetically stable through the drug production process. Its DNA sequence does not change, despite cell banking which involves freezing and thawing steps that can break DNA. Third, it has been shown the par sequence confers plasmid stability in the absence of ampicillin selection, through the cell banking process, subculturing, and in batch fermentations.

FIG. 3 shows the arrangement of genetic elements in pCG12. This expression vector is similar to pGELAC (Mantile, 2000: Genebank accession number HSU01102). The bacterial host strain for expression of rhUG is BL21/DE3 (ATCC #47092). The 2.8 kilobase par sequence is derived from the broad-host-range R factor, RP4, which confers partitioning functions that enhance plasmid stability and, it has been shown that it confers plasmid stability throughout the production process, from cell banking to large scale fermentation.

EXAMPLE III

Preparation of a Research Seed Cell Bank

A research seed culture was inoculated from a single colony of BL21/DE3 containing pCG12 grown on LB agar containing 50 micrograms/ml of ampicillin. A research seed bank was generated from the 50 ml research seed culture grown at 32° C. in LB medium containing no antibiotic selection. The culture was grown to early stationary phase and glycerol was added to a final concentration of 20%. The culture was then frozen in 1 ml aliquots and stored at −75° C. Aliquots of this research seed were then used for fermentation development, as well as to generate master and working cell banks.

The pCG12 vector is genetically stable, such that the DNA sequence remains unchanged through the manipulations required to produce rhUG drug substance. The entire pCG12 plasmid was sequenced after cloning and prior to the creation of the research seed bank (SEQ ID NO: 9). Although pCG12 is stable in the absence of antibiotic, it does confer ampicillin resistance upon its bacterial host. The DNA sequence of the pCG12 plasmid recovered from fermentation production cultures is identical to the plasmid sequence from the research seed.

EXAMPLE IV

Preparation of Master and Production Seed Cell Banks

A master cell bank was prepared from research seed of strain CG12. A flowchart outlining the both the Master and Production cell banking processes is presented in FIG. 4. A list of the chemicals and materials used in the manufacture of the Master and Production seeds is provided in Table 3. All chemicals and materials were USP grade, in compliance with cGMP.

TABLE 3

Raw materials and Chemicals Used in Production of Master and Production Seed Cell Banks.

| Material/Chemical | Manufacturer | Grade |
| --- | --- | --- |
| Glycerol | J. T. Baker | USP/FCC |
| Yeast Extract | Difco | N/A |
| Tryptone | Difco | N/A |
| Sodium Chloride | J. T. Baker | USP/FCC |
| Water for Injection | WRAIR | USP |
| Research Cell bank (for Master Seed Production) | Claragen | cGLP |
| Master Cell bank (for Production Seed Production) | WRAIR | cGMP |

An aliquot of the CG12 research seed was added to a shake flask containing Luria Broth ("LB") and maintained at 32° C. with shaking, monitoring the growth by optical density (OD) from 550 nm to 660 nm, preferably at 600 nm. No antibiotic was used. Samples of broth were subsequently taken from the shake flask at approximately one hour intervals and the absorbance of each was measured and recorded until an $OD_{600}$ of 0.8 to 1.5 AU was reached. One hundred milliliters of the culture were then combined with 20 ml of the cryopreservative (glycerol) and a sample was retained for Gram staining to verify the identity and purity of the bacteria present in the culture. One milliliter of the culture was transferred aseptically to each of 90 labeled cryovials, which were placed into three labeled boxes each containing 30 vials. Two boxes were transferred to a freezer maintained at −80° C. and one box was transferred to liquid nitrogen for storage.

The production cell bank was then prepared from the master cell bank. The process for preparing the production cell bank was identical to that used in preparing the master cell bank, except that a vial from the master cell bank was used to start the culture in place of the research seed. Ninety cryovials, each containing one milliliter of the culture, were prepared and placed into three boxes each containing 30 vials. Two boxes were transferred to a freezer which was maintained at −80° C. and one box was transferred to liquid nitrogen for storage.

Each culture and cell bank was tested extensively and results documented to comply with cGMP guidelines. The growth curves of the master and production seed bank cultures showing the absorbance at 600 nm as a function of time are shown in FIG. 5. Both cultures reached logarithmic growth within a few hours and were harvested in mid-logarithmic growth. Samples for initial viability were taken at this time. Samples to test the viability of each bank were taken one week after the seed vials were frozen. Other tests and assays to qualify the banks for cGMP are described below. The results of these assays for the Master and Production seeds (Lots 0644 and 0645, respectively) are set forth in Tables 4 and 5, respectively. Both the Master and Production Seeds passed all specifications. The loss of five to ten percent of the cell viability was expected from the freezing of the cells.

The following assays were used in the characterization of the Master seed cell bank, the Production seed cell bank and the Fermentation.

Purity. LB plates were streaked using sterile techniques and were incubated at 37° C. Colonies were examined after 24 to 36 hours.

Viability. Cell viability was determined by plating serial dilutions of the cell culture on LB agar plates with or without ampicillin. Colonies were then counted and the results recorded.

Gram Staining. A small amount of the culture to be tested was transferred to a slide and the slide was allowed to air dry before being heat fixed. The fixed cells were then stained with crystal violet followed by Grams iodine. Cells were then examined under an oil immersion lens at 1000×. Control organisms are S. aureus and E. coli.

Colony Morphology. LB plates were streaked as described in the SOP and incubated as described. Colonies were examined after 24 to 36 hours.

Colony Appearance. LB plates were streaked using sterile technique and incubated at 37° C. Colonies were examined after 24 to 36 hours.

Optical Density. Cell density of the culture was determined by the absorbance from 550 m to 660 nm, preferentially at 600 nm using a LKB spectrophotometer.

SDS-PAGE. Samples for SDS-PAGE for the fermentation as well as for in process samples for the purification were run on 10–20% Tricine gels (Novex). Samples were mixed 1:1 (v:v) with 2× Tricine SDS-PAGE loading buffer (Novex) and run until the dye front was approximately 1 cm from the bottom of the gel. High or low molecular weight range size markers (Amersham) were used as standards. Gels were fixed by heating to at least 85° C. for 5 minutes in the presence of 10% acetic acid/30% methanol followed by staining with Gel Code Blue stain from Pierce Chemical Co. Destaining was performed in purified water as described by Pierce. Gels were then photographed and dried.

TABLE 4

Assay Summary Table for Master Seed Lot No. 0644

| Assay | Result |
|---|---|
| Purity-Final Culture | No Contamination |
| Initial Viability of Master Cell bank-LB Plates | 230 × 10$^6$ CFU/ml |
| Initial Viability of Master Cell bank-LB Plates + Ampicillin | 420 × 10$^6$ CFU/ml |
| Gram Stain | Gram (−) Rods without Contamination |
| 1 Week Post Manufacturing Viability of Master Cell bank-LB Plates | 85 × 10$^6$ CFU/ml |
| 1 Week Post Manufacturing Viability of Master Cell bank-LB + Ampicillin Plates | 67 × 10$^6$ CFU/ml |
| Colony Morphology-LB Plates | Creamy white single smooth colonies |
| Colony Morphology-LB + Ampicillin Plates | Creamy white single smooth colonies |
| Colony Appearance-LB Plates | Creamy White |
| Colony Appearance-LB + Ampicillin Plates | Creamy White |

CFU = Colony Forming Units

TABLE 5

Assay Summary Table for Production Seed Lot No. 0645

| Assay | Result |
|---|---|
| Purity-Final Culture | No Contamination |
| Initial Viability of Production Cell bank-LB Plates | 270 × 10$^6$ CFU/ml |
| Initial Viability of Production Cell bank-LB Plates + Ampicillin | 290 × 10$^6$ CFU/ml |
| Gram Stain | Gram (−) Rods without Contamination |
| 1 Week Post Manufacturing Viability of Production Cell bank-LB Plates | 77 × 10$^6$ CFU/ml |
| 1 Week Post Manufacturing Viability of Production Cell bank-LB + Ampicillin Plates | 50 × 10$^6$ CFU/ml |
| Colony Morphology-LB Plates | Creamy white single smooth colonies |
| Colony Morphology-LB + Ampicillin Plates | Creamy white single smooth colonies |
| Colony Appearance-LB Plates | Creamy White |
| Colony Appearance-LB + Ampicillin Plates | Creamy White |

CFU = Colony Forming Units

The Production seed cell bank is used to inoculate fermentations for production of rhUG and the Master seed cell bank is used to create new Production seed cell banks as they are used up. These two banks provide for a long-term qualified source of raw material, e.g. bacterial cell paste, from which to purify pharmaceutical grade rhUG.

EXAMPLE V

Fermentation

A list of the chemicals and equipment used in the fermentation are provided in Tables 6 and 7, respectively.

TABLE 6

Chemicals used in *E. coli* Fermentation for Production of rhUG

| Chemical | Manufacturer | Grade |
|---|---|---|
| Select APS Super Broth plus | Difco | N/A |
| Glycerol | J. T. Baker | USP/FCC |
| Isopropyl-β-D-thiogalactopyranoside | Sigma | N/A |
| Sodium Chloride | J. T. Baker | USP/FCC |
| Mazu DF 204 | Mazer Chemical | N/A |

TABLE 7

Equipment used in *E. coli* Fermentation for the Production of rhUG

| Equipment | Manufacturer | Model |
|---|---|---|
| 400 L Fermenter System | New Brunswick Scientific | IF-400 |
| Biological Safety Cabinet | Baker | B60-ATS |
| Continuous Feed Centrifuge | Sharples | AS-Z6SP |
| Shaker-Incubator | New Brunswick Scientific | Innova 4330 |
| pH meter | Orion | 420 |
| Spectrophotometer | LKB | N/A |
| Peristaltic pump | Cole-Parmer | 07523-40 |
| Overhead Mixer | Lightnin | MSV-1500 |

A flowchart outlining the fermentation process is presented in FIG. 6. To begin the fermentation process, a vial of the Production seed cell bank was thawed at room temperature. One hundred microliters of the production seed was then used to inoculate each of the six, fernbach flasks containing one liter each of sterile Super Broth medium (Becton-Dickinson Select APS Super Broth, glycerol and WFI). The cultures in the six flasks were then incubated at 32° C. in a New Brunswick shaker-incubator with agitation (300 rpm) for approximately 20 hours. The cultures in the six flasks were then used to inoculate 300 liters of Superbroth in a 400 liter New Brunswick Scientific Fermenter System (Model IF-400).

Preparation of the fermenter prior to inoculation was as follows: the fermenter was cleaned and sterilized according to standard operating procedures, and was then charged with 100 kg of WFI. Super Broth medium (Becton Dickinson Select APS Super Broth, glycerol and WFI) was added to the fermenter and additional WFI was added to reach a final, net weight of 300 kg. The fermenter was then pressure tested and sterilized at 122° C. for 30 minutes according to a standard operating procedure. Antifoam (Mazu DF 204) was added to the fermentation as required. The set point parameters for the fermentation are defined in Table 8.

TABLE 8

Fermentation Set Point Parameters

| Parameter | Set Point Range | Actual Set Point |
|---|---|---|
| Agitation | 150 ± 10 rpm | 150 |
| Temperature | 32 ± 2 C. | 31.9 |
| Air Flow | 300 ± 2 L/min | 299.8 L/min |

TABLE 8-continued

Fermentation Set Point Parameters

| Parameter | Set Point Range | Actual Set Point |
|---|---|---|
| Pressure | 3 ± 1 psig | 2.4 psig |
| Dissolved Oxygen | NA | ≥20% |

The shake flask inoculum is then added to the fermenter and the culture is grown at 25° C. to 40° C. until a minimum optical density at 600 nm of 2.0 was reached. On reaching a minimum $OD_{600}$ of 2.0 the expression of rhUG is induced by the addition of isopropyl-β-D-thiogalactopyranoside (IPTG) to the fermentation culture to a final concentration of 0.1 mM to 10 mM. The fermentation was maintained for at least one hour, preferably two hours post induction. The bacterial culture is harvested by centrifugation with a Sharple's continuous feed centrifuge. The cell paste is partitioned and stored frozen at −80° C. for later purification.

In the example shown, the six shake flask cultures used for the inoculation of the fermenter reached an average $OD_{600}$ of 2.8 after fourteen and a half hours and contained $210 \times 10^6$ colony forming units per milliliter. During the fermentation dissolved oxygen levels decreased in response to the increased cell metabolism and biomass between three and four hours into the fermentation. The agitation range was sufficient to maintain the dissolved oxygen at a minimum level of 20%. Expression of rhUG in the fermentation culture was induced after 4.2 hours (with an $OD_{600}$ of 2.7 and a cell count of $40 \times 10^6$ CFU/ml). Growth continued at log phase rates for a little over an hour post induction, cells were harvested after approximately 6 hours of fermentation (FIG. 7). Samples were taken from the culture after fermentation and were analyzed later by SDS-PAGE (FIG. 8). All other fermentation data is recorded in Table 9. The fermentation passed all specifications.

TABLE 9

Assay Results, E. coli Fermentation for the Production of rhUG Lot No. 0708

| Assay | Result |
|---|---|
| Sterility Check | No Growth |
| Gram Stain | Gram (−) Rods |
| SDS-PAGE | Comparable to Reference |
| Final Viability on LB | 160 × 10⁶ CFU/ml |
| Final Viability on LB-Ampicillin | 110 × 10⁶ CFU/ml |
| Purity of Final Samples | No Contamination |
| Final Colony Morphology | Creamy, Homogeneous, Noncontaminated, Single colonies |

CFU = Colony Forming Units

EXAMPLE VI

Purification of rhUG

Chemicals, supplies and equipment which were used in the purification of rhUG are shown in Tables 10 and 11.

TABLE 10

Chemicals and Supplies Used in rhUG purification Process

| Chemical/Supply | Manufacturer | Grade |
|---|---|---|
| Ethanol, USP-200 | Spectrum | USP |
| Tris Base(Hydroxymethyl)-aminomethane | Spectrum | USP/NF |
| Sodium phosphate, monobasic, monohydrate | J. T. Baker | USP/NFF |
| Sodium chloride | J. T. Baker | USP/NFF |
| Sodium Hydroxide (pellets) | Spectrum | NF/FCC |
| Hydrochloric acid (concentrated) | J. T. Baker | USP/NFF |
| Edetate, disodium, dihydrate | Spectrum | USP/NF |
| Copper sulfate, pentahydrate | J. T. Baker | USP |
| Macro Q 50 | BioRad | N/A |
| Type I Hydroxyapatite, 20μ | Biorad | N/A |
| Chelating SEPHAROSE ® Fast Flow | Pharmacia | N/A |
| 100K Ultrafiltration cartridge | Millipore | N/A |
| 5K Ultrafiltration cartridge(s) | Millipore | N/A |
| SARTOBIND ® Q cartridge | Sartorious | N/A |
| Size 15, 24 and 73 Silicone tubing | Sanitech | N/A |
| Size 73, Pharmed tubing | Cole-Parmer | N/A |
| Size 191, Bioprene tubing | Watson Marlow | N/A |
| Millipak 20, 60, 100 and 200 sterile 20μ filters | Millipore | N/A |
| E. coli Cell paste | WRAIR | cGMP |

TABLE 11

Instruments and Equipment Used in rhUG Purification Process

| Item | Supplier | Model Number |
|---|---|---|
| Pellicon 2 Cassette Filter | Millipore | Pellicon 2 |
| Stainless Steel Holder(s) | | |
| Lab Masters SI mixer | Lightnin | N/A |
| Spectrophotometer | Shimadzu | UV 160 |
| Vantage A column(s) | Amicon | 18.0 × 50 cm |
| Vantage A column | Amicon | 13.0 × 50 cm |
| Balance | Sartorius | 14800p |
| Variable Speed Peristaltic Pump, I/P | Millipore | XX80EL0-00 |
| Masterflex L/S pump(s) | Cole-Parmer | G-07523-20 |
| Peristaltic Pump | Watson Marlow | 701 S/R |
| Super Speed Centrifuge(s) | Sorvall | RC-5B/RC-5C |
| High Speed Rotor | PTI | 14C |
| Fluidizer | Microfluidics | M-110F |
| 142 mm Stainless Steel holder | Sartorius | 16276-3 |
| UV Monitor | Pharmacia | Uvicord SII |
| chart Recorder | Pharmacia | Rec I |
| Conductivity Meter | Orion | 162 |
| pH Meter System | Orion | 620 |

Batches of rhUG having common biological activities and physical and chemical specifications were purified by minor variations of the same process two of which followed cGMP guidelines for pharmaceutical production. Two of the processes, one of the cGMP purification processes and one process used for the production of rhUG for animal studies, are outlined in FIG. 11. Descriptions of these processes and of several variations used in both cGMP processes and in the production of rhUG for animal studies are as follows. For the cGMP process outlined in FIG. 11*b*, one kilogram of bacterial cell paste was lysed by shear and the cell debris removed by centrifugation. The lysate (supernatant) was then processed using a 100 K nominal molecular weight cut off (NMWCO) membrane in a tangential flow filtration (TFF) system. The permeate from the 100 K step was concentrated by TFF using a 5 K NMWCO membrane and loaded onto a Macro Q anion exchange column. The eluate from the anion exchange column was concentrated and diafiltered by TFF using a 5 K NMWCO membrane before being loaded onto a Type I Hydroxyapatite (HA) column.

The eluate from the HA column was then loaded directly onto a column packed with Chelating SEPHAROSE® Fast Flow (CSFF) resin with copper as the chelate. The rhUG passed through the column while the host-derived proteins present in the HA eluate bound to the column. A positively charged SARTOBIND® Q TFF membrane was also placed into the flowstream after the copper CSFF column to ensure that the maximum amount of endotoxin was removed from the final bulk material. The pass-through from the SARTO-BIND® Q was concentrated and then extensively diafiltered using a 5 K NMWCO membrane with saline for injection (SFI) as the replacement buffer, both to remove residual copper as well as to properly formulate the final bulk material.

This process and minor variations thereof were used both for a separate cGMP clinical lot as well as in lots used for animal testing. These variations include: 1) use of either a 30 K NMWCO membrane or a 50 K NMWCO membrane in place of the 100 K NMWCO membrane for separation of rhUG from other proteins in clarified the bacterial lysate; 2) filtration of the HA eluate through a 30 K NMWCO TFF membrane rather than processing by Copper bound CSFF column chromatography; and 3) removal of the SARTO-BIND® Q membrane after the copper bound CSFF chromatography. The final step in the purification of a five to twenty volume diafiltration against saline using a 5 K NMWCO membrane was used in all cases.

These methods produced rhUG with comparable physical characteristics and is sufficient to meet the FDA's cGMP manufacturing requirements and requirements for use of rhUG in animal studies. The rhUG preparations made by this process, and minor variations thereof, are comparable in all respects: apparent size, molecular weight, charge, N-terminal amino acid sequence, amount of free thiol indicating correct formation of cystine—cystine bonds, immunological recognition techniques such as ELISA and Western blotting, and biological activity. Protein purified using the copper CSFF column was tested for the presence of copper by Inductively Coupled Plasma (by QTI Inc.). No copper was detected and the detection limit of the assay was 0.5 ppm. This translates into a maximal dose of 1 µg per 2 ml dose, which is well below the estimated safe and adequate daily dietary intake of 600 µg per day for infants (Olivares, 1996).

Columns were packed using standard operating procedures and according to the column and resin manufacturers' recommendations. All packed columns were sanitized with 0.5 M sodium hydroxide for a minimum of 30 minutes and placed into their respective storage solutions until use. The membranes for the tangential flow filtration were sanitized and depyrogenated with 0.5 M sodium hydroxide at 45±5° C. for a minimum of one hour prior to use. The SARTO-BIND® Q membranes were sanitized and depyrogenated with 1.0 N NaOH for a minimum of 30 minutes prior to use.

Flowcharts showing the steps in embodiments of the purification process are presented in FIGS. 10 through 16. One kilogram of frozen cell paste from the fermentation was thawed at room temperature and lysed by shear using either a MICROFLUIDIZER® (a device to rupture cells) (Microfluidics) or a similar shear device. The resulting crude lysate was clarified by centrifugation at 15,000×g. The clarified cell lysate was purified by constant volume diafiltration in 25 mM Tris/40 mM NaCl pH 7.0 using a 100 K NMWCO membrane. The permeate from the 100 K TFF step was collected and concentrated using a 5 K NMWCO membrane with 25 mM Tris/40 mM NaCl pH 7.0. After concentration of the 100 K permeate a 5× constant volume diafiltration was performed with 25 mM Tris/40 mM NaCl pH 8.5 to remove low molecular weight impurities and to change the 100 K TFF buffer with Macro Q Anion exchange equilibration buffer to produce the 5K Ret #1 (FIG. 10). This was then loaded onto a three liter Macro Q anion exchange column. Non-bound and weakly bound proteins were washed from the column and the fraction containing the rhUG was eluted with 25 mM Tris, 150 mM sodium chloride, pH 8.5 (FIGS. 11a and 11b). The eluate from the Macro Q column was concentrated and the buffer was simultaneously exchanged with the equilibration buffer for the HA column using a 5 K NMWCO membrane to produce the 5K Ret. #2 (FIG. 12). The 5K Ret. #2 was loaded onto a three liter Type I Ceramic Hydroxyapatite column. Non-bound proteins were washed from the column with 10 mM Sodium Phosphate pH 7.0 and the fraction containing the rhUG was eluted with 75 mM sodium phosphate, pH 7.0 (FIGS. 13a and 13b). The eluate from the HA column was loaded directly onto a one liter Chelating SEPHAROSE® Fast Flow (CSFF) column charged with copper. The rhUG did not bind to the copper CSFF column and was retrieved in the flowthrough (FIGS. 14a and 14b). The flowthrough from the copper CSFF column was then diluted one to one with WFI and passed through a SARTOBIND® Q filter as a final endotoxin removal step (FIG. 15). The passthrough from the SARTO-BIND® Q membrane was concentrated using a 5 K NMWCO TFF membrane. After concentration, a 20× constant volume diafiltration was performed with Saline for Injection as the replacement buffer (FIG. 16). The diafiltered material was then further concentrated to a minimum protein concentration of 7.5 mg/ml, filtered and diluted with Saline for Injection (SFI; 0.9% NaCl) to a target concentration of 5.5 mg/ml. The rhUG was then sterile filtered to generate the Purified rhUG Bulk Drug.

The following assays were established as in process assays, characterization assays and release assays for the production process and for the drug substance and drug product. The rhUG drug substances and drug products were compared to standard research lot rhUG/7 where appropriate.

Western Blot. Two Western blots were performed, one with α-rhUG antibody and one with α-*E. coli* lysate antibody (both from Dako, USA). The α-rhUG Western was performed using a rabbit polyclonal antibody to human UG with goat α-rabbit IgG-HRP conjugate from DAKO as the secondary antibody. The α-*E. coli* Western was performed with rabbit α-*E. coli* lysate polyclonal antibody followed by a goat α-rabbit IgG-HRP conjugate as the secondary antibody, both antibodies for the α-*E. coli* assay were obtained from DAKO. Detection was performed using the ECL™ (a signal amplification method) kit from Amersham.

Bacterial Nucleic Acids. Bacterial DNA content per dose of the rhUG drug substance and drug product was determined by Southern blot using radiolabeled bacterial DNA followed by hybridization to blotted concentrated rhUG sample (Charles River Laboratories-Malvern).

Mass Spectroscopy. The molecular weight was determined by Electrospray Ionization spectrometry by M-Scan Inc. Theoretical molecular weight was determined by PAWS (a shareware program for the determination of average molecular mass, obtained through Swiss Pro). A value of 16110.6 Da was determined by the PAWS program. The same value was found for cGMP batches of rhUG and was confirmed by MS analysis of standard research lot rhUG/7 as a control (determined molecular weight 16110.6 Da).

N-terminal Sequence analysis. The sequence of the N-terminus was carried out using pulsed phase N-terminal sequencing on an Applied Biosystems (ABI) 477A automatic protein sequencer. The analysis was performed by M-Scan Inc. A sequence of Ala-Ala-Glu-Ile (SEQ ID NO: 10) was confirmed for cGMP batches of rhUG with standard research lot rhUG/7 as a control.

pH. A three-point calibration (4.0, 7.0, 10.0) is performed according to the manufacturers' instructions. After calibration of the electrode the pH of the sample is determined.

Isoelectric Focusing. The pI was determined by isoelectric focusing using gels with a pH range of 3 to 7. The gels were obtained from Novex and were run under conditions as described by the manufacturer. Samples were run versus a standard from Sigma and a rhUG control (research lot rhUG/7). Gels were fixed by heating in a microwave for 1 minute in the presence of 10% acetic acid/30% methanol followed by staining with Gel Code Blue stain from Pierce. Destaining was performed in purified water as described by Pierce.

Free Thiol. The presence of free thiol was determined by reaction with Ellman's reagent from Pierce using a modified proticol to increase sensitivity. After incubation in the presence of Ellman's reagent the absorbance of samples was determined in the spectrophotometer at 412 nm. An extinction coefficient of 14150 $M^{-1}$ $cm^{-1}$ was used to determine the molar amount of free thiol. A standard curve of free thiol (cysteine) was used to monitor the linearity of the reaction.

LAL. The presence of bacterial endotoxin in rhUG process intermediates, drug substance and drug product was tested by the *Limulus* ameobocyte lysate assay as described in United States Pharmacopeia (USP) Assay No. 85. Kits were obtained from Associates of Cape Cod.

Color, Appearance, Homogeneity. The bulk drug product was visually inspected for clarity, color and visible particulate matter.

Immunoreactivity. A competitive ELISA was performed using an antibody raised to native human UG isolated from urine (DAKO, α-urine protein-1) as the capture reagent and a rhUG-HRP (horseradish peroxidase) conjugate to compete with the rhUG in the sample. The antibody was coated at a dilution of 2,500 onto microtiter wells (100 microliters/well) in a 0.1 M carbonate/bicarbonate buffer at pH 9.5 overnight. The wells were dried and stored at 4° C. until use. The rhUG-HRP conjugate was made using a kit from Pierce. Approximately 250 nanograms of the rhUG-HRP conjugate in 250 microliters of phosphate-buffered saline (PBS) was used per well. A standard curve for each set of samples was run using rhUG calibrators (research lot rhUG/7), ranging from 0–500 nanograms/ml (shown in FIG. 17). All calibrators and test samples were run in duplicate. The UG in the sample competes with the rhUG-HRP conjugate for antibody binding sites in the wells. Thus, the assay signal decreases with increasing amounts of UG in the sample. The results were visualized by the o-phenyldiamine dihydrochloride (OPD) HRP assay by Pierce. Plates were read at 490 nm using a Biotek EL-80 microplate reader and the data were analyzed using Biotek KC4 software.

Purity and Identity: Reducing SDS PAGE. The rhUG drug substance and drug product was run on a Novex 10–20% Tricine SDS-PAGE gel under both reducing and non-reducing conditions as described by the manufacturer. Low molecular weight size standards were obtained from Amersham. Gels were fixed by heating in a microwave for 1 minute in a mixture of 10% acetic acid/30% methanol and stained with brilliant blue R250 (0.5%, w/v). Gels were destained with Novex Gel-Clear destaining solution as described by the manufacturer. Gels were then dried using the Novex Gel-Dry system and the percent purity was determined by scanning the gel (Hewlett-Packard scanner Model 5100C) and densitometry was performed using Scion Image shareware from the NIH.

Aggregation Assay. The drug product was analyzed for the presence of aggregates by chromatography on either a Superose 12 or a Sephadex 75 size exclusion chromatography (SEC) column (Amersham/Pharmacia). The column was run according to the manufacturer's instructions using the BioRad Biologic system and peak area was determined using EZLOGIC™ Chromatography Analysis software (chromatography system software), also from BioRad. The percent aggregation was determined by comparing the total area of all peaks vs. the area of peaks eluting prior to the main UG peak.

Endotoxin. Endotoxin levels were tested by the rabbit pyrogenicity assay as described in the U.S. Pat. No. 151. An amount of rhUG equivalent to a single human dose was administered intravenously over a 10 minute period. Body temperature increase relative to the baseline pre-dose temperature was monitored over the course of three hours. Acceptable results consist of no temperature rise equal to or greater than 0.5° C. over the baseline results.

Protein Content. The protein contents of the process intermediates, drug substance and product were determined by the absorbance at 280 nm using a Shimadzu 120 and an extinction coefficient of 2070 $M^{-1}$ $cm^{-1}$ as determined by Mantile et al. (Mantile, 1993).

Sterility. The sterility assay was performed as described in the U.S. Pat. No. 71. Samples were incubated into Fluid Thioglycolate Media (FTM) and Tripticase Soy Broth (TSB). Positive controls for TSB media were *C. albicans*, *A. niger*, and *B. subtilis*. Positive controls for FTM were *S. aureus*, *P. aeruginusa*, *C. sporogenes*.

Potency Assays. There are several biological activities attributed to UG throughout the literature on the human protein and its mammalian homologues. The biological activities that are associated with preparations of human rhUG that are prepared according to the described production process are described herein and in U.S. Ser. Nos. 08/864,357, 09/087,210, 09/120,264, and 09/549,926.

Certain biological activities of UG can be measured in vitro with available reagents and are relevant to the treatment of certain diseases. Two of these activities have been verified for UG as described herein. The first is an anti-inflammatory effect arising from inhibition or blocking of secretory phospholipase $A_2$ enzymes (s$PLA_2$s) by rhUG. We have confirmed that rhUG significantly inhibits human s$PLA_2$ enzymes in vitro, specifically the Type Ib enzyme found in the pancreas and lung, as well as the Type IIa enzyme produced by macrophages and found in human rheumatoid synovial fluid. A novel fluorescence-based HPLC assay for the inhibition of s$PLA_2$-Ib activity by rhUG was developed and has been used in conjunction with a more standard $^{14}$C-labeled assay. A second biological activity for rhUG is its ability to bind to fibronectin which prevents inappropriate deposition and the subsequent formation of a pro-fibrotic extracellular matrix in a transgenic knockout mouse model of UG deficiency (Zhang, 1997). A novel in vitro ELISA-type assay using human fibronectin to measure this activity of rhUG was developed.

These two potency assays can be used to gauge the relative strengths of the in vivo biological activities of future batches of rhUG. Because production processes, whether chemical or biological, are inherently variable, potency assays are essential in assessing potential safety and efficacy. The relative strength of the biological activity may be determined by the potency assays.

Inhibition of Secretory PLA$_2$- Type Ib

The potency assay is based on the inhibition of rhPLA$_2$ activity by the addition of rhCC10. RhPLA$_2$ catalyzes cleavage of the ester at the 2 position of L-3-phosphatidylcholine. Two different assays were employed to measure this activity; one uses as a substrate, 1-stearoyl-2-[1-$^{14}$C]arachidonyl phosphotidyl choline (Amersham) to produce [1-$^{14}$C]arachidonic acid (Product), which was then separated by liquid-liquid separation and and the level of cleavage determined by scintillation counting (PLA$_2$ Assay No. 1). The second was performed using a fluorescently labeled substrate, 2-decanoyl-1-(O-(1-(4,4-difluoro-5,7-dimethyl-4-bora-3a,4a-diaza-s-indacene-3-propionyl)amino)undecyl)-sn-glycero-3-phosphocholine (Molecular Probes). As shown in FIG. 18, the uncleaved substrate was separated from the cleaved substrate using normal phase HPLC, quantitation was performed using an in line fluorescence detector (PLA$_2$ Assay No. 2). Both assays were performed in Hanks Balance Salt Solution with 1 mM CaCl$_2$ in a final assay volume of 100 µL. RhPLA$_2$ was obtained from Dr. Won Hwa Cho's laboratory at the University of Illinois-Chicago. The novel PLA$_2$ Assay No. 1 assay was performed as follows. RhPLA$_2$ is added to all tubes to a final concentration of 200 nM. For inhibition assays rhCC10 was added to a final concentration of approximately 34 uM, an equal volume of HBSS was added to the control tubes. All tubes were preincubated for 20 minutes at 37° C., the assay was initiated by the addition of the radiolabeled phosphotidylcholine to a final concentration of 5 µg/ml. The reaction was then stopped after 15 minutes by the addition of a 7.7 fold dilution of Doles reagent and purified water (84:16). All tubes were vortexed and then centrifuged to separate the hydrophobic and the hydrophilic layers. The top layer was then removed and added to an Eppendorf tube containing 15 mg of silica gel, mesh size 60 to 200, and 800 µl of hexane for scintillation counting.

The novel PLA$_2$ Assay No. 2 was performed as follows. RhPLA$_2$ was added to all tubes to a final concentration of 200 nM. For inhibition assays rhCC10 was added to a final concentration of approximately 34 uM, an equal volume of saline was added to the control tubes. All tubes were preincubated for 20 minutes at 37° C., the assay was initiated by the addition of fluorescent labeled phosphotidylcholine to a final concentration of 5 µg/ml. The reaction was stopped after 15 minutes by the addition of a one to five dilution of 2-Propanol:n-hexane (8:3). One hundred µl of the stopped assay was loaded directly onto a silica normal phase HPLC column. The mobile phase for the system is 2-propanol:n-Hexane:water (8:3:2). The amount of cleaved substrate was determined by fluorescence with excitation at 480 nm and emmision at 517 mm.

The percent inhibition for each assay was defined as:

% Inhibition=(1−(Substrate cleaved in the presence of rhCC10÷substrate cleaved in the absence of rhCC10))×100.

TABLE 12

Inhibition of sPLA2 by Different Lots of rhUG

| Assay | RhUG Lot Numbers | | | |
|---|---|---|---|---|
| | CC10/6 | CC10/7 | CC10/8 | 0728 |
| PLA$_2$ Inhibition Assay #1: Radiolabel Assay | 48% | 38% | 54% | 58% |
| PLA$_2$ Inhibition Assay #2: Fluorescence Assay | 59% | 56% | 69% | 76% |

Binding to Human Fibronectin

A second biological activity for rhCC10 is its ability to bind to fibronectin, which prevents inappropriate deposition and the subsequent formation of a pro-fibrotic extracellular matrix in a transgenic knockout mouse model of CC10 deficiency (Zhang, 1997). A novel in vitro ELISA-type assay was developed using a recombinant 7 kDa fragment of human fibronectin (Fn III.1, also known as fragment-III$_1$-C, referred to as "rhFn") to measure this activity and this assay was used to monitor biological activity of rhCC10. Microtiter plates were coated with the fibronectin fragment overnight and binding of rhCC10 was detected by competition with a rhCC10-HRP (horse radish peroxidase) conjugate. RhCC10-HRP conjugate was added to the plates and allowed to incubate for 1 hour at room temperature. The conjugate may be added with or without standard or sample. PBS was used as a negative control. The plate was aspirated and washed four times. The assay was visualized by the o-phenyldiamine dihydrochloride (OPD) HRP assay from Pierce. The plate was read at 490 nm using a Biotek EL-80 microplate reader and the data was analyzed using Biotek KC4 software. FIG. 19 shows a typical standard curve for this assay. The results of this assay for all research and cGMP lots of rhUG were positive for binding of rhUG to the fibronectin fragment.

In addition to the extensive testing and characterization of the drug substance and drug products, samples of intermediates were taken throughout the process to follow the purification and determine the efficiency of each step. The process intermediates were analyzed by SDS-PAGE, rhUG ELISA, LAL and for protein content. Protein content was determined with a BCA assay from Pierce using bovine serum albumin as a standard. All buffers were analyzed for endotoxin content by the LAL assay. No endotoxin was detected in the buffers.

The purification process was analyzed for both overall and step recovery (Table 13). Overall purification, as determined from the 100 K Bulk, was 51.9 percent. Purity as described by Specific Activity was also examined (Table 14). Specific Activity is defined as the value for the UG ELISA divided by the value for the BCA protein assay for a defined sample. The largest amount of impurities removed occurs in the 100 K diafiltration step and in the subsequent Macro Q, anion exchange step. This is confirmed by the data from the SDS-PAGE results (FIGS. 20a and 20b). The Hydroxyapatite and Copper Chelating SEPHAROSE® Fast Flow columns are required to remove the final E. Coli protein impurities. Recoveries which exceed 100 percent and specific activities which exceed 1.00 are due to variability within the assays and to the different standards used.

Endotoxin levels were followed throughout the purification by the LAL assay. Endotoxin was 2400 EU/ml (total amount was 11×10$^6$ EU) in the 5K Retentate #1. After the material had been further purified on the Macro Q column, the endotoxin concentration had fallen to 0.17 EU/ml in the 5K Retentate #2 (volume=4000 ml) for a total of 680 EU. This represents a 16,000-fold decrease in the endotoxin level. Endotoxin levels were undetectable throughout the remainder of the purification.

TABLE 13

Recovery of RhUG from Purification Lot 0726

| Step | Volume (ml) | RhUG (mg/ml) | Total rhUG (mg) | Overall Recovery (%) | Step Recovery (%)[1] |
|---|---|---|---|---|---|
| Supernatant lysed Cells | 3990 | 6.45 | 25700 | 100 | N/A |
| 5K Ret #1 | 4780 | 4.67 | 22300 | 86.7 | 86.7 |
| Macro Q Eluate | 10000 | 2.10 | 21000 | 81.6 | 94.1 |
| Hydroxyapatite Eluate | 4000 | 4.37 | 17500 | 67.9 | 83.2 |
| Chelating SEPHAROSE ® Pass Through | 4250 | 3.57 | 15200 | 58.9 | 86.8 |
| SARTOBIND ® Q Pass Through | 9200 | 2.20 | 20200 | 78.6 | 134 |
| Purified rhUG Bulk | 2474 | 5.40 | 13400 | 51.9 | 66.0 |

[1]Step Recovery is defined as the recovery for each step.

TABLE 14

Specific Activity of rhUG from lot 0726

| Step | rhUG (mg/ml) | Protein (mg/ml) | Specific Activity |
|---|---|---|---|
| Supernatant lysed Cells | 6.45 | 22.1 | 0.292 |
| 5K Ret. #1 | 4.67 | 4.94 | 0.945 |
| Macro Q Eluate | 2.10 | 1.19 | 1.77 |
| Hydroxyapatite Eluate | 4.37 | 2.41 | 1.81 |
| Chelating SEPHAROSE ® Pass Through | 3.57 | 2.23 | 1.60 |
| SARTOBIND ® Q Pass Through | 2.20 | 0.89 | 2.48 |
| Purified rhUG Bulk | 5.40 | 3.08 | 1.75 |

The final, sterile filtered bulk Drug Substance passed all criteria as shown in Table 15.

TABLE 15

Specifications and Results for rhUG Drug Substance Lot 0726

| Test | Specification | Results |
|---|---|---|
| Color | Clear, colorless | Clear, colorless |
| Appearance | No turbidity | No turbidity |
| Homogeneity | Homogeneous | Homogeneous |
| Immunoreactivity | Positive reaction | Positive reaction |
| Purity | ≧95% | 98.3% |
| Aggregation | ≦5% | 0.18% |
| Endotoxin by Rabbit pyrogenicity | Satisfactory | Satisfactory |
| Protein content | 5.5 ± 0.5 mg/ml | 5.5 mg/ml |
| Sterility | Sterile | Sterile |
| Biological activity | Positive | Positive |
| Western blot | | |
| α-rhUG | Consistent with rhUG results from SDS-PAGE | Consistent with rhUG results from SDS-PAGE |
| α-E. coli | One light band at ~40 k | One light band at ~40 kD |
| Bacterial nucleic acids | <100 pg/dose | <7.5 pg DNA/dose |
| Mass spectroscopy | App. 16110 | 16111.9 kDa |
| PH | 5–8 | 6.30 |
| Isoelectric focusing | App. 4.7 | 4.7 |
| Free Thiol | <10% (w/w) | Not detectable. |
| LAL | <5 EU/mg | <0.01 EU/mg |
| N-terminal Sequencing | A-A-E-I | A-A-E-I1 |

[1]Both MAAEI and AEI forms were less than 0.062% of the total.

Due to the structure of rhUG both the dimer and the monomer run at a lower molecular weight on SDS-PAGE than would be predicted by the sequence molecular weight (FIG. 21). Another characteristic of the protein is that separation of the dimer into monomers in the presence of reducing agents is not complete, as can be seen by the presence of residual dimer in lanes 5 and 9 of the Coomassie-stained SDS-PAGE gel (FIG. 21) and in lane 5 of the α-UG Western (FIG. 22). While rhUG is apparent at both the dimer and monomer positions of lane 5 of the α-rhUG Western (FIG. 22), there was no E. coli protein detectable in either the monomer or the dimer position in lane 3 of the α-E. coli Western (FIG. 23). The only visible band in lane 3 of the α-E. coli Western has an apparent molecular weight of approximately 40 kD (FIG. 23).

Another characteristic of rhUG is the formation of a small quantity of aggregates, as is apparent in lane 11 of the Coomassie-stained gel (FIG. 21) where the higher molecular weight bands corresponded well with higher molecular weight bands in lane 2 of the α-rhUG western (FIG. 22). Both the dimer and the aggregates appear to react more strongly with the α-rhUG antibody than the monomer, consistent with observations made during the development of the UG ELISA. Analysis of aggregates at 214 nm by size exclusion chromatography indicates minimal formation of rhUG aggregates as compared to the overall amount of dimer (Table 15).

The isoelectric point for rhUG was determined to be 4.7 using an IEF gel (FIG. 24). The results were confirmed by submission of the amino acid sequence to Swiss Pro (www.expasy.ch), the calculated pI(4.7) was the same as the observed pI.

EXAMPLE VII

Stability of Drug Substance

The exemplary Drug Substance and the exemplary Drug Product are at the same concentration and in the same formula (i.e. no excipients are added). Stability was tested on the Drug Product.

Formulation and Packaging of the Drug Product

All materials, chemicals and equipment used in the final fill of the exemplary Drug Product are listed in Tables 16 through 18.

TABLE 16

Materials used in the Final Fill of the Drug Product

| Item | Manufacturer |
|---|---|
| 2 ml vials | Wheaton |
| V-35 13mm Stoppers | West |
| 13mm Aluminum Crimp Sealers | Wheaton |
| 2 mm Tubing Assembly | Wheaton |
| Forceps - 6" | N/A |
| Aluminum Foil | N/A |
| 600 ml Beaker | Kimax |

TABLE 17

Chemicals used in the Final Fill of the Drug Product

| Chemical | Manufacturer |
|---|---|
| Bulk rhUG | WRAIR |
| Sterile 70% Isopropanol | Veltrek |

TABLE 18

Equipment used in the Final Fill of the Drug Product

| Equipment | Manufacturer |
|---|---|
| Balance | Sartorius |
| Omnispense | Wheaton |
| Crimper | Kebby |

The composition of an exemplary embodiment of the Drug product is: rhUG at 5.5 mg/ml, and sodium chloride at 0.9% (w/v). All filling operations were performed in a Class 100 environment room. Both the room and the operations for fill were validated by the operator. An Omnispense pump was set up with 2 mm tubing, primed and set to fill to a weight of 2.0 g±5% (1.90–2.10 ml). A flowchart outlining the fill processes is shown in FIG. 25. A two ml vial was tared and bulk rhUG was dispensed into the vial. After filling, the weight of the vial was recorded. This procedure was repeated two times. If the fill weights of the three vials were all within the specified range, then all of the vials were filled. If a vial fell out of the specified range, the dispenser volume was adjusted and the process was repeated. After filling, vials were stoppered manually and aluminum crimp seals were placed onto the vials. The vials were crimped using a Kebby Power Crimp. Vials were then labeled and inspected visually. The rhUG drug product produced in this manner provides a clear, colorless solution with no visible particulates.

Summary of Physical and Chemical Characteristics of the Drug Product

RhUG (SEQ ID NO: 11) is a dimeric protein with a molecular weight of 16110 kilodaltons as calculated from the amino acid sequence and confirmed by electrospray mass spectroscopy. The protein is composed of two subunits bound to one another by two cystine bonds. Relative subunit molecular weight and the presence of the cystine bonds has been determined by SDS-PAGE under reducing and non-reducing conditions. The DNA sequence of the bacterial strain, CG12, was confirmed as was the amino acid sequence of the N-terminus of the protein by Edman degradation. The sequence of the N-terminus was Ala-Ala-Glu-Ile as predicted (SEQ ID NO: 10). Cysteine is not readily detected by this method both due to the inherent chemistry and to the fact that the cysteine is involved in sulfur bonding.

The final, vialed rhUG drug product passed all specification as shown in Table 20.

TABLE 19

Specifications for rhUG Drug Product Lot 0728

| Test | Specification | Results |
|---|---|---|
| Color | Clear, colorless | Clear, colorless |
| Appearance | No turbidity | No turbidity |
| Homogeneity | Homogeneous | Homogeneous |
| Purity | ≧95% | 97.4% |
| Aggregation | ≦5% | 2.25% |
| Endotoxin | Satisfactory | Satisfactory |
| Protein content | 5.5 ± 0.5 mg/ml | 5.5 mg/ml |
| Sterility | Sterile | Sterile |
| Biological activity | Positive | Positive |
| Western blot | | |
| α-rhUG | Consistent with rhUG results from SDS-PAGE | Consistent with rhUG results from SDS-PAGE |
| α-E. coli | One light band at ~40 k | One light band at ~40 kD |
| Bacterial nucleic acids | <100 pg/dose | <1.6 pg DNA per mg rhUG |
| Mass spectroscopy | App. 16110 | 16112.6 |
| pH | 5–8 | 6.82 |
| Isoelectric focusing | App. 4.7 | 4.7 |
| Free Thiol | <10% (w/w) | Not Detected |
| LAL | <5 EU/mg | <0.01 EU/mg |
| N-terminal Sequencing | A-A-E-I | A-A-E-I[1] |
| Copper | <16 μM | <16 μM |

[1]Both MAAEI and AEI forms were less than 0.062% of the total.

As was described for the Drug Substance, both the dimer and the monomer of the Drug Product run to a lower molecular weight on SDS-PAGE than would be predicted by the sequence molecular weight (FIG. 26). Separation of the dimer into monomers of the Drug Product in the presence of reducing agents was not complete as demonstrated by the presence of residual dimer in lanes 5, 9, and 11 of the Coomassie gel (FIG. 26) and in lane 6 of the α-rhUG Western (FIG. 27). While rhUG is apparent at both the dimer and monomer positions of lane 6 of the α-rhUG Western (FIG. 27), there was no E. coli protein detected in either the monomer or the dimer position in lane 4 of the α-E. coli Western (FIG. 28). There were no bands visible in lane 4 of the α-E. coli Western (FIG. 28).

Aggregates were also apparent in lane 3 of the α-UG Western (FIG. 27). Both the dimer and the aggregates appear to react more strongly with the α-UG antibody than the monomer; this was also observed in the development of the UG ELISA. Analysis of aggregates at 214 nm by size exclusion chromatography indicates minimal formation of rhUG aggregates as compared to the overall amount of dimer (Table 19).

The isoelectric point for rhUG was determined to be 4.7 using an IEF gel (FIG. 29). The results were confirmed by submission of the amino acid sequence to Swiss Pro, the calculated pI was the same as the observed pI.

All pre-clinical development lots made for animal testing were analyzed using similar techniques as used for the cGMP lots. Ranges for critical parameters for the rhCC10 are presented in Table 20. Other critical parameters such as pI, molecular weight, N-terminal end sequence and free thiol were essentially identical for all lots of rhUG.

TABLE 20

Ranges for development lots rhCC10/6, rhCC10/7, rhCC10/8, and cGMP lots 0728 and 0853.

| Assay | Range of results |
|---|---|
| Purity | 97.4% to >99.5% |
| Aggregation | 0.13% to 3.4% |
| PLA$_2$ Inhibition (Radioactive assay) | 37.5% to 57.7% |
| PLA$_2$ Inhibition (Fluorescent assay) | 56.0% to 86.0% |

The final Drug Product passed all release criteria and was identical to the material used in the animal studies and would be acceptable for use in a Phase I/II human clinical trial by the U.S. FDA.

Stability of rhUG Preparations

Long term stability studies on purified rhUG preparations, a developmental lot (GLP material; lot number rhUG/7 stored at 2–8° C.) and a pharmaceutical grade manufacturing lot (drug product lot number 0728 stored at 2–8° C.), were carried out for 18 and 15 months, respectively and for 7 months for accelerated aging of a pharmaceutical grade manufacturing lot (drug product lot number 0728 stored at 25° C. and 60% Relative Humidity). At specified times a vial of each was removed from storage at 2–8° C. and tested. Assays are described in Table 21.

TABLE 21

Assay performed for Stability Assessments

| Test | Specification |
|---|---|
| Purity (Reduced SDS PAGE) | ≧95% |
| Aggregation | ≦5% |
| Biological activity | Positive |
| Isoelectric focusing | App. 4.7 |
| Free Thiol | <10% |

Results for the assays for the research lot are presented in Table 22 and assay results for the cGMP lot are shown in Table 23 (2–8° C.) and Table 24 (25° C. and 60% RH).

TABLE 22

Results of Stability Tests on Development Lot

| | | Time in Months | | | | |
|---|---|---|---|---|---|---|
| Test | Spec | 0 | 1 | 2 | 3 | 4 |
| Purity | ≧95% | >99.5%[1] | >99.5% | >99.5% | >99.5% | >99.5% |
| Aggregation | ≦5% | 0.6 | 2.7 | 0.3 | 1.2 | 0.42 |
| PLA2 (14C) | + | ANA[2] | ANA | ANA | ANA | ANA |
| PLA2 (HPLC) | + | ANA | ANA | ANA | ANA | ANA |
| Fibronectin (Fragment) | + | na | na | na | + | na |
| Isoelectric Focusing | App. 4.7 | 4.7 | 4.7 | 4.7 | 4.7 | 4.7 |
| Free Thiol | ≦10% | ≦1% | ≦1% | ≦1% | ≦1% | ≦1% |

| | Time in Months | | | | | |
|---|---|---|---|---|---|---|
| Test | 5 | 6 | 9 | 12 | 15 | 18 |
| Purity | >99.5% | >99.5% | >99.5% | >99.5% | >99.5% | >99.5% |
| Aggregation | 0.1 | 1.30 | 0.30 | 0.14 | 0.078 | 0.065 |
| PLA2 (14C) | ANA | ANA | 57%[3] | 42% | 28% | 33% |
| PLA2 (HPLC) | ANA | ANA | ANA | ANA | 57% | 57 |
| Fibronectin (Fragment) | + | + | + | + | + | + |
| Isoelectric Focusing | 4.7 | 4.7 | 4.7 | 4.7 | 4.7 | 4.7 |
| Free Thiol | ≦1% | ≦1% | ≦1% | ≦1% | ≦1% | ≦1% |

[1]Limit of quantitation for these assays.
[2]Means Assay was not available at that time point.
[3]Ranges in development of the assay were 21% to 57% for this lot of rhUG.

TABLE 23

Results of Stability Tests on cGMP Lot at 4° C.

| Test | Spec | Time in Months | | | |
|---|---|---|---|---|---|
| | | 0 | 1 | 2 | 3 |
| Purity | ≧95% | 97.4% | 99.4% | 98.6% | 99.1% |
| Aggregation | ≦5% | 2.2% | 1.7% | 3.0% | 1.2% |
| PLA2 (14C) | + | ANA[1] | ANA | ANA | 39% |
| PLA2 (HPLC) | + | ANA | ANA | ANA | ANA |
| Fibronectin (Fragment) | + | + | na | + | + |
| Isoelectric Focusing | App. 4.7 | 4.7 | 4.7 | 4.7 | 4.7 |
| Free Thiol | ≦10% | ≦1% | ≦1% | ≦1% | ≦1% |

| Test | Time in Months | | | |
|---|---|---|---|---|
| | 6 | 9 | 12 | 15 |
| Purity | >99.5% | 99.3% | >99% | 99.2% |
| Aggregation | 1.2% | 0.5% | 0.5% | 0.6% |
| PLA2 (14C) | 39% | 66% | 69% | 76% |
| PLA2 (HPLC) | ANA | ANA | 87% | 76% |
| Fibronectin (Fragment) | + | + | + | + |
| Isoelectric Focusing | 4.7 | 4.7 | 4.7 | 4.7 |
| Free Thiol | ≦1% | ≦1% | ≦1% | ≦1% |

[1] means Assay was not available at that time point

TABLE 24

Results of Stability Tests on cGMP Lot at 25° C. and 60% RH

| Test | Spec | Time in Months | | | |
|---|---|---|---|---|---|
| | | 1 | 2 | 4 | 7 |
| Purity | ≧95% | 99.1% | 96.3% | >99% | 98.9% |
| Aggregation | ≦5% | 0.53% | 0.25% | 0.12% | 0.34% |
| PLA2 (14C) | + | 56% | 68% | 60% | 65% |
| PLA2 (HPLC) | + | ANA | 73% | 88% | 76% |
| Fibronectin (Fragment) | + | + | + | + | + |
| Isoelectric Focusing | App. 4.7 | 4.7 | 4.7 | 4.7 | 4.7 |
| Free Thiol | ≦10% | <1% | <1% | <1% | <1% |

As shown, both the development lot and the cGMP lot of rhUG were stable for more than 18 and 15 months, respectively, since they were originally produced and vialed. These rhUG preparations have been tested for a number of physical and chemical characteristics, as well as for biological activity in two potency assays. Based on these data, these preparations can be expected to perform the same in vivo, both with respect to each other and with respect to their original strength and types of biological activities as described herein and in application Ser. Nos. 08/864,357; 09/087,210; 09/120,264; 09/549,926; 09/861,688; PCT/US98/11026; PCT/US99/16312; PCT/US00/09979; and PCT/US01/12126.

Accordingly, the present invention provides commercially viable production processes for rhUG, as well as commercially viable pharmaceutical compositions and formulations.

REFERENCES

Carlomagno, T., Mantile, G., Bazzo, R., et al. Resonance assignment and secondary structure determination and stability of the recombinant human uteroglobin with heteronuclear multidimensional NMR. *J Biomol.NMR* 9:35–46, 1997.

Gerlitz, M., Hrabak, O. and Schwab, H. Partitioning of broad-host-range plasmid RP4 is a complex system involving site-specific recombination. *J Bacteriology* 172:6194–6203, 1990.

Mantile, G., Miele, L., Cordella-Miele, E., Singh, G., Katyal, S. L. and Mukherjee, A. B. Human Clara cell 10-kDa protein is the counterpart of rabbit uteroglobin. *J Biol Chem* 268:20343–20351, 1993.

Matthews, J. H., Pattabiraman, N., Ward, K. B., Mantile, G., Miele, L. and Mukherjee, A. B. Crystallization and characterization of the recombinant human Clara cell 10-kDa protein. *Proteins* 20:191–196, 1994.

Miele, L., Cordella-Miele, E. and Mukherjee, A. B. High level bacterial expression of uteroglobin, a dimeric eukaryotic protein with two interchain disulfide bridges, in its natural quaternary structure. *J Biol Chem* 265: 6427–6435, 1990.

Nieto et al., Purification and quarternary structure of the hormonally induced protein uteroglobin. *Arch. Biochem. Biophys*. 180:82–92, 1977.

Olivares, M. and Uauy, R. Limits of metabolic tolerance to copper and biological basis for present recommendations and regulations. *Am J Clin Nutr* 63:846S-852S, 1996.

Peter, W., Beato, M. and Suske, G. Recombinant rabbit uteroglobin expressed at high levels in *E. coli* forms stable dimers and binds progesterone. *Protein Eng.* 3:61–66, 1989.

Pilon, A.; Yost, P.; Lohnas, G.; Burkett, T.; Roberts, S.; Chase, T. E.; Bentley, W. E.; Ubiquitin Fusion Technology: Bioprocessing of Peptides. *Biotechnol. Prog.,* 13:374–379, 1997.

Singh, G., Katyal, S. L., Brown, W. E., et al. Amino-acid and cDNA nucleotide sequences of human Clara cell 10 kDa protein [published erratum appears in Biochim Biophys Acta 1989 Mar. 1; 1007(2):243]. *Biochim Biophys Acta* 950:329–337, 1988.

Zhang, Z., Kundu, G. C., Yuan, C. J., et al. Severe fibronectin-deposit renal glomerular disease in mice lacking uteroglobin. *Science* 276:1408–1412, 1997.

The invention claimed is:

1. A method of purifying rhUG comprising the steps of:
   a. providing a bacterial cell paste comprising bacterial cells capable of overexpressing rhUG;
   b. lysing the bacterial cell paste and pelleting the debris to form a supernatant;
   c. filtering the supernatant formed in step b through a first nominal molecular weight cut off membrane to form a first permeate;
   d. concentrating the first permeate formed in step c by the use of a second nominal molecular weight cut off membrane;
   e. loading the concentrated permeate formed in step d onto an anion exchange column to form a first eluate;
   f. concentrating the first eluate formed in step e by the use of a third nominal molecular weight cut off membrane to form a second concentrate;
   g. loading the second concentrate formed in step f onto a hydroxyapatite column to form a second eluate;
   h. separating host-derived proteins from the rhUG in the second eluate formed in step g to provide purified rhUG; and
   i. recovering the purified rhUG formed in step h.

2. The method of claim 1, wherein lysing comprises shearing.

3. The method of claim 1, wherein between step b and step c, cell debris is removed by centrifugation.

4. The method of claim 1, wherein the membrane of step b is about a 30K to 100K nominal molecular weight cut off membrane.

5. The method of claim 4, wherein the filtering of step c comprises the use of a tangential flow filtration system.

6. The method of claim 1, wherein the membrane of step d is about a 5K nominal molecular weight cut off membrane.

7. The method of claim 6, wherein the host-derived proteins of step h are separated with a chelating fast flow resin column.

8. The method of claim 7, wherein the chelating fast flow resin column comprises copper.

9. The method of claim 8, wherein after step h a positively charged membrane is placed downstream of the chelating fast flow resin column forming a pass through substantially free of host derived proteins.

10. The method of claim 9, wherein the positively charged membrane is a filtration membrane.

11. The method of claim 1, wherein the second eluate is diafiltered through about a 30K nominal molecular weight cut off membrane.

12. The method of claim 1, wherein the rhUG recovered in step i is substantially free of aggregates.

13. A method of purifying rhUG comprising the steps of:
   a. providing bacterial cells capable of overexpressing rhUG;
   b. lysing the bacterial cells and pelleting the debris to form a supernatant liquid;
   c. filtering the liquid through a nominal molecular weight cut off membrane;
   d. loading the liquid onto an ion exchange column;
   e. separating host-derived proteins from the rhUG to provide purified rhUG; and
   f. recovering the purified rhUG
   wherein the level of endotoxin in said rhUG is less than 5 EU/mg.

14. The method of claim 13, wherein the filtering of step c comprises the use of a tangential flow filtration system.

15. The method of claim 13, wherein the host-derived proteins of step e are separated with a chelating fast flow resin column.

16. The method of claim 13, wherein the rhUG recovered in step f is substantially free of aggregates.

* * * * *